United States Patent
Zhang et al.

(10) Patent No.: US 10,259,816 B2
(45) Date of Patent: Apr. 16, 2019

(54) CONDENSED-RING PYRIMIDYLAMINO DERIVATIVE, PREPARATION METHOD THEREFOR, AND INTERMEDIATE, PHARMACEUTICAL COMPOSITION AND APPLICATIONS THEREOF

(71) Applicant: GUANGZHOU MAXINOVEL PHARMACEUTICALS CO., LTD., Guangdong (CN)

(72) Inventors: Nong Zhang, Shanghai (CN); Zusheng Xu, Shanghai (CN); Tinghan Wang, Shanghai (CN); Yuguang Wang, Shanghai (CN)

(73) Assignee: GUANGZHOU MAXINOVEL PHARMACEUTICALS CO., LTD., Guangdong (CN)

( * ) Notice: Subject to any disclaimer, the term of this patent is extended or adjusted under 35 U.S.C. 154(b) by 0 days.

(21) Appl. No.: 15/568,999

(22) PCT Filed: Apr. 22, 2016

(86) PCT No.: PCT/CN2016/079956
§ 371 (c)(1),
(2) Date: Oct. 24, 2017

(87) PCT Pub. No.: WO2016/169504
PCT Pub. Date: Oct. 27, 2016

(65) Prior Publication Data
US 2018/0127420 A1    May 10, 2018

(30) Foreign Application Priority Data

Apr. 24, 2015    (CN) .......................... 2015 1 0201702

(51) Int. Cl.
*C07D 487/04*    (2006.01)
*C07D 401/14*    (2006.01)
(Continued)

(52) U.S. Cl.
CPC .......... *C07D 487/04* (2013.01); *A61K 31/517* (2013.01); *A61K 31/519* (2013.01);
(Continued)

(58) Field of Classification Search
CPC .. C07D 487/04; C07D 401/14; C07D 409/14; C07D 495/04; C07D 401/12;
(Continued)

(56) References Cited

U.S. PATENT DOCUMENTS 6,399,603 B1    6/2002   Jacobs et al.
8,217,057 B2    7/2012   Cui et al.
(Continued)

FOREIGN PATENT DOCUMENTS

KR    201501967    *   1/2015
WO    0121598 A1       3/2001
(Continued)

OTHER PUBLICATIONS

Bursavich, M.G.,"Novel Mps1 kinase inhibitors: from purine to pyrrolopyrimidine and quinazoline leads." Bioorganic & medicinal chemistry letters 23.24 (2013): 6829-6833.*
(Continued)

*Primary Examiner* — John M Mauro
(74) *Attorney, Agent, or Firm* — Millen White Zelano and Branigan, PC; John Sopp

(57) ABSTRACT

Disclosed are a condensed-ring pyrimidylamino derivative, a preparation method therefor, and an intermediate, a pharmaceutical composition and applications thereof. The method for preparing the condensed-ring pyrimidylamino derivative comprises: in a solvent, in the presence of a palladium-containing catalyst, allowing a compound represented by formula I-a and a compound represented by formula I-b' to have a coupling reaction, and then preparing a compound represented by formula I by means of a deprotection reaction. Also disclosed applications of the condensed-ring pyrimidylamino derivative in the preparation of drugs for preventing, relieving and/or treating tumors or diseases caused by an anaplastic lymphoma kinase. The condensed-ring pyrimidylamino derivative of the present invention has an obvious restraint effect on the anaplastic lymphoma kinase.

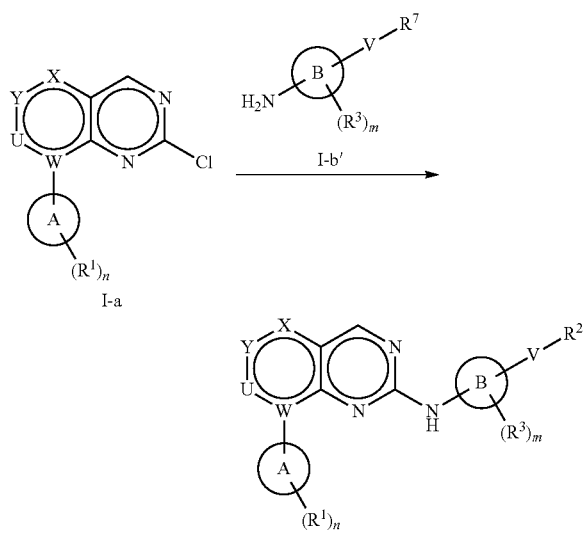

19 Claims, No Drawings

(51) Int. Cl.

| | | |
|---|---|---|
| C07D 405/14 | (2006.01) | |
| A61K 31/517 | (2006.01) | |
| A61K 31/519 | (2006.01) | |
| A61K 31/5377 | (2006.01) | |
| C07D 401/12 | (2006.01) | |
| C07D 405/12 | (2006.01) | |
| C07D 495/04 | (2006.01) | |
| C07D 239/78 | (2006.01) | |
| A61P 35/00 | (2006.01) | |
| C07D 409/14 | (2006.01) | |

(52) U.S. Cl.
CPC .......... *A61K 31/5377* (2013.01); *A61P 35/00* (2018.01); *C07D 239/78* (2013.01); *C07D 401/12* (2013.01); *C07D 401/14* (2013.01); *C07D 405/12* (2013.01); *C07D 405/14* (2013.01); *C07D 409/14* (2013.01); *C07D 495/04* (2013.01)

(58) Field of Classification Search
CPC .. C07D 239/78; C07D 405/12; C07D 405/14; A61P 35/00; A61K 31/5377; A61K 31/519; A61K 31/517
See application file for complete search history.

(56) References Cited

U.S. PATENT DOCUMENTS

| | | |
|---|---|---|
| 8,354,408 B2 | 1/2013 | Bourke et al. |
| 8,586,580 B2 | 11/2013 | Sim et al. |
| 8,765,755 B2 | 7/2014 | Bourke et al. |
| 9,126,931 B2 | 9/2015 | Kinoshita et al. |
| 9,440,922 B2 | 9/2016 | Kinoshita et al. |
| 9,499,560 B2 | 11/2016 | Bourke et al. |
| 9,550,770 B2 | 1/2017 | Qian et al. |
| 9,849,139 B2 | 12/2017 | Qian et al. |
| 9,879,028 B2 | 1/2018 | Gray et al. |
| 2006/0128724 A1 | 6/2006 | Cui et al. |
| 2008/0293769 A1 | 11/2008 | Cui et al. |
| 2011/0092499 A1 | 4/2011 | Bourke et al. |
| 2011/0207736 A1 | 8/2011 | Gray et al. |
| 2012/0083488 A1 | 4/2012 | Kinoshita et al. |
| 2012/0277424 A1 | 11/2012 | Sim et al. |
| 2013/0090336 A1 | 4/2013 | Bourke et al. |
| 2013/0261106 A1 | 10/2013 | Carry |
| 2014/0011810 A1 | 1/2014 | Gray et al. |
| 2015/0018350 A1 | 1/2015 | Bourke et al. |
| 2015/0150845 A1 | 6/2015 | Kinoshita et al. |
| 2015/0175601 A1 | 6/2015 | Qian et al. |
| 2016/0340308 A1 | 11/2016 | Kinoshita et al. |
| 2017/0050936 A1 | 2/2017 | Qian et al. |
| 2017/0196881 A1 | 7/2017 | Qian et al. |

FOREIGN PATENT DOCUMENTS

| | | | | |
|---|---|---|---|---|
| WO | 2006021881 A2 | 3/2006 | | |
| WO | 2007066185 A2 | 6/2007 | | |
| WO | 2008053157 A1 | 5/2008 | | |
| WO | 2009062258 A1 | 5/2009 | | |
| WO | 2010143664 A1 | 12/2010 | | |
| WO | 2011049332 A2 | 4/2011 | | |
| WO | 2011079231 A1 | 6/2011 | | |
| WO | 2012106540 A1 | 8/2012 | | |
| WO | WO-2013082476 A1 * | 6/2013 | ............. | A61K 31/52 |
| WO | 2015027222 A2 | 2/2015 | | |
| WO | WO-2016006921 A1 * | 1/2016 | ............ | A61K 31/506 |
| WO | WO-2017007712 A1 * | 1/2017 | ............. | A61K 38/08 |

OTHER PUBLICATIONS

Jul. 20, 2016 Written Opinion of the International Searching Authority issued in International Patent Application No. PCT/CN2016/079956.
Mar. 2, 2018 English Office Action issued in European Patent Application No. 16782651.0.
Chinese Patent Application No. 201510201702.0 filed Apr. 24, 2015 (not published).
English Translation of Chinese Patent Application No. 201510201702.0 filed Apr. 24, 2015 (not published).
Tartari C.J., et al., J.Bio. Chem., 2008, 283(7), 3743-3750.
Lin E., et al., Mol.CancerRes., 2009, 7, 1466-1476.
Webb TR, et al., Expert Rev.AnticancerTher., 2009, 9 (3), 331-356.
Bilsland J. G., et al., Neuropsycho-pharmacology, 2008, 33, 685-700.
Jul. 20, 2016 International Search Report issued in International Patent Application No. PCT/CN2016/079956.
Palmer R. H., et al., Biochem J., 2009, 420, 345-361.
Supplementary Office Action issued in European Patent Application No. 16782651.0 dated Jun. 11, 2018 (11 pages).

* cited by examiner

CONDENSED-RING PYRIMIDYLAMINO DERIVATIVE, PREPARATION METHOD THEREFOR, AND INTERMEDIATE, PHARMACEUTICAL COMPOSITION AND APPLICATIONS THEREOF

The present application is the U.S. national stage application of International Application PCT/CN2016/079956, filed Apr. 22, 2016, which international application was published on Oct. 27, 2016, as International Publication WO2016/169504A1. The International Application claims priority of Chinese Patent Application 201510201702.0, filed Apr. 24, 2015, the contents of which are incorporated herein by reference in their entireties.

FIELD OF INVENTION

The present invention relates to a condensed-ring pyrimidylamino derivative, a preparation method therefor, and an intermediate, a pharmaceutical composition and a use thereof.

PRIOR ARTS

Anaplastic lymphoma kinase (ALK) of receptor tyrosine kinase was firstly found in anaplastic large cell lymphoma (ALCL). The fusion protein formed by translocation of chromosome 2 and 5 contains the 3'terminal intracellular domain of ALK and the 5' terminaldomain of nuclear phosphoprotein (nucleophosmin, NPM). The ALK gene is located at chromosome 2p23 locus. Under normal circumstances the human ALK transcribes to produce mRNA with a size of 6222 bp, which consisting of 29 exons and encodes a 1620 amino acid sequence of 200 KDa type I transmembrane protein ALK. The protein is a receptor tyrosine kinase (RTK) and a member of the RTK insulin superfamily (Palmer R. H., et al., Biochem J., 2009, 420, 345-361.). The complete ALK has a typical three-part structure of RTK, namely extracellular domain, lipophilic transmembrane region, and cytosolictyrosine kinase. The extracellular domain contains a specific binding domain: N-terminal signal peptide, two methyl dopa, A5 protein and receptor protein tyrosine phosphatase µ(MAM, meprin) domain, one low density lipoprotein A (LDLa) motif and a glycine-rich region (G-rich) near the cell membrane. MAM domain and G-rich region may be associated with the ALK activation. The first tyrosine residue, Tyr1604, of the human ALK kinase region YxxxYY motif has been shown to be associated with autologous activation of the ALK kinase region (Tartari C. J., et al., J. Bio. Chem., 2008, 283(7), 3743-3750.).

The translocation of the chromosomes results in the formation of the ALK fusion gene, which encodes a fusion protein that forms a non-ligand-dependent dimer that causes constitutive ALK activation. The activated ALK signal could cause excessive proliferation and malignant transformation of cells by activating its downstream signaling pathway of RAS-MEK-ERK, JAK-STAT3/5, PI3K-AKT and PLCγ.

Since ALK fusion gene has been reported for the first time in the study of anaplastie large cell lymphoma (ALCL) in 1994, ALK has been found to be able to fuse with a variety of genes, and this variety of fusion genes are closely related to the occurrence of a variety of tumors. Such as NMP-ALK fusion gene is associated with anaplastic large cell lymphoma (ALCL) and diffuse large B-cell lymphoma (DLBCL), TPM3-ALK fusion gene is associated with anaplastic large cell lymphoma (ALCL), inflammatory myofibroblastoma (IMT), histiocytoma (Histioc. Tumor) and kidney cancer; and EML4-ALK fusion gene is closely related to non-small cell lung cancer (NSCLC), kidney cancer, breast cancer and colon cancer, which become the focus of the current study (Lin E., et al., Mol. Cancer Res., 2009, 7, 1466-1476.). In addition, ALK fusion gene was detected in neuroblastoma, melanoma, rhabdomyoma and esophageal squamous cell tumors (Webb T R, et al., Expert Rev. Anticancer Ther., 2009, 9 (3), 331-356.).

ALK is also associated with neurological diseases. Recent studies have shown that ALK has the function of regulating the frontal cortex and hippocampus of adult animals. ALK can be used as a new target for the treatment of mental illness, such as schizophrenia, depression and substance (heroin) addiction (Bilsland J. G., et al., Neuropsychopharmacology, 2008, 33, 685-700.).

Currently available ALK inhibitors are Pfizer's Crizotinib (WO2006021881, WO2007066185, WO2008053157), Novart's Ceritinib (WO2012106540) and Roche's Alectinib (WO2010143664). The development of ALK kinase inhibitor can effectively reduce the effect of mutant ALK gene on downstream signaling pathway, and thus affects the invasion and proliferation and other effects of tumor cells, and finally affects the growth of tumor cells and play an anti-tumor effect.

CONTENT OF THE PRESENT INVENTION

The present invention provides a condensed-ring pyrimidylamino derivative, a preparation method therefor, and an intermediate, a pharmaceutical composition and use thereof. The condensed-ring pyrimidylamino derivative of the present invention has a strong inhibitory effect on anaplastic lymphoma kinase (ALK) and is a novel and highly effective anaplastic lymphoma kinase inhibitor.

The present invention provides a condensed-ring pyrimidylamino derivative having a structure of formula I, a tautomer, a mesomer, a racemate, a stereoisomer, a pharmaceutically acceptable salt, a metabolite, a metabolic precursor or a prodrug thereof:

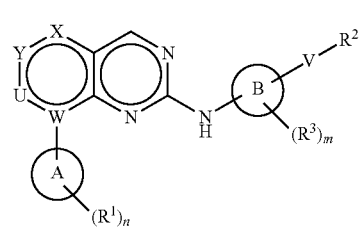

wherein,
X is selected from CH, S or $NR^4$;
Y is selected from N or $CR^4$;
U is a chemical bond or CH;
V is a chemical bond or —CONH—;
W is selected from N or C;
ring A is an aromatic ring or a heteroaromatic ring;
ring B is an aromatic ring or a heteroaromatic ring;
$R^1$ is selected from hydrogen atom, hydroxyl, a halogen, an alkyl, a sulfonyl, an alkoxy, formyl, amino, an amide or a heteroaryl, or the two adjacent $R^1$(s) and the two atoms on the ring A connected to them form a 5- to 7-membered carbon heterocyclic ring together; in the carbon heterocyclic ring, the heteroatom(s) is(are) oxygen and/or nitrogen, the number of the heteroatom(s) is 1 to 4, and the number of carbon atom(s) is 1 to 6;

$R^2$ is selected from hydrogen atom, hydroxyl, a halogen, an alkyl, an alkoxy, an amide, a cycloalkyl or a heterocycloalkyl;

$R^3$ is selected from hydrogen atom, hydroxyl, a halogen, an alkyl, an alkoxy, or the two adjacent $R^3$(s) together with the carbon atoms on the ring B to which they are attached to form a 5- to 7-membered heterocyclyl together; the heterocyclyl is a heterocyclyl wherein the heteroatom is selected from the group consisting of oxygen, nitrogen and sulfur, the number of the heteroatom(s) is 1 to 4, the number of carbon atoms is 2 to 6;

$R^4$ is selected from hydrogen atom, a halogen or an alkyl; n is 1 or 2;
m is 1 or 2.

In the ring A, the aromatic ring is preferably a $C_{6-10}$ aromatic ring, more preferably benzene ring. The heteroaromatic ring is preferably a heteroaromatic ring having 2 to 5 carbon atoms in which the heteroatom is nitrogen atom and the number of the heteroatom(s) is 1 to 3, more preferably a heteroaromatic ring having 2 to 3 carbon atoms in which the heteroatom is nitrogen atom and the number of the heteroatom(s) is 1 or 2, most preferably pyrazole ring or triazole.

In the ring B, the aromatic ring is preferably a $C_{6-10}$ aromatic ring, more preferably benzene ring. The heteroaromatic ring is preferably a heteroaromatic ring having 2 to 5 carbon atoms in which the heteroatom is nitrogen atom and the number of the heteroatom(s) is 1 to 3, more preferably a heteroaromatic ring having 2 to 3 carbon atoms in which the heteroatom is nitrogen atom and the number of heteroatoms is 1 or 2, most preferably a pyrazole ring.

In the $R^1$, the halogen is preferably fluorine or chlorine. The alkyl is preferably a $C_{1-4}$ alkyl. The sulfonyl is preferably a $C_{1-4}$ sulfonyl; more preferably a methanesulfonyl. The alkoxy is preferably a $C_{1-4}$ alkoxy. The heteroaryl is preferably a heteroaryl having 2 to 5 carbon atoms in which the heteroatom is nitrogen atom and the number of the heteroatom(s) is 1 to 3, more preferably pyrazolyl. The carbon heterocyclic ring is preferably one having 2 to 5 carbon atoms in which the heteroatom is oxygen, the number of the heteroatom(s) is 1 or 2, more preferably one having 3 to 5 carbon atoms in which the heteroatom is oxygen, the number of the heteroatom(s) is 1 or 2.

In the $R^1$, the hydroxy, the alkyl, the alkoxy, the formyl, the amino, the sulfonyl or the heteroaryl may be further independently substituted by a substituent selected from the group consisting of a halogen, a $C_{1-10}$ alkyl, hydroxy, amino, a $C_{1-10}$ alkoxy, a $C_{1-4}$ sulfonyl and a heterocycloalkyl having 3 to 8 carbon atoms in which the heteroatom is oxygen and/or nitrogen and the number of the heteroatom(s) is 1 to 4. Wherein the halogen is preferably fluorine; the $C_{1-10}$ alkyl is preferably a $C_{1-4}$ alkyl; the $C_{1-10}$ alkoxy is preferably a $C_{1-4}$ alkoxy; the $C_{1-4}$ sulfonyl is preferably a methanesulfonyl; the heterocycloalkyl is preferably a heterocycloalkyl having 4 to 6 carbon atoms in which the heteroatom is oxygen and/or nitrogen, the number of the heteroatom(s) is 1 to 4, more preferably morpholinyl. The carbon heterocyclic ring may be further substituted by a substituent selected from the group consisting of a $C_{1-4}$ alkyl.

In the $R^2$, the alkyl is preferably a $C_{1-4}$ alkyl, the alkoxy is preferably a $C_{1-4}$ alkoxy, the amide is preferably a formamide, the heterocycloalkyl is preferably a heterocycloalkyl having 3 to 8 carbon atoms in which the heteroatom is oxygen and/or a nitrogen and the number of the heteroatom(s) is 1 to 4, more preferably a heterocycloalkyl having 4 to 6 carbon atoms in which the heteroatom is nitrogen and the number of the heteroatom(s) is 1 to 2, most preferably piperidinyl. Wherein the heterocycloalkyl may be further substituted by a substituent selected from the group consisting of: hydroxy, a $C_{1-4}$ alkyl, a $C_{1-4}$ acyl.

In the $R^3$, the alkyl is preferably a $C_{1-4}$ alkyl, the alkoxy is preferably a $C_{1-4}$ alkoxy, the heterocyclyl is preferably a heterocyclyl having 2 to 4 carbon atoms in which the heteroatom is oxygen and the number of the heteroatom(s) is 1 to 2.

In the $R^3$, the hydroxyl, the alkyl or the alkoxy may be further independently substituted by a substituent selected from the group consisting of a halogen (preferably fluorine), a $C_{1-4}$ alkyl, hydroxy, amino, a $C_{1-4}$ alkoxy, a $C_{1-4}$ sulfonyl (preferably methanesulfonyl) and an amide; the heterocyclyl may be further substituted by a substituent selected from the group consisting of a $C_{1-4}$ alkyl.

In the $R^4$, the halogen is preferably fluorine; the alkyl is preferably a $C_{1-4}$ alkyl.

The $R^1$ is preferably

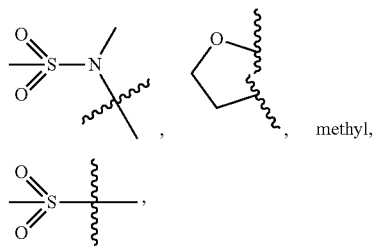, methyl, methoxy, ethoxy, trifluoromethyl, fluorine,

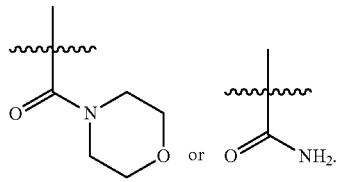

The $R^2$ is preferably

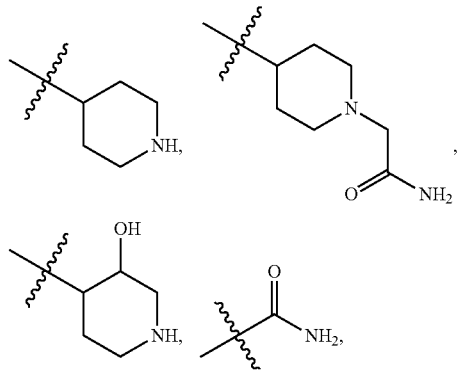

-continued
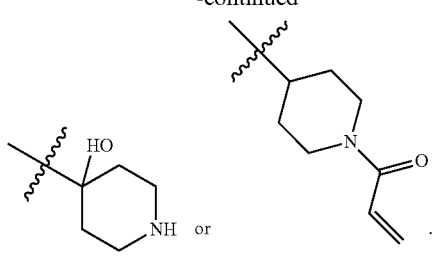
The R³ is preferably methoxy, isopropoxy, methyl,
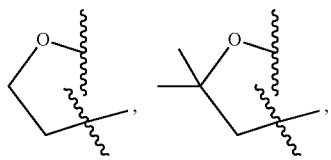
isopropyl,
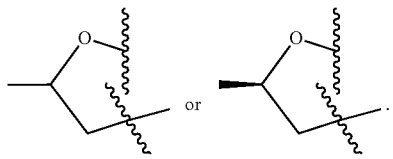
The R⁴ is preferably methyl or fluorine.
The
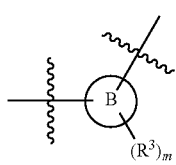
is preferably
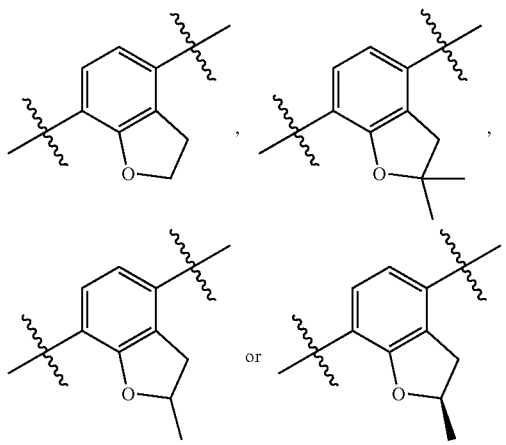
The
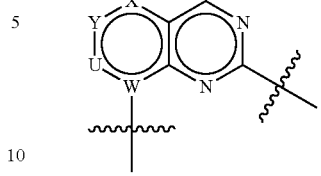
is preferably
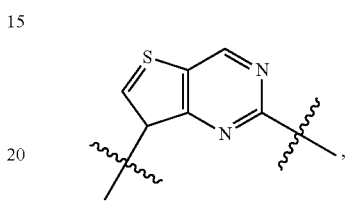
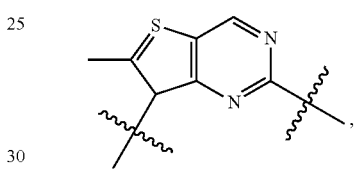
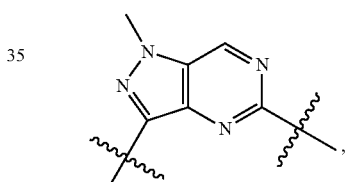
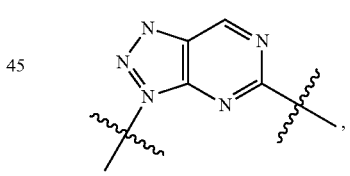
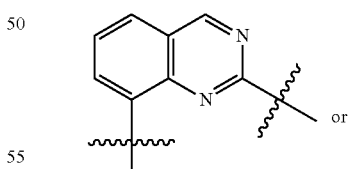
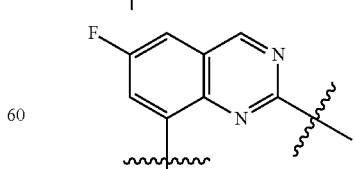
The condensed-ring pyrimidylamino derivative is preferably represented by formula II-1 or II-2,

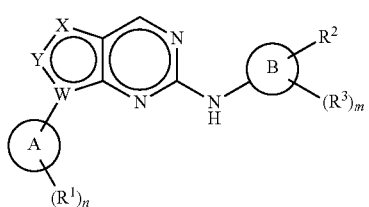

II-1

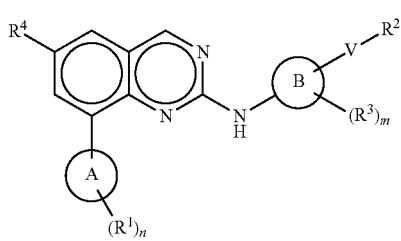

II-2 wherein A, B, R$^1$, R$^2$, R$^3$, R$^4$, X, Y, V, W, n and m are as defined above.

The condensed-ring pyrimidylamino derivative having the structure of formula II-1 is preferably represented by formula III-1-1 or III-1-2,

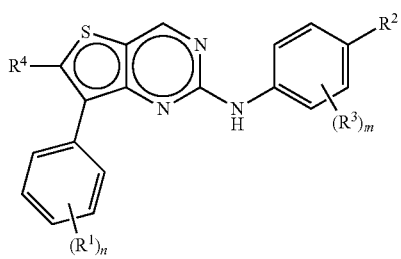

III-1-1

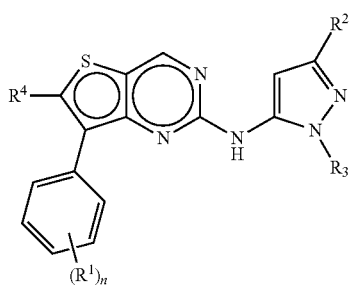

III-1-2 wherein R$^1$, R$^2$, R$^3$, R$^4$, n and m are as defined above.

The condensed-ring pyrimidylamino derivative having the structure of formula II-2 is preferably represented by formula III-2-1 or III-2-2,

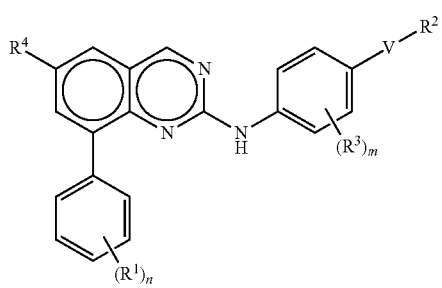

III-2-1

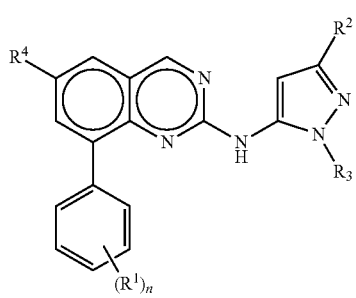

III-2-2 wherein R$^1$, R$^2$, R$^3$, R$^4$, V, n and m are as defined above.

The condensed-ring pyrimidylamino derivative having the structure of formula I is preferably selected from the group consisting of

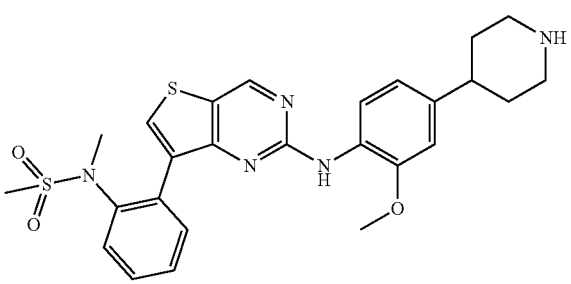

1

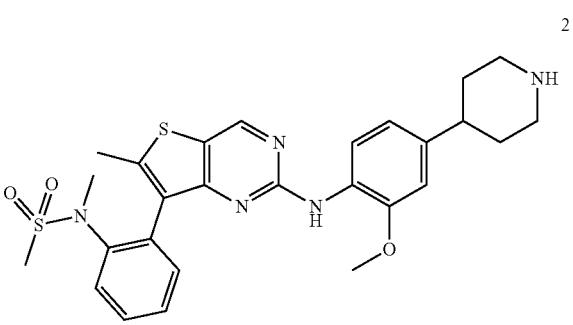

2

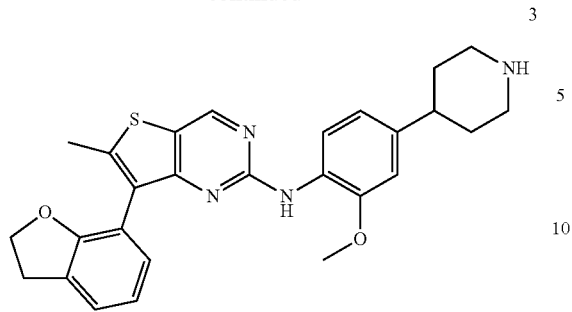
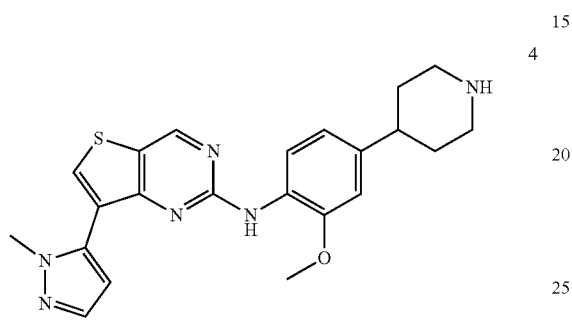
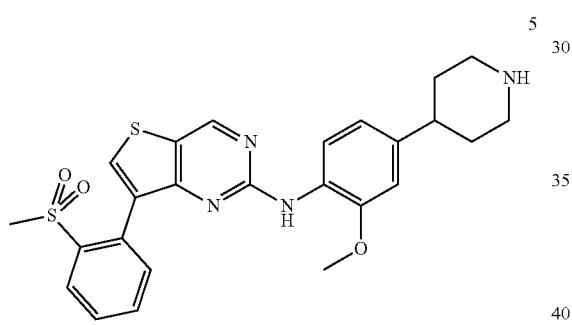
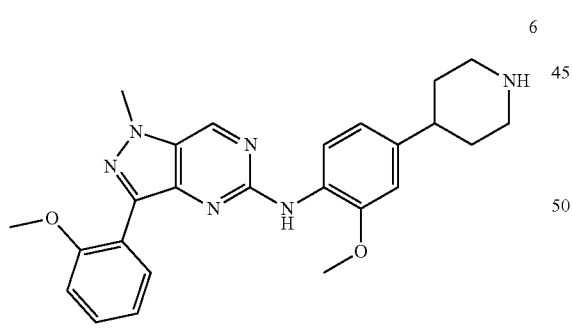
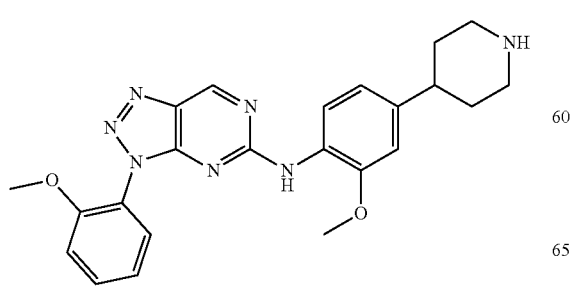
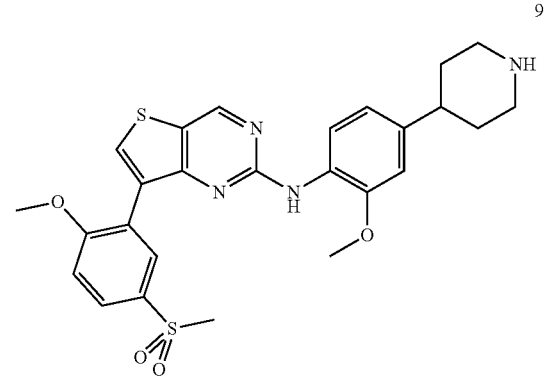
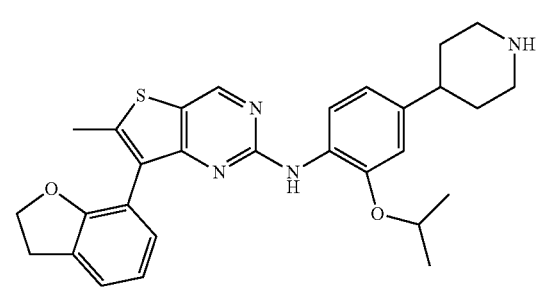
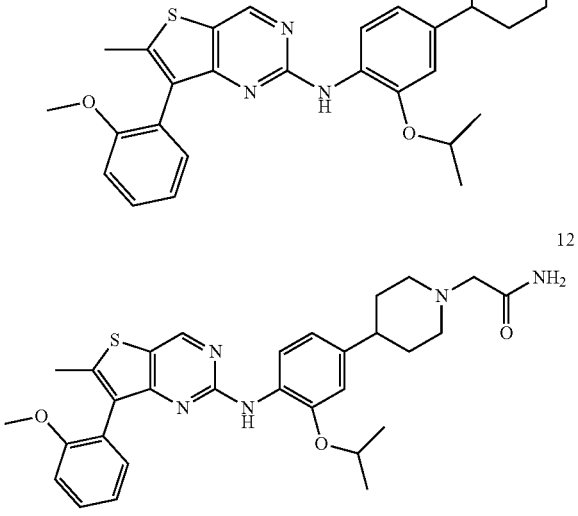

13
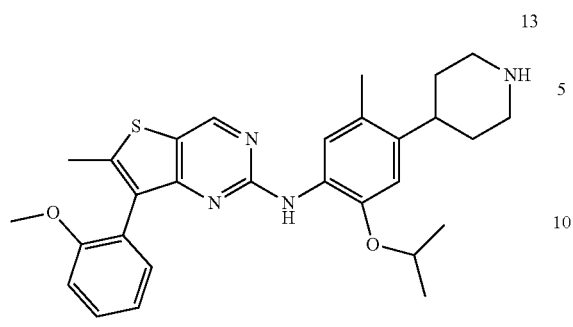
14
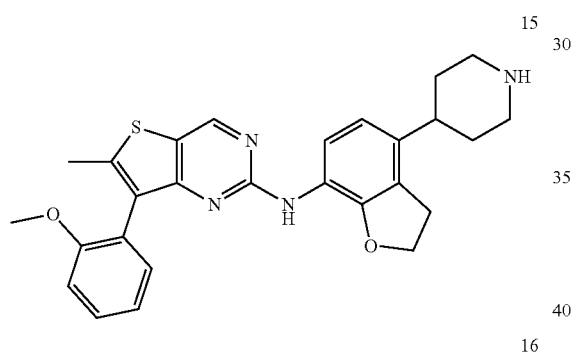
15
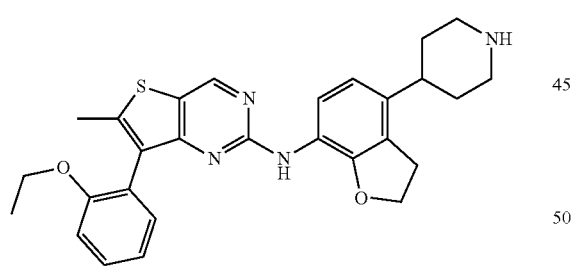
16
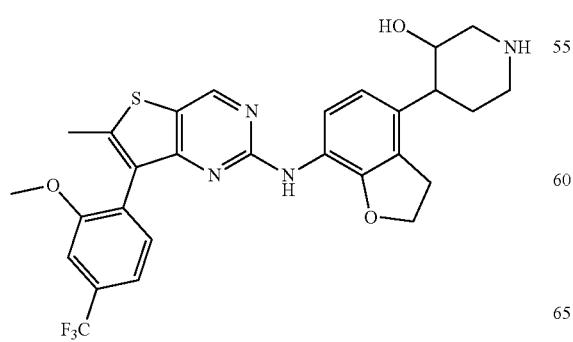
17
18
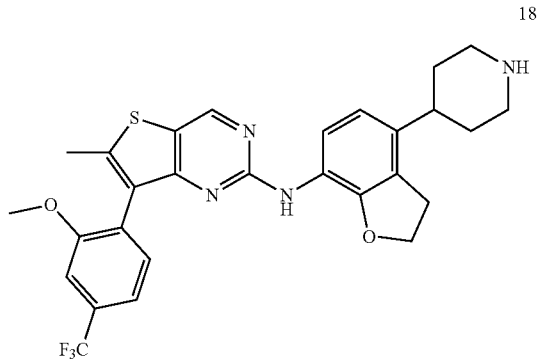
19
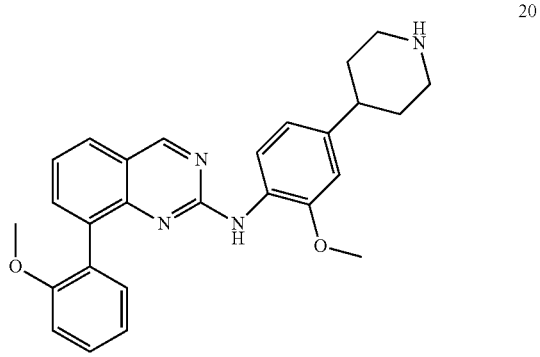
20
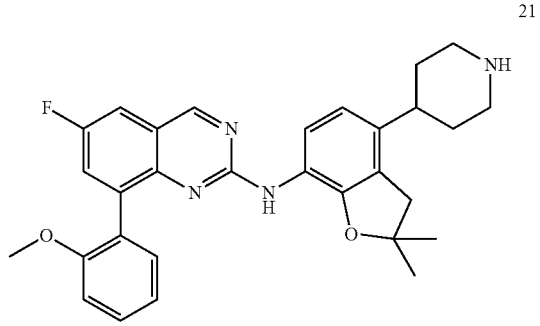
21
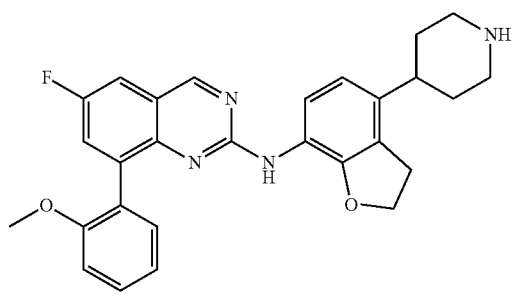
22

-continued
23
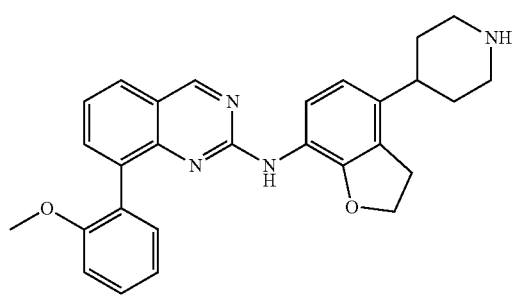
24
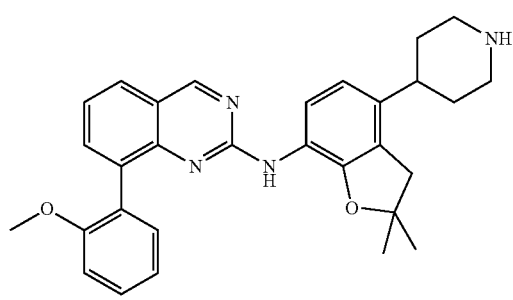
25
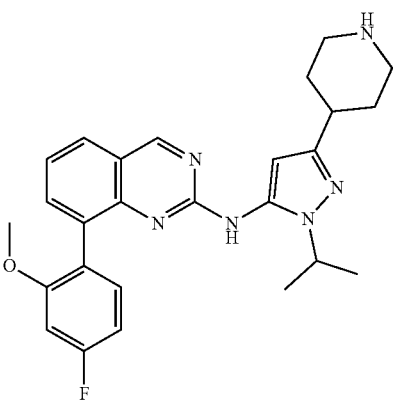
26
-continued
27
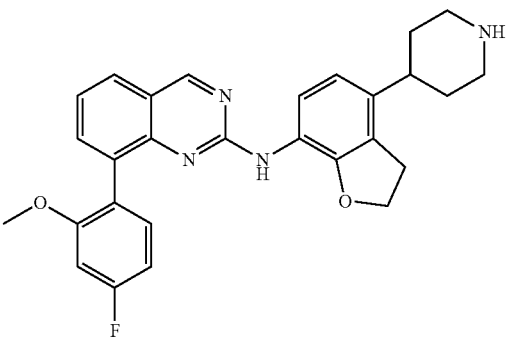
28
29
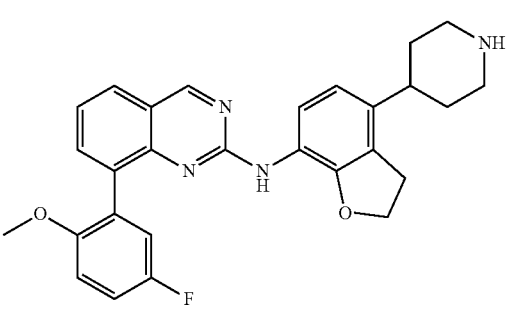
30
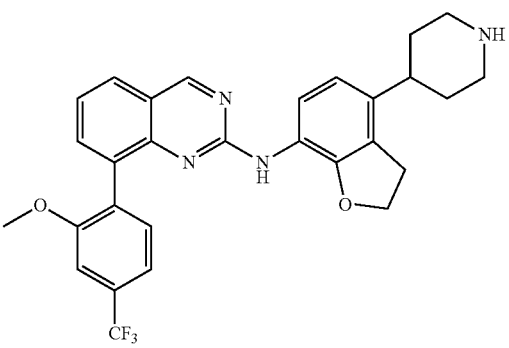

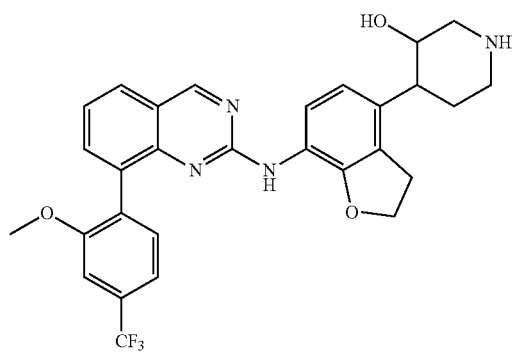
31
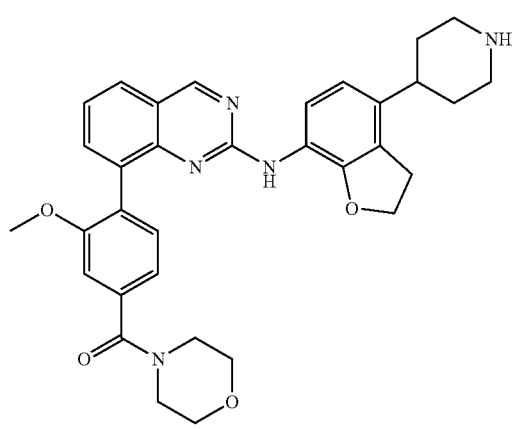
32
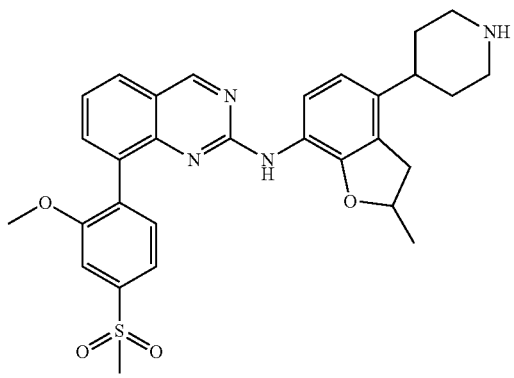
35
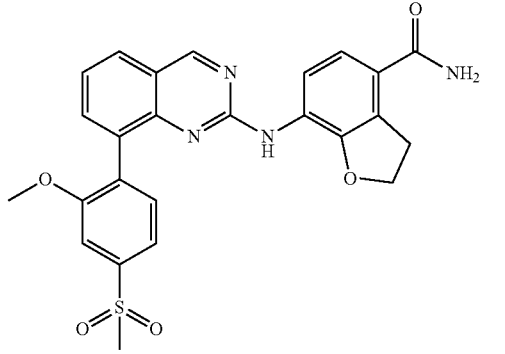
36
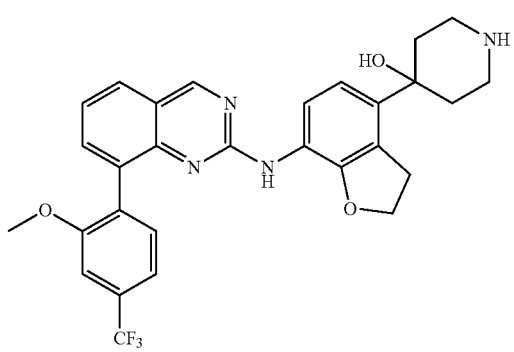
37
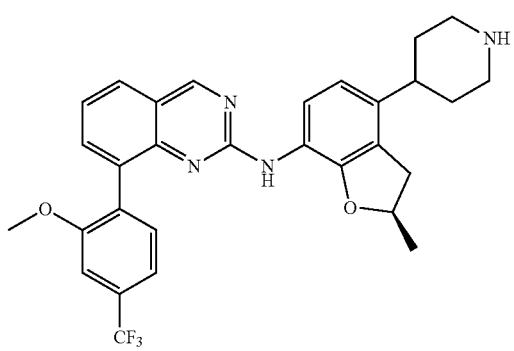
38

39
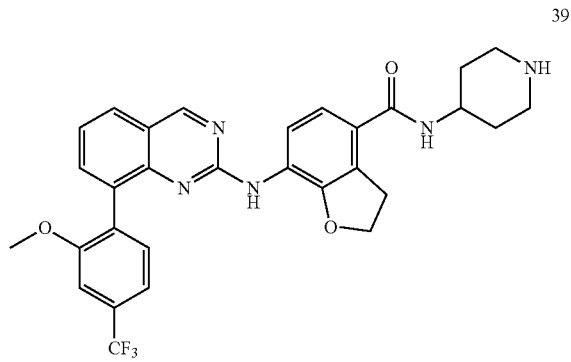

40
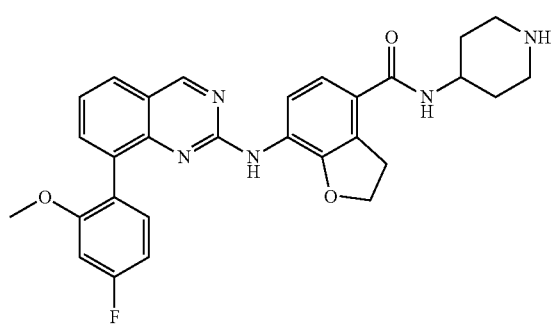

41
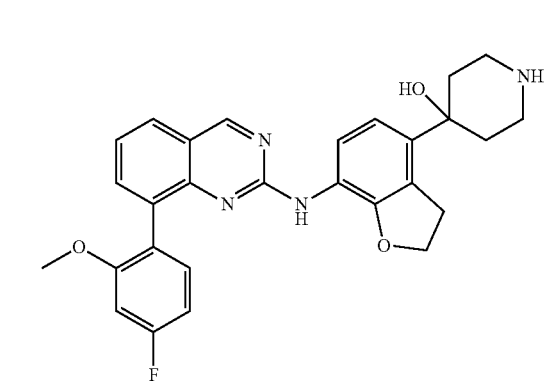

42
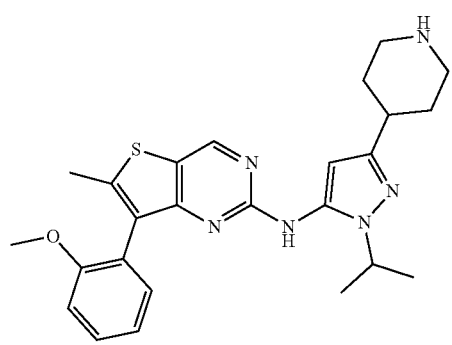

43
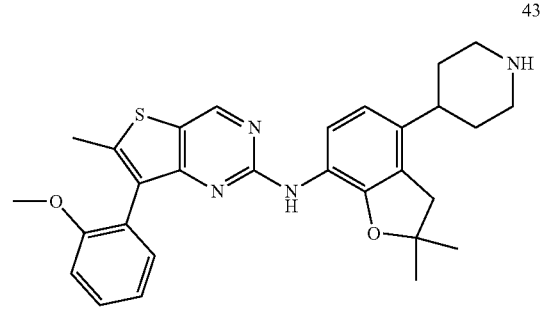

44
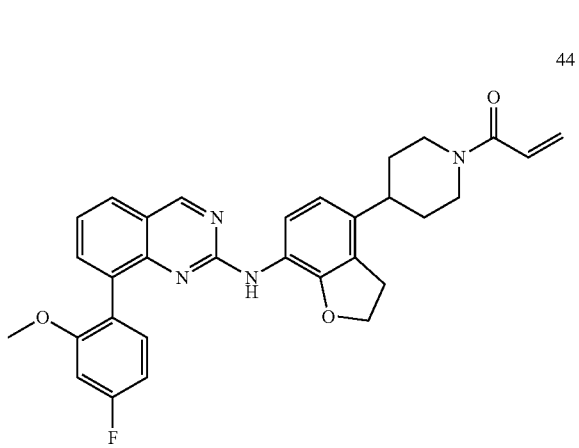

45
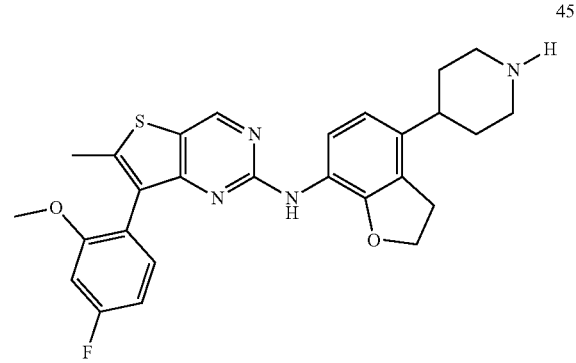

In the present invention, the condensed-ring pyrimidylamino derivative may be a racemate or has an optical activity.

The present invention also provides a process for preparing the condensed-ring pyrimidylamino derivative having the structure of formula I, the tautomer, the mesomer, the racemate, the stereoisomer, the pharmaceutically acceptable salt, the metabolite, the metabolic precursor or the prodrug thereof, which can be synthesized according to the method known in the art with commercially available raw materials, preferably comprising: in a solvent, in the presence of a palladium-containing catalyst, allowing a compound represented by formula I-a and a compound represented by formula I-b' to have a coupling reaction, and then preparing a compound represented by formula I by means of a deprotection reaction,

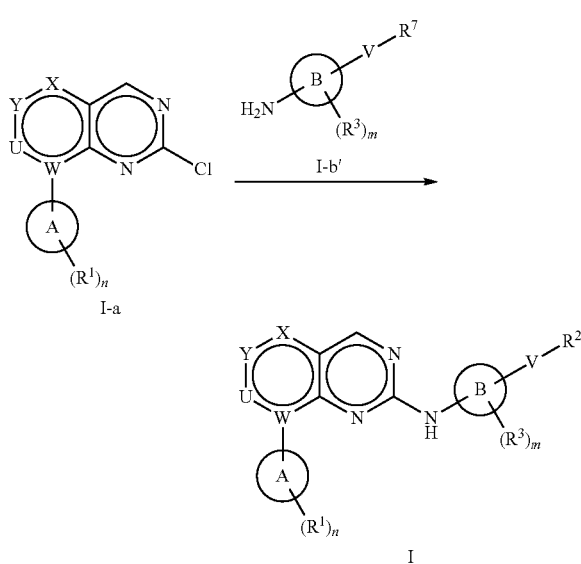

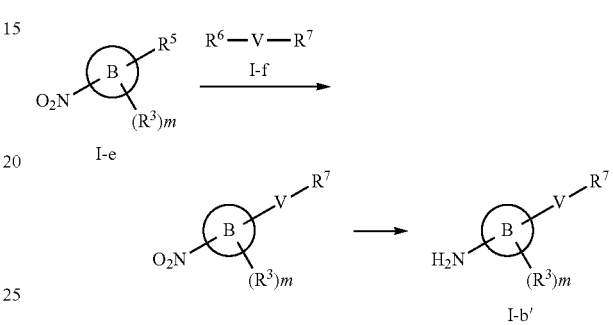

In formula I-a, formula I-b and formula I, A, B, $R^1$, $R^2$, $R^3$, X, Y, U, V, W, n and m are as defined above, $R^7$ is $R^2$ that protected by Boc.

The methods and conditions of the coupling reaction are conventional methods and conditions for such reaction in the art.

A base may also be involved in the coupling reaction. The base is preferably an alkali metal carbonate, more preferably sodium carbonate, potassium carbonate or cesium carbonate. The molar ratio of the base to the compound I-a is preferably 1:1 to 5:1.

The solvent is preferably an organic solvent and/or water. The organic solvent may be an organic solvent commonly used in such reactions in the art, preferably selected from the group consisting of 1,4-dioxane, toluene, ethylene glycol dimethyl ether and N,N-dimethylformamide, more preferably 1,4-dioxane. The volume-to-mass ratio of the organic solvent to the compound having the structure of formula I-a is preferably 10 mL/g to 110 mL/g. The amount of the water to be added is preferably 1 to 100% of the volume of the organic solvent.

The palladium-containing catalyst may be a palladium-containing catalyst commonly used in such coupling reaction, preferably selected from the group consisting of tris(dibenzylideneacetone)dipalladium, palladium acetate, tetrakis(triphenylphosphine)palladium and [1,1'-bis(diphenylphosphino)ferrocene]dichloropalladium(II). The molar ratio of the palladium-containing catalyst to the compound having the structure of formula I-a is preferably (0.005:1) to (0.5:1), more preferably (0.01:1) to (0.10:1).

In the coupling reaction, the molar ratio of the compound having the structure of formula I-a to the compound having the structure of formula I-b' is preferably (0.5:1) to (2:1), more preferably (0.9:1) to (1.5:1).

The temperature of the coupling reaction is preferably 50° C. to 150° C., more preferably 90° C. to 120° C.

The progress of the coupling reaction may be monitored by TLC or HPLC, generally the end of the reaction is that the compound having the structure of formula I-a disappears.

When the coupling reaction is complete, the product can be further purified by a work-up. The work-up preferably comprises the steps that are selected from the group consisting of recrystallization, silica gel thin layer chromatography preparative plate purification, silica gel column purification and preparative high performance liquid chromatography purification.

The deprotection reaction may be a conventional deprotection reaction in the art.

Some of the compound having the structure of I-b' could be prepared by the following methods:

in a solvent, in the presence of a palladium-containing catalyst, reacting a compound having a structure of I-e and a compound having a structure of I-f by a coupling reaction, followed by a reduction reaction to deliver the compound having the structure of I-b', wherein, $R^5$ is a halogen, preferably Cl or Br; $R^6$ is a boric acid or a borate; In formula I-b', formula I-e and formula I-f, B, $R^3$, V and m are as defined above, $R^7$ is $R^2$ that protected by Boc.

In the process of preparing the compound of formula I-b', a base may also be involved in the coupling reaction. The base is preferably an alkali metal carbonate, more preferably sodium carbonate, potassium carbonate or cesium carbonate. The molar ratio of the base to the compound I-e is preferably 1:1 to 5:1.

In the process of preparing the compound having the structure of formula I-b', the methods and conditions of the coupling reaction are conventional methods and conditions for such reaction in the art.

In the process of preparing the compound having the structure of formula I-b', the solvent is preferably an organic solvent and/or water. The organic solvent may be an organic solvent commonly used in such reactions in the art, preferably selected from the group consisting of 1,4-dioxane, toluene, ethylene glycol dimethyl ether and N,N-dimethylformamide, more preferably 1,4-dioxane. The volume-to-mass ratio of the organic solvent to the compound having the structure of formula I-e is preferably 5 mL/g to 100 mL/g. The amount of the water to be added is preferably 1 to 100% of the volume of the organic solvent.

In the process of preparing the compound having the structure of formula I-b', the palladium-containing catalyst may be a palladium-containing catalyst commonly used in such coupling reaction, preferably selected from the group consisting of tris(dibenzylideneacetone)dipalladium, palladium acetate, tetrakis(triphenylphosphine)palladium and [1,1'-bis(diphenylphosphino)ferrocene]dichloropalladium (II). The molar ratio of the palladium-containing catalyst to the compound having the structure of formula I-e is preferably (0.005:1) to (0.5:1), more preferably (0.01:1) to (0.10:1).

In the process of preparing the compound having the structure of formula I-b', in the coupling reaction, the molar ratio of the compound having the structure of formula I-e to the compound having the structure of formula I-f is preferably (0.5:1) to (2:1), more preferably (0.9:1) to (1.5:1).

In the process of preparing the compound having the structure of formula I-b', the temperature of the coupling reaction is preferably 50° C. to 150° C.

In the process of preparing the compound having the structure of formula I-b', the progress of the coupling reaction may be monitored by TLC or HPLC, generally the end of the reaction is that the compound having the structure of formula I-e disappears.

In the process of preparing the compound having the structure of formula I-b', when the coupling reaction is complete, the product can be further purified by a work-up. The work-up preferably comprises the steps that are selected from the group consisting of recrystallization, silica gel thin layer chromatography preparative plate purification, silica gel column purification and preparative high performance liquid chromatography purification.

In the process of preparing the compound having the structure of formula I-b', the reduction reaction may be a conventional reduction reaction in the art, including nitro reduction, unsaturated olefin reduction, amino reduction or benzyl reduction or the like.

In the coupling reaction, the compound having the structure of I-a may be prepared by the following method: in a solvent, in the presence of a palladium-containing catalyst, reacting a compound having a structure of I-c and a compound having a structure of I-d by a coupling reaction to deliver the compound of formula I-a,

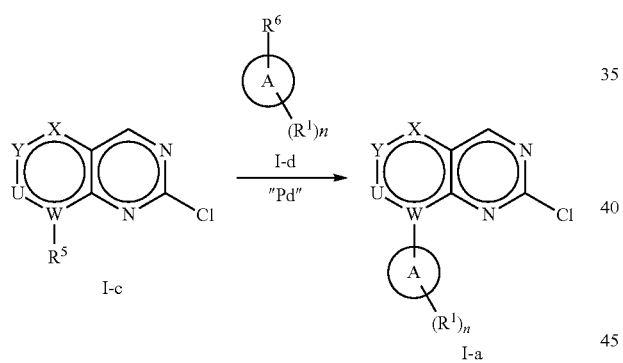

wherein, $R^5$ is a halogen, preferably Cl or Br; $R^6$ is a boric acid or a borate; In formula I-a, formula I-c and formula I-d, A, $R^1$, X, Y, U, W and n are as defined above.

In the process of preparing the compound of formula I-a, a base may also be involved in the coupling reaction. The base is preferably an alkali metal carbonate, more preferably sodium carbonate, potassium carbonate or cesium carbonate. The molar ratio of the base to the compound I-c is preferably 1.0:1 to 5:1.

In the process of preparing the compound of formula I-a, the solvent is preferably an organic solvent and/or water. The organic solvent may be an organic solvent commonly used in such reactions in the art, preferably selected from the group consisting of 1,4-dioxane, toluene, ethylene glycol dimethyl ether and N,N-dimethylformamide, more preferably 1,4-dioxane. The volume-to-mass ratio of the organic solvent to the compound having the structure of formula I-c is preferably 5 mL/g to 100 mL/g. The amount of the water to be added is preferably 1 to 100% of the volume of the organic solvent.

In the process of preparing the compound of formula I-a, the palladium-containing catalyst may be a palladium-containing catalyst commonly used in such coupling reaction, preferably selected from the group consisting of tris(dibenzylideneacetone)dipalladium, palladium acetate, tetrakis(triphenylphosphine)palladium and [1,1'-bis(diphenylphosphino)ferrocene]dichloropalladium(II). The molar ratio of the palladium-containing catalyst to the compound having the structure of formula I-cis preferably (0.005:1) to (0.5:1), more preferably (0.01:1) to (0.10:1).

In the process of preparing the compound of formula I-a, the molar ratio of the compound having the structure of formula I-d to the compound having the structure of formula I-c is preferably (0.5:1) to (2:1), more preferably (0.9:1) to (1.5:1).

In the process of preparing the compound of formula I-a, the temperature of the coupling reaction is preferably 50° C. to 150° C., more preferably 90° C. to 110° C.

In the process of preparing the compound of formula I-a, the progress of the coupling reaction could be monitored by TLC or HPLC, generally the end of the reaction is that the compound having the structure of formula I-c disappears.

In the process of preparing the compound of formula I-a, when the coupling reaction is complete, the product can be further purified by a work-up. The work-up preferably comprises the steps that are selected from the group consisting of recrystallization, silica gel thin layer chromatography preparative plate purification, silica gel column purification and preparative high performance liquid chromatography purification.

The present invention also provides a compound having the structure of formula I-a,

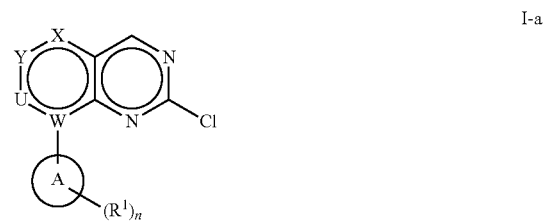

wherein, A, $R^1$, X, Y, U, W and n are as defined above.

The compound having the structure of formula I-a is preferably selected from the group consisting of

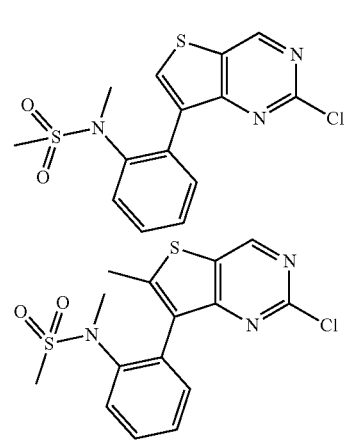

-continued
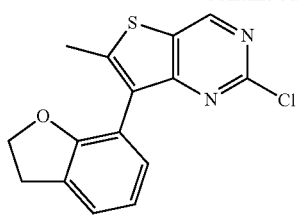
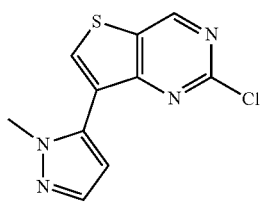
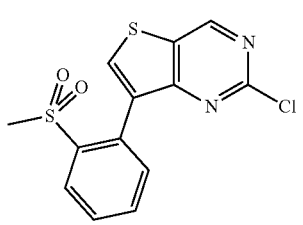
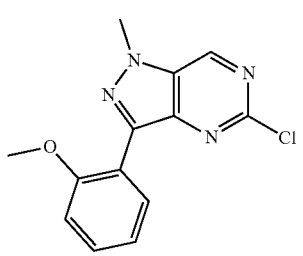
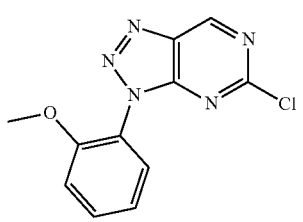
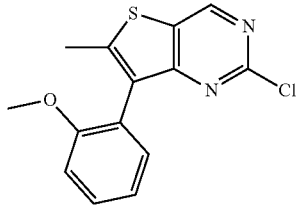
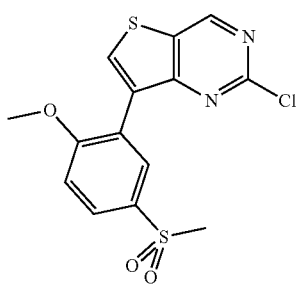
-continued
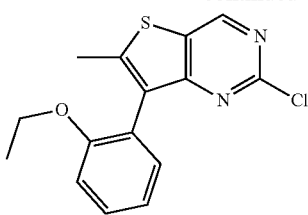
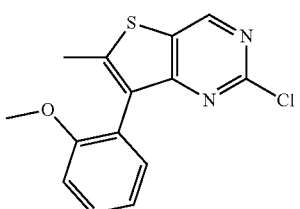
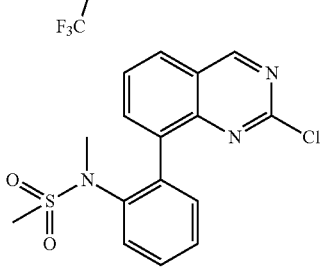
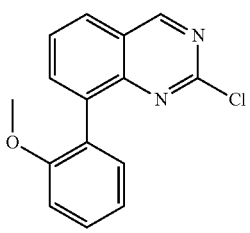
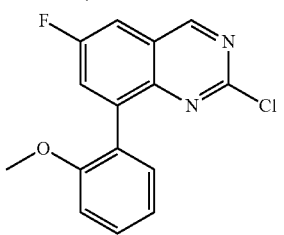
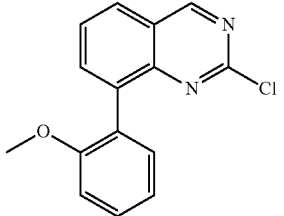
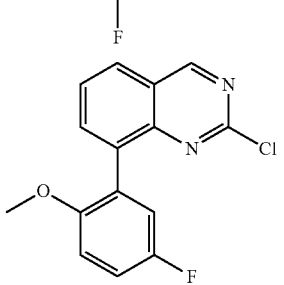

-continued

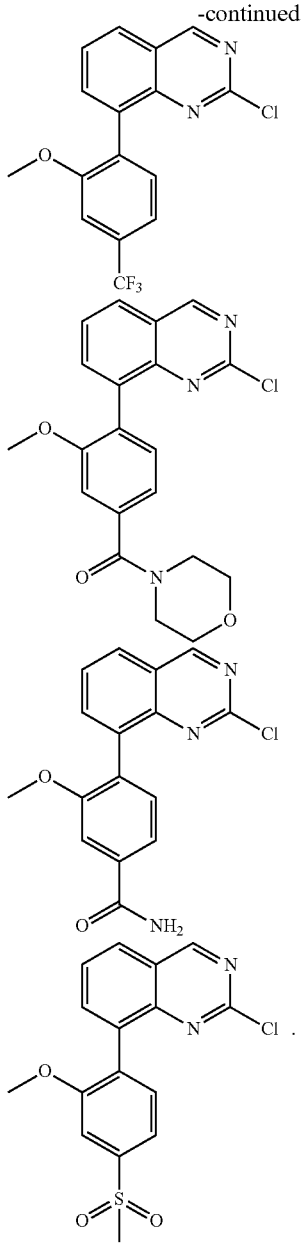

The present invention also provides a process for preparing the compound having the structure of formula I-a, the steps and the reaction conditions are as described above.

The present invention also provides a use of the condensed-ring pyrimidylamino derivative, the tautomer, the enantiomer, the diastereoisomer thereof, the pharmaceutically acceptable salt, the metabolite, the metabolic precursor or the prodrug thereof in manufacturing a medicament for preventing, relieving and/or treating cancer and/or related diseases caused by the anaplastic lymphoma kinase.

The cancer generally includes lung cancer, esophageal cancer, gastric cancer, colorectal cancer, liver cancer, nasopharyngeal carcinoma, brain tumor, breast cancer, cervical cancer, blood cancer, bone cancer and the like.

The related diseases caused by the anaplastic lymphoma kinase generally include tumors or psychiatric disorders.

The present invention also provides a pharmaceutical composition, which comprises a therapeutically effective amount of a compound selected from the group consisting of the condensed-ring pyrimidylamino derivative, the tautomer, the mesomer, the racemate, the stereoisomer thereof, the pharmaceutically acceptable salt, the metabolite, the metabolic precursor and the prodrug thereof, and a pharmaceutically acceptable carrier and/or a diluter.

In the present invention, the pharmaceutical composition may be formulated into various types of dosage forms such as tablets, pills, powders, liquids, suspensions, emulsions, granules, capsules, suppositories and injections (solutions and suspensions,) etc., preferably liquids, suspensions, emulsions, suppositories and injections (solutions and suspensions) etc.

In order to form a pharmaceutical composition in the form of a tablet, any known and widely used excipients in the art may be used. For example, carriers such as lactose, sugar, sodium chloride, glucose, urea, starch, calcium carbonate, kaolin, crystalline cellulose and silicic acid and the like; adhesives such as water, ethanol, propanol, common syrup, dextrose solution, starch solution, gelatin solution, carboxymethylcellulose, shellac, methylcellulose and potassium phosphate, polyvinylpyrrolidone and the like; disintegrating agents such as dry starch, sodium alginate, agar powder and kelp powder, sodium bicarbonate, calcium carbonate, polyethylene sorbitan fatty acid ester, sodium dodecyl sulfate, stearic acid monoglyceride, starch and lactose and the like; disintegrating inhibitors such as sugar, glyceryl tristearate, coconut oil and hydrogenated oil; adsorption enhancer such as quaternary ammonium base and sodium dodecyl sulfate; wetting agents such as glycerol, starch and the like; adsorbents such as starch, lactose, kaolin, bentonite and colloidal silicic acid and the like; and lubricants such as pure talc, stearate, boric acid powder and polyethylene glycol. It is also possible to use conventional coating materials to prepare sugar-coated tablets, gelatin membrane-coated tablets, enteric-coated tablets, film-coated tablets, bilayer tablets and multilayered tablets.

In order to form the pharmaceutical composition in the form of a pill, any known and widely used excipients in the art, for example, carriers such as lactose, starch, coconut oil, hardened vegetable oil, kaolin and talc and the like, adhesives such as gum arabic, gum tragacanth, gelatin and ethanol and the like; disintegrating agents such as agar and kelp powder and the like.

In order to form the pharmaceutical composition in the form of a suppository, any of the known and widely used excipients in the art may be used, for example, polyethylene glycol, coconut oil, higher alcohols, esters of higher alcohols, gelatin and semi-synthetic glycerides, etc.

In order to prepare a pharmaceutical composition in the form of an injection, the solution or suspension may be sterilized (preferably by adding an appropriate amount of sodium chloride, glucose or glycerol, etc.) to form an injection with the isotonic pressure of the blood. Any suitable carrier in the art may also be used in the preparation of the injection. For example, water, ethanol, propanediol, ethoxylated isostearyl alcohol, polyoxylated isostearyl alcohol and polyethylene sorbitan fatty acid ester. In addition, ordinary solubilizers, buffers and analgesics may be added.

In the pharmaceutical composition, the diluent may be a conventional diluent in the art.

The pharmaceutical composition may be in the form of oral or a sterile injectable aqueous solution and may be prepared according to any method known in the art for preparing a pharmaceutical composition.

The pharmaceutical composition may be used alone or in combination with one or more other agents having antitumor activity.

Unless otherwise specified, the following terms appearing in the present invention have the meaning as follows:

"Alkyl" used herein (including used alone and contained in other groups) refers to a saturated linear and branched aliphatic hydrocarbyl containing 1-20 carbon atoms, preferably containing 1-10 carbon atoms, more preferably containing 1-8 carbon atoms, such as methyl, ethyl, n-propyl, iso-propyl, n-butyl, tert-butyl, iso-butyl, pentyl, hexyl, heptyl, octyl, nonyl, decyl, 4,4-dimethylpentyl, 2,2,4-trimethylpentyl, undecyl, dodecyl, and isomers thereof.

The term "cycloalkyl" (including used alone and contained in other groups) includes saturated or partially unsaturated (containing 1 or 2 double bonds) cyclic hydrocarbon group containing 1-3 rings, including monocycloalkyl, bicycloalkyl and tricycloalkyl which contains 3-20 carbon atoms which can form a ring, preferably contains 3-10 carbon atoms, e.g. cyclopropyl, cyclobutyl, cyclopentyl, cyclohexyl, cycloheptyl, cyclooctyl, cyclodecyl and cyclododecyl, cyclohexenyl The term "alkoxy" refers to a cyclic or non-cyclic alkyl having indicated number of carbon atoms linked by an oxygen bridge. Therefore, "alkoxy" includes the definitions of the alkyl and the cycloalkyl.

The term "halogen" used herein refers to F, Cl, Br, I or At.

The term "hydroxyl" used herein refers to

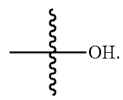 [SMILES: *O]

The term "amino" used herein refers to

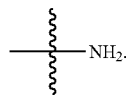

The term "sulfonyl" used herein refers to

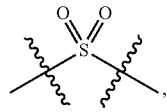

one end of which is attached to the parent and the other end to other conventional substituents, which typically including alkyl, etc., such as methanesulfonyl.

The term "acyl" used herein refers to

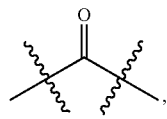 [SMILES: *C(*)=O]

a monovalent radical remaining after removing the hydroxyl from an organic or inorganic oxygenic acid, one end of which is attached to the parent and the other end to other conventional substituents, which typically including alkyl, etc., such as formyl.

The term "amido" used herein refers to

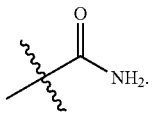

The term "heteroaryl" used herein refers to a stable monocyclic or bicyclic ring with up to 7 atoms in each ring, and at least one of the ring(s) is an aromatic ring containing 1-4 heteroatoms selected from the group consisting of O, N and S. The heteroaryl defined herein includes but not limited to acridinyl, carbazolyl, cinnolinyl, quinoxalinyl, pyrazolyl, indolyl, benzotriazolyl, furanyl, thienyl, benzothienyl, benzofuranyl, quinolinyl, isoquinolyl, oxazolyl, isoxazolyl, indolyl, pyrazinyl, pyridazinyl, pyridyl, pyrimidyl, pyrryl, tetrahydroquinoline. As defined for the following heterocyclic ring, "heteroaryl" can also be understood including the N-oxide derivative of any N-containing heteroaryl. Where the heteroaryl substituent is a bicyclic substituent and one of the rings is a non-aromatic ring or without any heteroatom, it can be understood that the linkage is carried out by the aromatic ring or the ring containing the heteroatom(s).

The term "carbon heterocyclic ring", "heterocyclic ring" or "heterocyclic group" used herein refers to a 5-10 membered aromatic or non-aromatic heterocyclic ring having 1-4 of heteroatoms selected from the group consisting of O, N and S, including bicyclic group. Therefore, "heterocyclic group" includes the heteroaryl and the dihydro- or tetrahydro-analogues thereof. The examples of the "heterocyclic group" include but not limited to benzimidazolyl, benzofuranyl, benzofurazinyl, benzopyrazolyl, benzotriazolyl, benzothienyl, benzoxazolyl, carbazyl, carbazolyl, cinnolinyl, furanyl, imidazolyl, indolinyl, indolyl, indazolyl, isobenzofuranyl, pseudoindolyl, isoquinolyl, isothiazolyl, isoxazolyl, naphthalene pyrimidinyl, oxadiazolyl, oxazolyl, oxazoline, isoxazoline, oxycyclobutyl, pyranyl, pyrazinyl, pyrazolyl, pyridazinyl, pyridopyridyl, pyridazinyl, pyridyl, pyrimidyl, pyrryl, quinazolyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridyl, dihydropyrimidinyl, dihydropyryl, dihydroquinolyl, dihydrotetrazolyl, dihydrothiadiazolyl, dihydrothiazolyl, dihydrothienyl, dihydrotriazolyl, dihydro-azetidinyl, methylenedioxybenzoyl, tetrahydrofuranyl, tetrahydrothienyl and N-oxide thereof.

The term "heterocycloalkyl" used herein alone or as a part of other groups refers to a saturated or partially unsaturated 4-12 membered ring having 1-4 of heteroatoms (e.g. N, O and/or S). Besides, any heterocycloalkyl can fuse to a cycloalkyl, an aryl, a heteroaryl or a heterocycloalkyl.

The term "aromatic ring" used herein refers to any stable monocyclic or bicyclic carbon rings with up to 7 atoms in each ring and at least one of the rings is an aromatic ring. The examples of the aromatic unit include phenyl, naphthyl, tetrahydronaphthyl, 2, 3-dihydro indenyl, biphenyl, phenanthryl, anthryl or acenaphthyl. It can be understood that when the aryl is a bicyclic group and one of the ring is a non-aromatic ring, the linkage is carried out by the "aromatic ring".

The term "heteroaromatic ring" used herein refers to a stable monocyclic or bicyclic ring with up to 7 atoms in each ring and at least one of the ring is an aromatic ring having 1-4 of heteroatoms selected from the group consisting of O, N and S. In this definition, the heteroaryl includes but not limited to acridine, carbazole, cinnoline, carboline, quinoxaline, imidazole, pyrazole, pyrrole, indole, indoline, benzotriazole, benzimidazole, furan, thiophen, isothiazole, benzothiophene, dihydrobenzothiophene, benzofuran, isobenzofuran, benzoxazole, benzofuraxan, benzopyrazole, quinoline, isoindoline, isoquinoline, oxazole, oxadiazole, isoxazole, indole, pyrazine, pyridopyridine, tetrazolopyridine, pyridazine, pyridine, naphthalene pyrimidine, pyrimidine, pyrrole, tetrazole, thiadiazole, thiazole, thiophene, triazole, quinazoline, tetrahydroquinoline, dihydrobenzimidazole, dihydrobenzofuran, dihydrobenzoxazole, dihydroquinoline. As defined for the following heterocyclic rings, "heteroaromatic ring" is also understood to include N-oxide derivatives of any N-containing heteroaryl. Where the heteroaryl substituent is a bicyclic substituent and one of the rings is a non-aromatic ring or without any heteroatom, it can be understood that the linkage is carried out by the aromatic ring or the ring containing the heteroatom(s).

The term "therapeutically effective amount" refers to an amount of the compound administered to a subject sufficient to treat the diseases involved in the present invention. Though the therapeutically effective amount of the compound will vary depending on the compound, the condition and its severity, and the age of the subject to be treated, it can be determined by a person skilled in the art according to the common method.

As used in the present invention, when the specific salt, pharmaceutical composition, composition, excipient are mentioned to be "pharmaceutically acceptable", it means that the salt, pharmaceutical composition, composition, excipient are generally non-toxic, safe and suitable to be administered to the subject; the subject is preferably a mammal, more preferably human.

The term "pharmaceutically acceptable salt" as used herein refers to a pharmaceutically acceptable organic or inorganic salt of the compound of the present invention. Typical examples are include but not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisate, fumarate, gluconate, glucuronate, saccharate, formate, benzoate, glutamate, methylsulfonate, ethylsulfonate, benzene sulfonate, tosilate, embonate (i.e. 1-1-methylene-bis(2-hydroxyl-3-naphthoate)).

The term "prodrug" used herein refers to a derivative of a compound containing biological reactive functional groups, which can be cleaved from the compound or react in other ways to provide the compound under biological condition (in vivo or in vitro). Generally, the prodrug does not have activity, or have less activity than the compound itself, this makes the compound exhibit effects until the biological reactive functional group cleaved from the compound. The biological reactive functional group can hydrolyze or oxidize under biological condition to provide the compound. For example, the prodrug can include biologically hydrolysable groups. The biologically hydrolysable groups include but not limited to a biologically hydrolysable phosphate, a biologically hydrolysable ester, a biologically hydrolysable amide, a biologically hydrolysable carbonate, a biologically hydrolysable carbamate and a biologically hydrolysable ureide.

The compound of the present invention can contain one or more asymmetric centers ("stereoisomers"). As used herein, the term "stereoisomer" refers to Cis- and Trans-isomer, R- and S-enantiomer and diastereomer. These stereoisomers can be prepared by methods of asymmetric synthesis or chiral separation (e.g. separation, crystallization, thin layer chromatography, column chromatography, gas chromatography, high performance liquid chromatography). These stereoisomers may also be derived from a diastereomer obtained by reacting a mixture of the enantiomers or racemates with a proper chiral compound, followed by crystallizing or any other proper common method.

As used herein, the term "subject" refers to any animal to be administered or has been administered with the compound or the pharmaceutical composition according to the example of the present invention, preferably a mammal, most preferably human. As used herein, the term "mammal" includes any mammal. Typical mammal includes but not limited to cattle, horse, sheep, pig, cat, dog, mouse, rat, rabbit, Guinea pig, monkey, human and so on, the most preferable human.

In one embodiment, "treat" or "treating" refers to an improvement, prevention or reversion of a disease or a condition or at least one distinguished symptom thereof. In another example, "treat" or "treating" refers to an improvement, prevention or reversion of at least one of measurable body parameters of a disease or a condition which is being treated, which may not been distinguished in a mammal. However, in another example, "treat" or "treating" refers to slowing the development of a disease or a condition, or refers to stabilizing in body, such as a recognizable symptom, or refers to stabilizing in physiology, such as body parameters, or refers to both. In another embodiment, treat" or "treating" refers to slowing the initiation of a disease or a condition.

In certain embodiments, the compound of the present invention is administered for prevention. As used herein, "prevent" or "preventing" refers to lowering a risk of having a disease or a condition. In a preferred example, administering an indicated compound to a subject for a preventive purpose, such as the subject having a tendency to catch or having a family history of cancer or autoimmune diseases.

Without departing from the common knowledge in the art, the optimized examples can be obtained by optionally combining the preferred conditions above.

The reagents and raw materials are commercially available.

The positive effects achieved by the present invention lie in that: the condensed-ring pyrimidylamino derivative of the present invention has a significant inhibitory effect on anaplastic lymphoma kinase (ALK) and can effectively relieve or treat cancer and other related diseases.

DETAILED DESCRIPTION OF THE PREFERRED EXAMPLE

The following examples further illustrate the present invention, but the present invention is not limited thereto. The experimental method without particular conditions being specified in the following examples is chosen according to conventional methods and conditions, or product instructions.

The structure of the compound of the present invention is determined by NMR or MS, NMR is obtained by Bruker Avance-500 apparatus, d₆-DMSO, CDCl₃ and CD₃OD etc. as a solvent, TMS as an interior label. MS is obtained by LC-MS Agilent Technologies 6110, ESI as an ion source.

Microwave reaction is conducted in Explorer full automatic microwave irradiation equipment supplied by CEM, US Corporation, magnetron frequency is 2450 MHz, continuous microwave output power is 300 W.

The instrument used for preparative high performance liquid chromatography is Gilson 281, the preparative column is Xbridge, 21.2×250 mm C18, 10 μm.

Example 1

N-(2-(2-((2-Methoxy-4-(piperidin-4-yl)phenyl)amino)thieno[3,2-d]pyrimidin-7-yl)phenyl)-N-methylmethanesulfonamide (Compound 1)

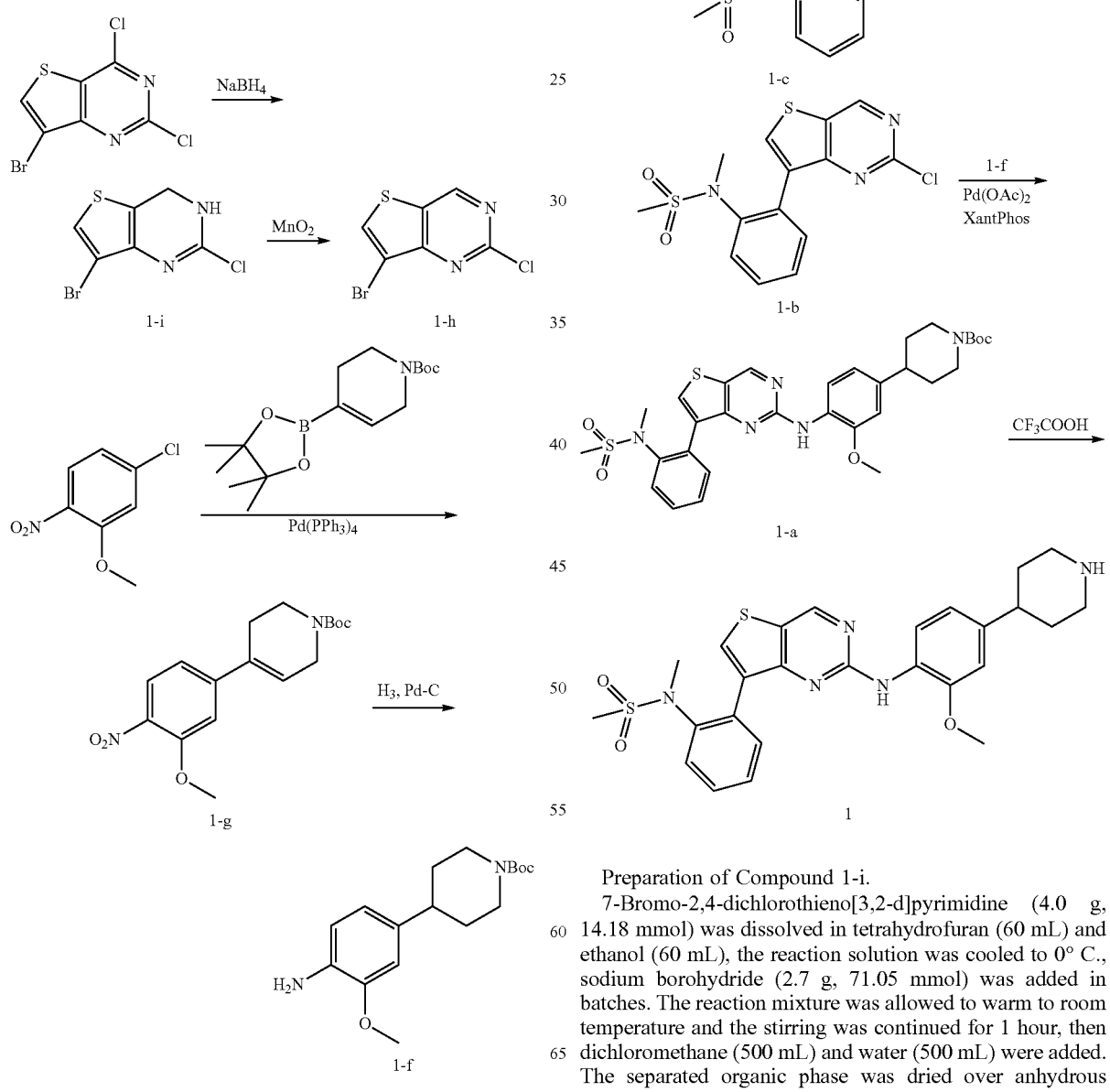

Preparation of Compound 1-i.

7-Bromo-2,4-dichlorothieno[3,2-d]pyrimidine (4.0 g, 14.18 mmol) was dissolved in tetrahydrofuran (60 mL) and ethanol (60 mL), the reaction solution was cooled to 0° C., sodium borohydride (2.7 g, 71.05 mmol) was added in batches. The reaction mixture was allowed to warm to room temperature and the stirring was continued for 1 hour, then dichloromethane (500 mL) and water (500 mL) were added. The separated organic phase was dried over anhydrous sodium sulfate, filtered, and the filtrate was concentrated under reduced pressure to deliver a yellow solid 1-i (2.5 g, yield: 71%). This product was used without further purification. LC-MS (ESI): m/z=251 [M+H]$^+$.

Preparation of Compound 1-h.

Compound 1-i (500 mg, 2.02 mmol) was dissolved in dichloromethane (5 mL), activated manganese dioxide (270 mg, 3.04 mmol) was added and the mixture was stirred at room temperature for 3 hours. The reaction mixture was filtered through diatomite and the filter cake was washed with dichloromethane (5 mL×4). The combined filtrates were concentrated under reduced pressure to deliver a white solid 1-h (430 mg, yield: 86%), this product was used without further purification. LC-MS (ESI): m/z=249 [M+H]$^+$.

Preparation of Compound 1-g.

4-Nitrochlorobenzene (4.9 g, 25.9 mmol), N-Boc-1,2,3,6-tetrahydropyridine-4-boronic acid pinacol ester (8.0 g, 25.9 mmol), potassium carbonate (8.28 g, 60 mmol) and tetrakis (triphenylphosphine) palladium (1.5 g, 1.3 mmol) were dissolved in dioxane (40 mL) and water (10 mL). The reaction mixture was replaced with nitrogen three times to remove the oxygen inside the system and then heated at 80° C. for 16 hours. The reaction mixture was cooled to room temperature, filtered through diatomite, and the filter cake was washed with ethyl acetate (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=10:1) to deliver a yellow solid 1-g (8.5 g, yield: 97%).

$^1$H-NMR (400 MHz, CDCl$_3$) δ: 7.87 (d, J=8.6 Hz, 1H), 7.01 (m, 2H), 6.17 (s, 1H), 4.12 (m, 2H), 3.98 (s, 3H), 3.66 (m, 2H), 2.53 (m, 2H), 1.50 (s, 9H) ppm.

Preparation of Compound 1-f.

Compound 1-g (6.68 g, 20 mmol) and 10% palladium-carbon (1.2 g) were dissolved in methanol (10 mL). The reaction mixture was replaced with hydrogen three times and then hydrogenated at 40° C. for 3 hours. The reaction mixture was filtered to remove palladium-carbon and the filtrate was concentrated under reduced pressure to deliver a pink solid 1-f (6.7 g, yield: 100%), the product was used without further purification. LC-MS (ESI): m/z=281 [M+H-t-Bu]$^+$.

Preparation of Compound 1-e.

2-Bromoaniline (10.0 g, 58.5 mmol) was dissolved in pyridine (50 mL) and acetonitrile (50 mL). The reaction solution was cooled to 0° C. and methanesulfonyl chloride (10.0 g, 87.7 mmol) was added dropwise. The reaction mixture was allowed to warm to room temperature and the stirring was continued for 30 minutes and then concentrated under reduced pressure. The residue was dissolved in ethyl acetate (250 mL) and diluted with water (250 mL). The pH of the separated organic phase was adjusted to 7 with 1 M aqueous hydrochloric acid solution. The organic phase was dried over anhydrous sodium sulfate, filtered, and the filtrate was concentrated under reduced pressure to deliver a yellow solid 1-e (14 g, yield: 96%). This product was used without further purification. LC-MS (ESI): m/z=250 [M+H]$^+$.

Preparation of Compound 1-d.

Compound 1-e (5.0 g, 20.08 mmol) was dissolved in acetone (100 mL), anhydrous potassium carbonate (4.2 g, 30.12 mmol) was added, methyl iodide (4.3 g, 30.12 mmol) was slowly added and the mixture was stirred at room temperature for 16 hours. The reaction mixture was filtered and the filter cake was washed with acetone (100 mL) and the combined filtrates were concentrated under reduced pressure. The residue was dissolved in ethyl acetate (150 mL) and diluted with water (100 mL). The separated organic phase was dried over anhydrous sodium sulfate and filtered. The filtrate was concentrated under reduced pressure to deliver a pale yellow solid 1-d (3.1 g, yield: 59%), this product was used without further purification. LC-MS (ESI): m/z=264 [M+H]+.

Preparation of Compound 1-c.

Compound 1-d (4.0 g, 15.21 mmol), bis(pinacolato)diboron (5.6 g, 22.05 mmol), and anhydrous potassium acetate (4.5 g, 45.9 mmol) were suspended in dioxane (60 mL) and then [1,1'-bis(diphenylphosphino)ferrocene]dichloropalladium(II) (1.2 g, 1.52 mmol) was added. The reaction mixture was replaced with nitrogen three times to remove the oxygen inside the system and then heated at 80° C. for 16 hours. The reaction mixture was cooled to room temperature, diluted with ice water (100 mL) and extracted with ethyl acetate (50 mL×3). The combined organic phases were washed successively with water (50 mL×3) and brine (50 mL), dried over anhydrous sodium sulfate, filtered, and the filtrate was concentrated under reduced pressure. The residue was purified by silica gel column chromatography (petroleum ether:ethyl acetate=5:1) to deliver a pale yellow oil 1-c (3.4 g, yield: 72%). LC-MS (ESI): m/z=312 [M+H]$^+$.

Preparation of Compound 1-b.

Compound 1-c (1.05 g, 3.38 mmol), compound 1-h (840 mg, 3.38 mmol), [1,1'-bis(diphenylphosphino)ferrocene]dichloropalladium(II) (316 mg, 0.38 mmol) and sodium carbonate (1.05 g, 9.92 mmol) were dissolved in 1,4-dioxane (11 mL) and water (11 mL). The reaction mixture was replaced with nitrogen three times to remove the oxygen inside the system and then heated at 90° C. for 30 minutes. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (dichloromethane:methanol=100:1) to deliver a light brown solid 1-b (610 mg, yield: 51%). LC-MS (ESI): m/z=354 [M+H]$^+$.

Preparation of Compound 1-a.

Compound 1-b (180 mg, 0.51 mmol), compound 1-f (214 mg, 0.70 mmol), palladium acetate (189 mg, 0.85 mmol), cesium carbonate (495 mg, 1.52 mmol) and 4,5-bis(diphenylphosphino)-9,9-dimethylxanthene (545 mg, 0.95 mmol) were dissolved in dioxane (5 mL). The reaction mixture was replaced with nitrogen three times to remove the oxygen inside the system and then heated at 110° C. for 16 hours. The reaction was cooled to room temperature and the reaction mixture was filtered through diatomite. The filter cake was washed with dichloromethane (50 mL×3) and the combined filtrates were concentrated under reduced pressure. The residue was purified by silica gel thin layer chromatography preparative plate (petroleum ether:ethyl acetate=1:1) to deliver a pale yellow solid 1-a (102 mg, yield: 33%). LC-MS (ESI): m/z=624 [M+H]$^+$.

Preparation of Compound 1.

Compound 1-a (102 mg, 0.16 mmol) was dissolved in dichloromethane (2 mL). The reaction solution was cooled to 0° C., trifluoroacetic acid (2 mL) was added, and the reaction was stirred at room temperature for 16 hours. The reaction was concentrated under reduced pressure and the residue was diluted with water (30 mL). The pH was adjusted to 10 with saturated sodium carbonate solution. The aqueous phase was extracted with dichloromethane (50 mL×3). The combined organic phases were washed with water (20 mL×3 mL) and brine (20 mL), dried over anhydrous sodium sulfate, filtered, and the filtrate was concentrated under reduced pressure. The residue was purified by preparative high performance liquid chromatography (mobile phase: 10 mM ammonium bicarbonate aqueous solution:acetonitrile=30%-60%) to deliver a pale yellow solid 1 (35 mg, yield: 41%). LC-MS (ESI): m/z=524 [M+H]$^+$.

$^1$H-NMR (400 MHz, CDCl$_3$) δ: 7.88 (s, 1H), 7.69 (s, 1H), 7.28-7.43 (m, 1H), 4.31-4.39 (m, 1H), 3.81 (s, 2H), 3.64 (s, 2H), 3.20-3.24 (m, 2H), 2.76-2.86 (m, 6H), 2.11-2.14 (m, 2H), 1.92-1.99 (m, 2H) ppm.

Example 2

N-(2-(2-((2-Methoxy-4-(piperidin-4-yl)phenyl) amino)-6-methylthieno[3,2-d]pyrimidin-7-yl)phenyl)-N-methylmethanesulfonamide (Compound 2)

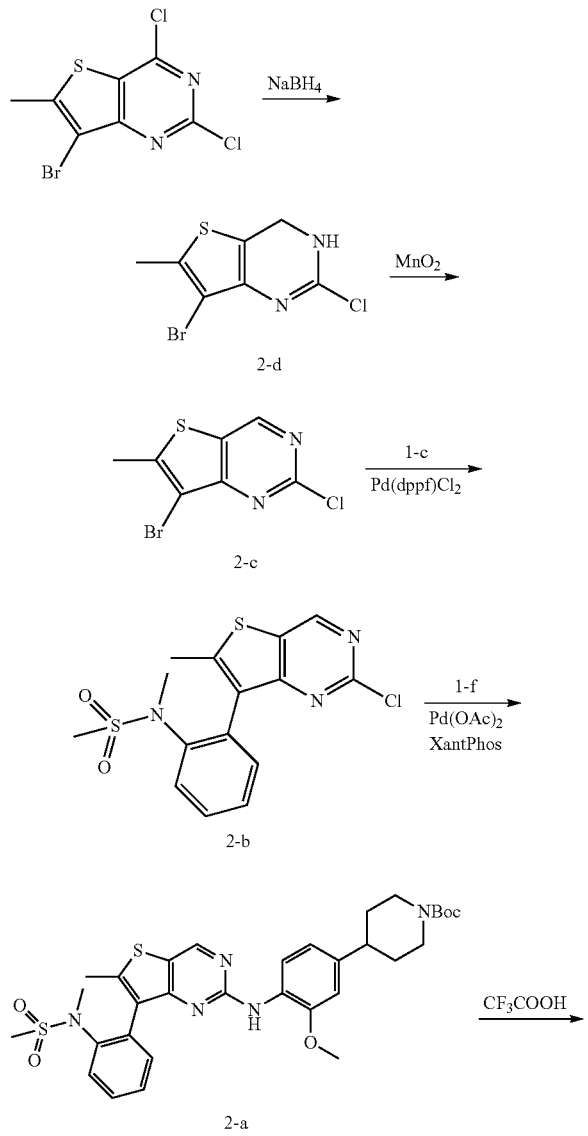

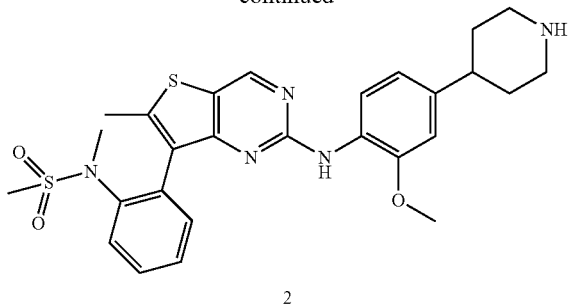

Preparation of Compound 2-d.

7-Bromo-2,4-dichloro-6-methylthioeno[3,2-d]pyrimidine (5.0 g, 16.89 mmol) was dissolved in tetrahydrofuran (50 mL) and ethanol (50 mL). The reaction solution was cooled to 0° C. and sodium borohydride (3.19 g, 84.5 mmol) was added in batches. The reaction mixture was allowed to warm to room temperature and the stirring was continued for 3 hours. Water (500 mL) was then added and extracted with dichloromethane (300 mL×3). The combined organic phases were dried over anhydrous sodium sulfate, filtered and the filtrate was concentrated under reduced pressure to deliver a yellow liquid 2-d (4 g, yield: 90%). This product was used without further purification. LC-MS (ESI): m/z=265 [M+H]$^+$.

Preparation of Compound 2-c.

Compound 2-d (4.0 g, 15.15 mmol) was dissolved in dichloromethane (100 mL), activated manganese dioxide (6.6 g, 75.8 mmol) was added and stirred at room temperature for 16 hours. The reaction mixture was filtered through diatomite and the filter cake was washed with dichloromethane (50 mL×5). The combined filtrates were concentrated under reduced pressure to deliver a yellow solid 2-c (3.8 g, yield: 96%), this product was used without further purification. LC-MS (ESI): m/z=263 [M+H]$^+$.

Preparation of Compound 2-b.

Compound 2-c (400 mg, 1.53 mmol), compound 1-h (474 mg, 1.53 mmol), [1,1'-bis(diphenylphosphino)ferrocene]dichloropalladium(II) (132 mg, 0.16 mmol) and sodium carbonate (486 mg, 4.58 mmol) were dissolved in 1,4-dioxane (2 mL) and water (2 mL). The reaction mixture was replaced with nitrogen three times to remove the oxygen inside the system and then heated at 90° C. for 30 minutes. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (dichloromethane:methanol=1:1) to deliver a yellow solid 2-b (170 mg, yield: 31%). LC-MS (ESI): m/z=368 (M+H)$^+$.

Preparation of Compound 2-a.

Compounds 2-b (150 mg, 0.41 mmol), compound 1-f (188 mg, 0.61 mmol), palladium acetate (150 mg, 0.67 mmol), cesium carbonate (405 mg, 1.24 mmol) and 4,5-bis(diphenylphosphino)-9,9-dimethylxanthene (480 mg, 0.83 mmol) were dissolved in dioxane (3 mL). The reaction mixture was replaced with nitrogen three times to remove the oxygen from the system and then heated at 110° C. for 40 minutes. The reaction was cooled to room temperature and the reaction mixture was filtered through diatomite. The filter cake was washed with dichloromethane (50 mL×3) and the combined filtrates were concentrated under reduced pressure. The residue was purified by silica gel thin layer chromatography preparative plate (ethyl acetate as developing solvent) to deliver a pale yellow solid 2-a (75 mg, yield: 28%). LC-MS (ESI): m/z=638 [M+H]$^+$.

Preparation of Compound 2.

Compound 2-a (50 mg, 0.08 mmol) was dissolved in dichloromethane (3 mL). The reaction solution was cooled to 0° C., trifluoroacetic acid (3 mL) was added, and the reaction mixture was stirred at room temperature for 2 hours. The reaction mixture was concentrated under reduced pressure and the residue was diluted with water (30 mL). The pH was adjusted to 10 with saturated sodium carbonate solution. The aqueous phase was extracted with dichloromethane (50 mL×3). The combined organic phases were washed with water (20 mL×3 mL) and brine (20 mL), dried over anhydrous sodium sulfate, filtered and the filtrate was concentrated under reduced pressure. The residue was purified by preparative high performance liquid chromatography (mobile phase: 10 mM ammonium bicarbonate aqueous solution:acetonitrile=40%-70%) to deliver a pale yellow solid 2 (15 mg, yield: 36%). LC-MS (ESI): m/z=538 [M+H]$^+$.

$^1$H-NMR (400 MHz, CDCl$_3$) δ: 8.78 (s, 1H), 8.21 (d, J=8 Hz, 1H), 7.65 (d, J=8 Hz, 1H), 7.46-7.56 (m, 3H), 7.35 (d, J=7 Hz, 1H), 6.71 (s, 1H), 6.61-6.63 (d, J=8 Hz, 1H), 3.85 (s, 3H), 3.17-3.20 (m, 2H), 3.11 (s, 3H), 2.69-2.75 (m, 2H), 2.53 (m, 1H), 2.52 (s, 3H), 2.49 (s, 3H), 1.78-1.90 (m, 2H), 1.61-1.64 (m, 2H) ppm.

Example 3

7-(2,3-Dihydro-1-benzofuran-7-yl)-N-(2-methoxy-4-(piperidin-4-yl)phenyl)-6-methylthieno[3,2-d]pyrimidin-2-amine (Compound 3)

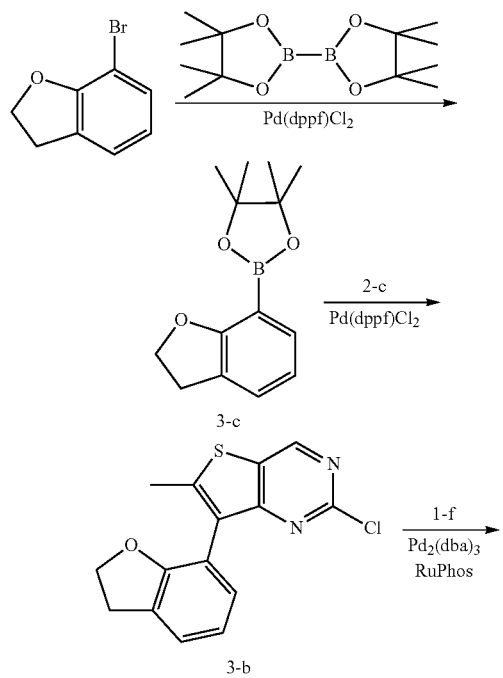

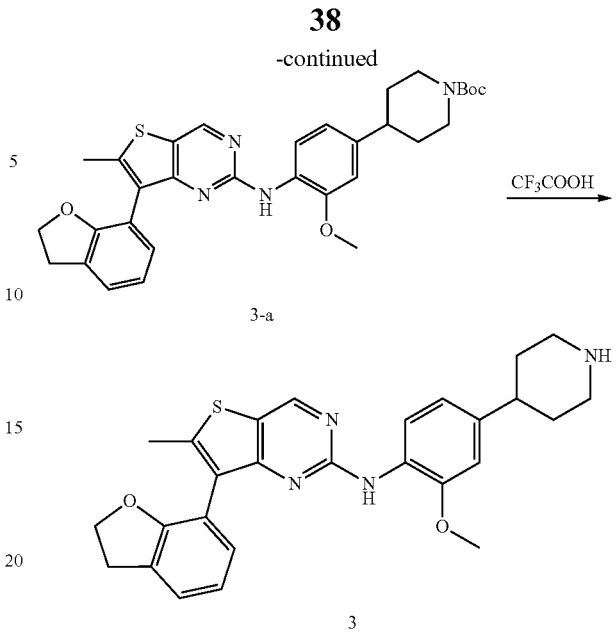

Preparation of Compound 3-c.

Compound 7-bromobenzodihydrofuran (0.4 g, 2 mmol), bis(pinacolato)diboron (0.78 g, 3 mmol) and anhydrous potassium acetate (0.4 g, 4 mmol) were suspended in dimethyl sulfoxide (5 mL) and then [1,1'-bis(diphenylphosphino)ferrocene]dichloropalladium(II) (0.16 g, 0.2 mmol) was added. The reaction mixture was replaced with nitrogen three times to remove the oxygen inside the system and then heated at 80° C. for 8 hours. The reaction was cooled to room temperature, diluted with ice water (100 mL) and extracted with ethyl acetate (50 mL×3). The combined organic phases were washed successively with water (50 mL×3) and brine (50 mL), dried over anhydrous sodium sulfate, filtered, and the filtrate was concentrated under reduced pressure. The residue was purified by silica gel column chromatography (petroleum ether:ethyl acetate=30:1) to deliver compound 3-c (0.29 g, yield: 56%).

$^1$H-NMR (400 MHz, CDCl$_3$) δ: 7.53 (d, J=8 Hz, 1H), 7.27 (d, J=8 Hz, 1H), 6.83 (t, J=8 Hz, 1H), 4.63 (t, J=8.8 Hz, 1H), 3.16 (t, J=8.8 Hz, 1H), 1.36 (s, 12H) ppm.

Preparation of Compound 3-b.

Compounds 3-c (200 mg, 0.8 mmol), compound 2-c (264 mg, 1.0 mmol), [1,1'-bis(diphenylphosphino)ferrocene]dichloropalladium(II) (73 mg, 0.1 mmol) and sodium carbonate (210 mg, 2 mmol) were dissolved in 1,4-dioxane (8 mL) and water (2 mL). The reaction mixture was replaced with nitrogen three times to remove the oxygen inside the system and then heated at 90° C. for 8 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=10:1) to deliver a yellow solid 3-b (130 mg, yield: 43%). LC-MS (ESI): m/z=304 [M+H]$^+$.

Preparation of Compound 3-a.

Compound 3-b (150 mg, 0.5 mmol), compound 1-f (180 mg, 0.6 mmol), tris(dibenzylideneacetone)dipalladium (150 mg, 0.67 mmol), potassium carbonate (180 mg, 1.29 mmol), 2-dicyclohexylphosphino-2',6'-di-iso-propoxy-1,1'-biphenyl (480 mg, 0.83 mmol) were dissolved in N,N-dimethylformamide (3 mL). The reaction mixture was replaced with nitrogen three times to remove the oxygen inside the system and then heated at 110° C. for 16 hours. The reaction was cooled to room temperature and the reaction mixture was filtered through diatomite. The filter cake was washed with dichloromethane (50 mL×3) and the combined filtrates were concentrated under reduced pressure. The residue was purified by silica gel thin layer chromatography preparative plate (petroleum ether:ethyl acetate=1:1) to deliver a pale yellow solid 3-a (89 mg, yield: 31%). LC-MS (ESI): m/z=573 [M+H]$^+$.

Preparation of Compound 3.

Compound 3-a (89 mg, 0.156 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in ethyl acetate (50 mL) and diluted with 1 M aqueous hydrochloric acid solution (50 mL). The pH of the separated aqueous phase was adjusted to 10 with a saturated potassium carbonate solution, a solid was precipitated, filtered. The filter cake was dried in vacuo to deliver a pale yellow solid 3 (26 mg, yield: 35%). LC-MS (ESI): m/z=473 [M+H]$^+$.

$^1$H-NMR (400 MHz, CD$_3$OD) δ: 8.83 (s, 1H), 8.41 (d, J=8 Hz, 1H), 7.33 (d, J=7.2 Hz, 1H), 8.25 (d, J=7.2 Hz, 1H), 7.0 (t, J=8 Hz, 1H), 6.84 (s, 1H), 6.68 (d, J=8 Hz, 1H), 4.55 (t, J=8 Hz, 2H), 3.90 (s, 3H), 3.27 (m, 2H), 2.85 (d, J=8 Hz, 2H), 2.54 (s, 3H), 1.90 (m, 2H), 1.76 (m, 2H), 1.33 (m, 4H) ppm.

Example 4

N-(2-Methoxy-4-(piperidin-4-yl)phenyl)-7-(1-methyl-1H-pyrazol-5-yl)thieno[3,2-d]pyrimidin-2-amine (Compound 4)

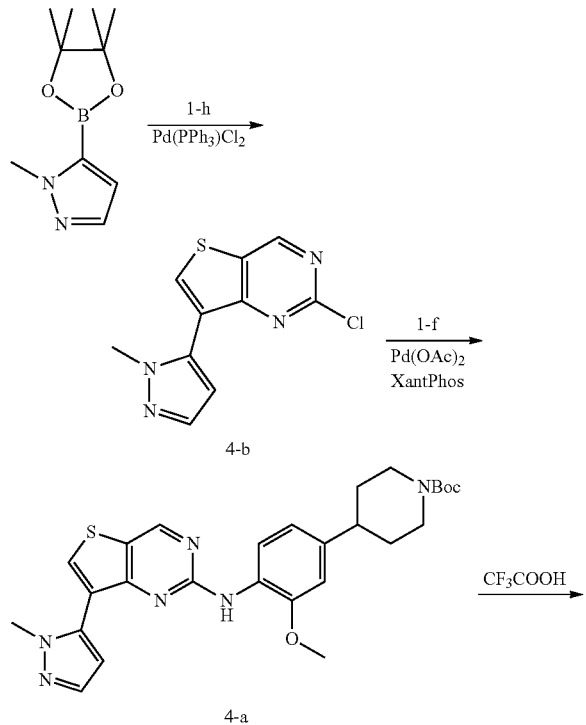

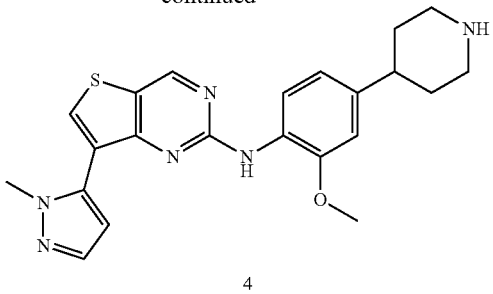

Preparation of Compound 4-b.

Compound 1-h (210 mg, 0.84 mmol), 1-methyl-pyrazole-5-boronicacidpinacolester (175 mg, 0.84 mmol), bis(triphenylphosphine)palladium(II) dichloride (3 mg, 0.05 mmol), 2-di-tert-butylphosphino-2',4',6'-triisopropylbiphenyl (33 mg, 0.08 mmol) and 2 M aqueous sodium carbonate solution (3.4 mL, 6.72 mmol) were dissolved in 1,4-dioxane (7 mL). The reaction mixture was replaced with nitrogen three times to remove the oxygen inside the system and then heated at 90° C. for 6 hours. The reaction was cooled to room temperature, diluted with ice water (100 mL) and extracted with dichloromethane (100 mL×3). The combined organic phases were washed successively with water (50 mL×3) and brine (50 mL), dried over anhydrous sodium sulfate, filtered, and the filtrate was concentrated under reduced pressure. The residue was purified by preparative high performance liquid chromatography to deliver a yellow solid 4-b (100 mg, yield: 48%). LC-MS (ESI): m/z=251 [M+H]$^+$.

Preparation of Compound 4-a.

Compound 4-b (50 mg, 0.2 mmol), compound 1-f (92 mg, 0.3 mmol), palladium acetate (5 mg, 0.02 mmol), cesium carbonate (194 mg, 0.6 mmol) and 4,5-bis(diphenylphosphino)-9,9-dimethylxanthene (23 mg, 0.04 mmol) were dissolved in dioxane (5 mL). The reaction mixture was replaced with nitrogen three times to remove the oxygen inside the system and then heated at 110° C. for 40 minutes. The reaction was cooled to room temperature and the reaction mixture was filtered through diatomite. The filter cake was washed with dichloromethane (50 mL×3) and the combined filtrates were concentrated under reduced pressure. The residue was purified by silica gel thin layer chromatography preparative plate (dichloromethane:methanol=20:1) to deliver a yellow solid 4-a (25 mg, yield: 24%). LC-MS (ESI): m/z=521 [M+H]$^+$.

Preparation of Compound 4.

Compound 4-a (25 mg, 0.05 mmol) was dissolved in dichloromethane (3 mL). The reaction solution was cooled to 0° C., trifluoroacetic acid (1 mL) was added, and the reaction mixture was stirred at room temperature for 16 hours. The reaction mixture was concentrated under reduced pressure and the residue was dissolved in dichloromethane (50 mL) and diluted with saturated sodium carbonate solution (50 mL). The separated organic phase was dried over anhydrous sodium sulfate, filtered, and the filtrate was concentrated under reduced pressure. The residue was purified by preparative high performance liquid chromatography to deliver a yellow solid 4 (35 mg, yield: 41%). LC-MS (ESI): m/z=421 [M+H]$^+$.

$^1$H-NMR (400 MHz, CDCl$_3$) δ: 8.89 (s, 1H), 8.40 (d, J=8 Hz, 1H), 7.84 (s, 1H), 7.81 (s, 1H), 7.56 (d, J=2 Hz, 1H), 7.19 (s, 1H), 6.77 (dd, J=2 Hz, J=8 Hz, 1H), 6.71 (d, J=8 Hz,

1H), 6.56 (d, J=8 Hz, 1H), 3.89 (s, 3H), 3.85 (s, 3H), 3.32 (m, 2H), 2.80 (m, 2H), 2.59 (m, 1H), 1.88 (m, 4H) ppm.

Example 5

7-(2-(Methylsulfonyl)phenyl)-N-(2-methoxy-4-(piperidin-4-yl)phenyl)-thieno[3,2-d]pyrimidin-2-amine (Compound 5)

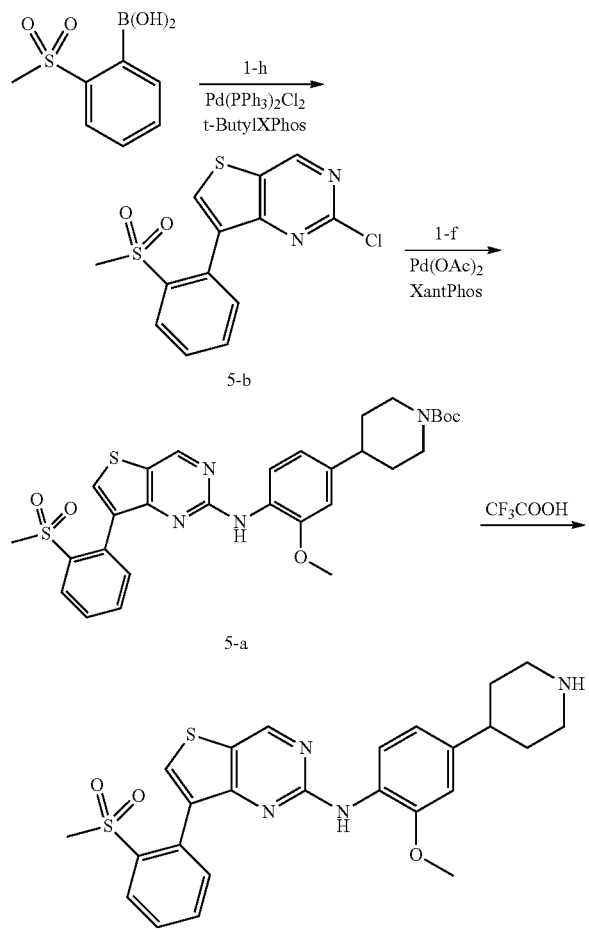

Preparation of Compound 5-b.

Compound 1-h (671 mg, 1.64 mmol), 2-(methanesulfonyl)phenylboronic acid (328 mg, 1.64 mmol), bis(triphenylphosphine)palladium(II) dichloride (69 mg, 0.09 mmol) 2-di-tert-butylphosphino-2',4',6'-triisopropylbiphenyl (63 mg, 0.15 mmol) and 2 M aqueous sodium carbonate solution (6.5 mL, 13 mmol) were dissolved in 1,4-dioxane (13 mL). The reaction mixture was replaced with nitrogen three times to remove the oxygen inside the system and then heated at 90° C. for 6 hours. The reaction was cooled to room temperature, diluted with ice water (100 mL) and extracted with dichloromethane (100 mL×3). The combined organic phases were washed successively with water (50 mL×3) and brine (50 mL), dried over anhydrous sodium sulfate, filtered, and the filtrate was concentrated under reduced pressure. The residue was purified by silica gel thin layer chromatography preparative plate (dichloromethane:methanol=40:1) to deliver a yellow solid 5-b (130 mg, yield: 24%). LC-MS (ESI): m/z=325 [M+H]$^+$.

Preparation of Compound 5-a.

Compounds 5-b (60 mg, 0.19 mmol), compound 1-f (68 mg, 0.22 mmol), cesium carbonate (180 mg, 0.56 mmol), palladium acetate (5 mg, 0.02 mmol) and 4,5-bis(diphenylphosphino)-9,9-dimethylxanthene (22 mg, 0.04 mmol) were dissolved in dioxane (5 mL). The reaction mixture was replaced with nitrogen three times to remove the oxygen inside the system and then heated at 110° C. for 40 minutes. The reaction was cooled to room temperature and the reaction mixture was filtered through diatomite. The filter cake was washed with dichloromethane (50 mL×3) and the combined filtrates were concentrated under reduced pressure. The residue was purified by silica gel thin layer chromatography preparative plate (chloromethane:methanol=25:1) to deliver a yellow solid 5-a (48 mg, yield: 43%). LC-MS (ESI): m/z=595 [M+H]$^+$.

Preparation of Compound 5.

Compound 5-a (50 mg, 0.08 mmol) was dissolved in dichloromethane (5 mL). The reaction solution was cooled to 0° C., trifluoroacetic acid (1 mL) was added, and the reaction mixture was stirred at room temperature for 2 hours. The reaction mixture was concentrated under reduced pressure and the residue was dissolved in dichloromethane (50 mL) and diluted with saturated sodium carbonate solution (50 mL). The separated organic phase was dried over anhydrous sodium sulfate, filtered, and the filtrate was concentrated under reduced pressure. The residue was purified by preparative high performance liquid chromatography to deliver a yellow solid 5 (8 mg, yield: 19%). LC-MS (ESI): m/z=495 [M+H]$^+$.

$^1$H-NMR (400 MHz, CDCl$_3$) δ: 8.98 (s, 1H), 8.30 (d, J=8 Hz, 1H), 8.25 (m, 2H), 7.77 (m, 2H), 7.70 (m, 1H), 7.63 (m, 1H), 6.74 (s, 1H), 6.62 (d, J=8 Hz, 1H), 3.89 (s, 3H), 3.35 (s, 2H), 2.83 (m, 2H), 2.61 (m, 1H), 1.83 (m, 4H) ppm.

Example 6

N-(2-Methoxy-4-(piperidin-4-yl)phenyl)-3-(2-methoxyphenyl)-1-methyl-1H-pyrazolo[4,3-d]pyrimidin-5-amine (Compound 6)

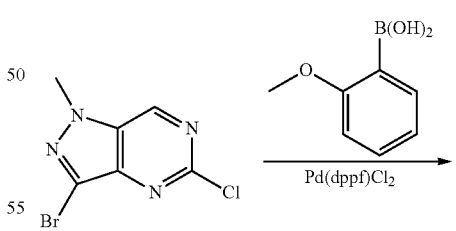

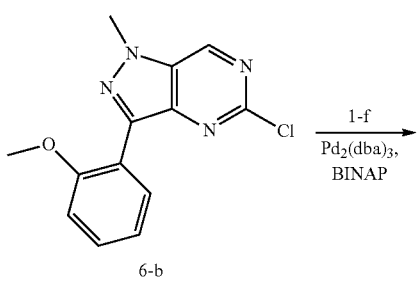

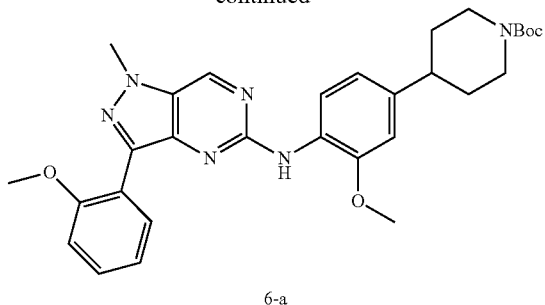

6-a

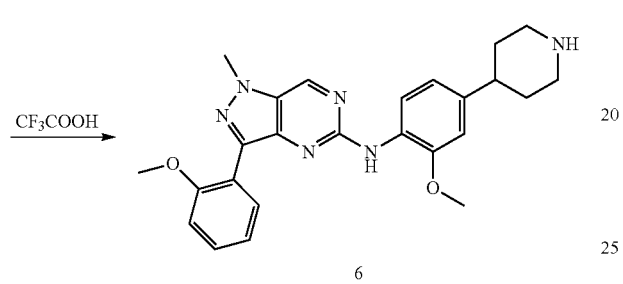

6

Preparation of Compound 6-b.

Compound 3-bromo-5-chloro-1-methyl-1H-pyrazolo[4,3-d]pyrimidine (200 mg, 0.81 mmol), o-methoxyphenylboronic acid (184 mg, 1.2 mmol), [1,1'-bis(diphenylphosphino)ferrocene]dichloropalladium(II) (59 mg, 0.08 mmol) and sodium carbonate (170 mg, 1.6 mmol) were dissolved in 1,4-dioxane (8 mL) and water (2 mL). The reaction mixture was replaced with nitrogen three times to remove the oxygen inside the system and then heated at 90° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=1:1) to deliver a white solid 6-b (90 mg, yield: 40%). LC-MS (ESI): m/z=275 [M+H]$^+$.

Preparation of Compound 6-a.

Compound 6-b (70 mg, 0.25 mmol), compound 1-f (86 mg, 0.28 mmol), cesium carbonate (122 mg, 0.37 mmol), tris(dibenzylideneacetone)dipalladium(23 mg, 0.02 mmol) and 2,2'-bis(diphenylphosphino)-1,1'-binaphthyl (16 mg, 0.02 mmol) were dissolved in toluene (10 mL). The reaction mixture was replaced with nitrogen three times to remove the oxygen inside the system, and then heated at 110° C. for 16 hours. The reaction mixture was cooled to room temperature and the reaction mixture was concentrated under reduced pressure. The residue was purified by silica gel column chromatography (dichloromethane:methanol=40:1) to deliver a yellow solid 6-a (110 mg, yield: 79%). LC-MS (ESI): m/z=545 [M+H]$^+$.

Preparation of Compound 6.

Compound 6-a (110 mg, 0.2 mmol) was dissolved in dichloromethane (3 mL). The reaction solution was cooled to 0° C., trifluoroacetic acid (1 mL) was added, and the reaction mixture was stirred at room temperature for 2 hours. The pH of the reaction mixture was adjusted to 8-9 with saturated aqueous sodium carbonate solution and then extracted with dichloromethane (10 mL×3). The combined organic phases were dried over anhydrous sodium sulfate, filtered, and the filtrate was concentrated under reduced pressure. The residue was purified by preparative high performance liquid chromatography (mobile phase: 10 mM ammonium bicarbonate aqueous solution:acetonitrile=30%-40%) to deliver a yellow solid 6 (79 mg, yield: 88%). LC-MS (ESI): m/z=445 [M+H]$^+$.

$^1$H-NMR (400 MHz, CDCl$_3$) δ: 8.81 (s, 1H), 8.69 (d, J=8.3 Hz, 1H), 7.95 (dd, J=7.5, 1.5 Hz, 1H), 7.86 (s, 1H), 7.47-7.37 (m, 1H), 7.11 (dd, J=18.0, 7.9 Hz, 2H), 6.83 (d, J=8.3 Hz, 1H), 6.77 (s, 1H), 4.16 (s, 3H), 3.91 (d, J=7.5 Hz, 6H), 3.25 (d, J=11.7 Hz, 2H), 3.06 (s, 1H), 2.77 (t, J=11.5 Hz, 2H), 2.60 (s, 1H), 1.87 (d, J=12.0 Hz, 2H), 1.72 (d, J=10.1 Hz, 2H) ppm.

Example 7

N-(2-Methoxy-4-(piperidin-4-yl)phenyl)-3-(2-methoxyphenyl)-3H-[1,2,3]triazolo[4,5-d]pyrimidin-5-amine (Compound 7)

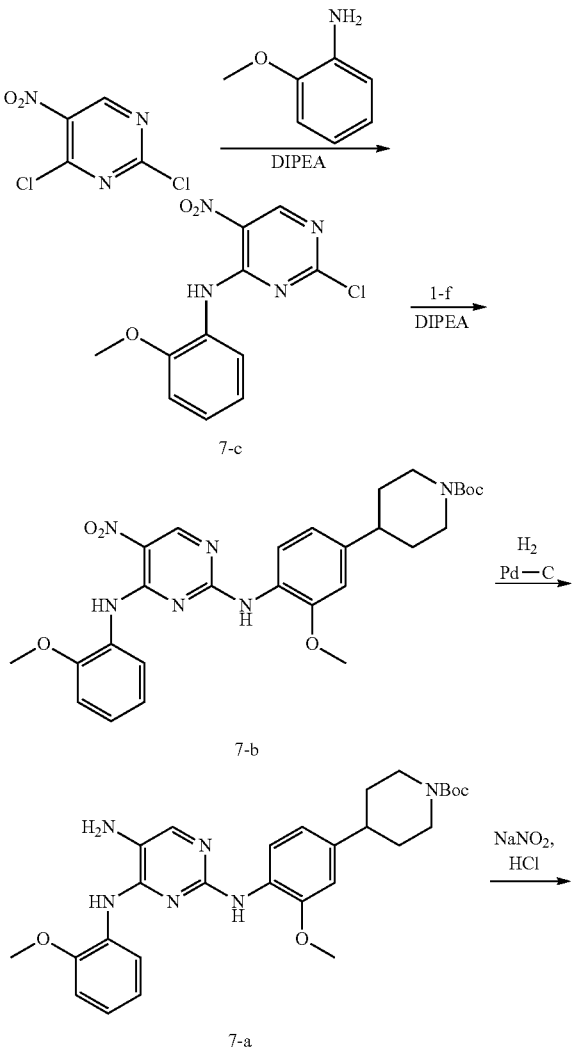

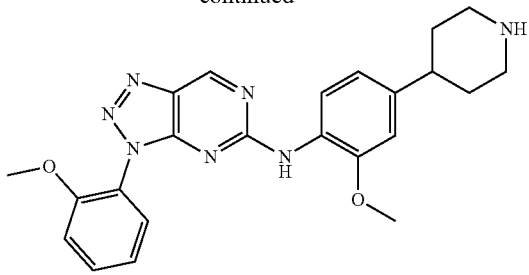

7

Preparation of Compound 7-c.

2,3-Dichloro-4-nitropyrimidine (5.8 g, 30 mmol) was dissolved in anhydrous tetrahydrofuran (100 mL) and the reaction solution was cooled to −78° C. Then 2-methoxyaniline (3.7 g, 30 mmol) and diisopropylethylamine (3.9 g, 30 mmol) were added to the solution and stirring was continued for 2 hours. The reaction mixture was allowed to warm to room temperature, 1 M aqueous hydrochloric acid solution (50 mL) was added and then extracted with dichloromethane (50 mL×3). The combined organic phases were dried over anhydrous sodium sulfate and filtered, and the filtrate was concentrated under reduced pressure to deliver a yellow solid 7-c (6.9 g, yield: 82%). This product was used without further purification. LC-MS (ESI): m/z=289 [M+H]$^+$.

Preparation of Compound 7-b.

Compound 7-c (0.84 g, 3 mmol), compound 1-f (1.0 g, 3 mmol) and diisopropylethylamine (0.78 g, 6 mmol) were dissolved in tetrahydrofuran (100 mL). And the reaction mixture was stirred at 40° C. for 3 hours. The reaction mixture was concentrated under reduced pressure, and the residue was added to 1 M aqueous hydrochloric acid solution (2 mL), and then extracted with dichloromethane (5 mL×3). The combined organic phases were dried over anhydrous sodium sulfate, filtered and the filtrate was concentrated under reduced pressure to deliver a yellow solid 7-b (1.3 g, yield: 79%). This product was used without further purification. LC-MS (ESI): m/z=551 [M+H]$^+$.

Preparation of Compound 7-a.

Compound 7-b (750 mg, 1.5 mmol) and 10% palladium-carbon (150 mg) were dissolved in methanol (10 mL). The reaction mixture was replaced with hydrogen three times and then hydrogenated at 40° C. for 3 hours. The reaction mixture was cooled to room temperature, and the palladium-carbon was removed by filtration. The filtrate was concentrated under reduced pressure to deliver a yellow solid 7-a (610 mg, yield: 78%). This product was used without further purification. LC-MS (ESI): m/z=521 [M+H]$^+$.

Preparation of Compound 7.

Compound 7-a (260 mg, 0.5 mmol) was added to 4 M aqueous hydrochloric acid solution (2 mL) and acetic acid (2 mL) and the reaction solution was cooled to −5° C. Sodium nitrite (70 mg, 1 mmol) was then slowly added to the mixture and stirring was continued for 2 hours. Saturated aqueous sodium bicarbonate solution (8 mL) was added to the reaction mixture, a solid was precipitated and filtered, and the filter cake was washed with water (5 mL×3) and dried in vacuo to deliver a yellow solid 7 (130 mg, yield: 60%). LC-MS (ESI): m/z=432 [M+H]$^+$.

$^1$H-NMR (400 MHz, CD$_3$OD) δ: 9.26 (s, 1H), 8.25 (d, J=8 Hz, 1H), 7.68 (t, J=8 Hz, 1H), 7.64 (d, J=8 Hz, 1H), 7.36 (d, J=8 Hz, 1H), 7.25 (t, J=8 Hz, 1H), 6.90 (s, 1H), 6.74 (d, J=8 Hz, 1H), 3.94 (s, 3H), 3.84 (s, 3H), 3.17 (m, 2H), 2.77 (t, J=12 Hz, 2H), 2.66 (m, 1H), 1.83 (m, 2H), 1.69 (m, 2H) ppm.

Example 8

N-[2-Methoxy-4-(piperidin-4-yl)phenyl]-7-(2-methoxyphenyl)-6-methylthieno[3,2-d]pyrimidin-2-amine (Compound 8)

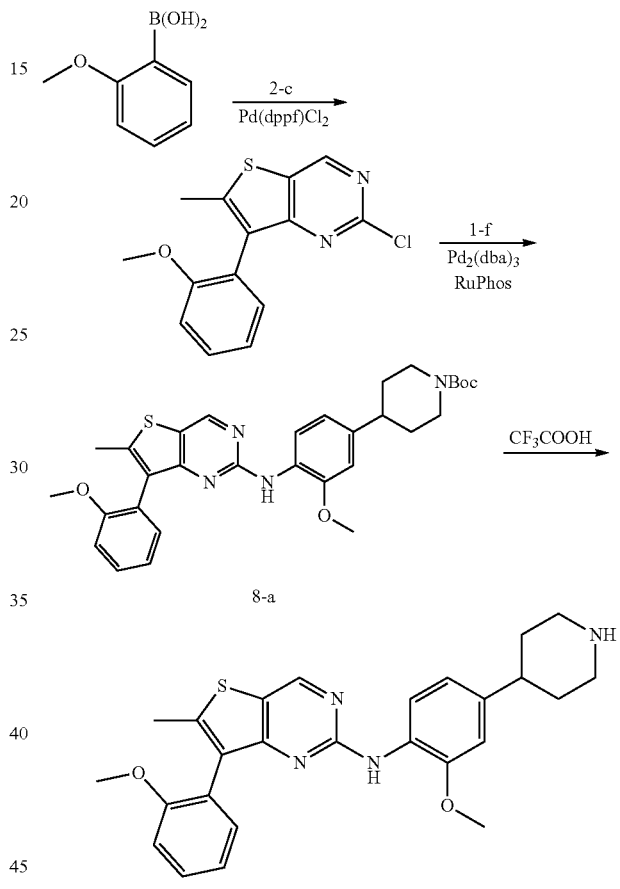

Preparation of Compound 8-b.

Compound 2-c (380 mg, 1.5 mmol), o-methoxyphenylboronic acid (150 mg, 1.0 mmol), [1,1′-bis(diphenylphosphino)ferrocene]dichloropalladium(II) (82 mg, 0.1 mmol) and sodium carbonate (210 mg, 2 mmol) were dissolved in 1,4-dioxane (8 mL) and water (2 mL). The reaction mixture was replaced with nitrogen three times to remove the oxygen inside the system and then heated at 110° C. for 8 hours. The reaction mixture was cooled to room temperature and the reaction mixture was concentrated under reduced pressure to remove a part of dioxane. The residue was filtered through diatomite and the filter cake was washed with ethyl acetate (20 mL×3). The organic phase was washed successively with water (20 mL×3), and brine (10 mL), dried over anhydrous sodium sulfate, filtered, and the filtrate was concentrated under reduced pressure. The residue was purified by silica gel column chromatography (petroleum ether: ethyl acetate=10:1) to deliver a yellow solid 8-b (239 mg, yield: 40%). LC-MS (ESI): m/z=277 [M+H]$^+$.

Preparation of Compound 8-a.

Compound 8-b (145 mg, 0.5 mmol), compound 1-f (150 mg, 0.5 mmol), tris(dibenzylideneacetone)dipalladium (74 mg, 0.13 mmol), potassium carbonate (180 mg, 1.29 mmol) and 2-dicyclohexylphosphino-2',6'-di-iso-propoxy-1,1'-biphenyl (60 mg, 0.13 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature and the reaction mixture was filtered through diatomite. The filter cake was washed with dichloromethane (50 mL) and the organic phase was washed successively with water (20 mL×3) and brine (10 mL), dried over anhydrous sodium sulfate and filtered, and the filtrate was concentrated under reduced pressure. The residue was purified by silica gel thin layer chromatography preparative plate (petroleum ether:ethyl acetate=1:1) to deliver a pale yellow solid 8-a (61 mg, yield: 22%). LC-MS (ESI): m/z=561 [M+H]$^+$.

Preparation of Compound 8.

Compound 8-a (56 mg, 0.1 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure, and the residue was dissolved with ethyl acetate (50 mL), and then 1 M aqueous hydrochloric acid solution (30 mL) was added. The pH of the separated aqueous phase was adjusted to 10 with saturated aqueous potassium carbonate solution. A solid was precipitated and filtered. The filter cake was washed with water (10 mL×3) and dried in vacuo to deliver a pale yellow solid 8 (16 mg, yield: 34.7%). LC-MS (ESI): m/z=461 [M+H]$^+$.

$^1$H-NMR (400 MHz, CD$_3$OD) δ: 8.70 (s, 1H), 8.20 (m, 1H), 7.39 (t, J=8 Hz, 1H), 7.20 (d, J=8 Hz, 1H), 7.07 (m, 2H), 6.70 (s, 1H), 6.51 (d, J=7.2 Hz, 1H), 3.78 (s, 3H), 3.65 (s, 3H), 3.08 (m, 1H), 2.60 (m, 2H), 2.35 (s, 3H), 1.73 (m, 2H), 1.53 (m, 2H) ppm.

Example 9

7-(5-Methanesulfonyl-2-methoxyphenyl)-N-[2-methoxy-4-(piperidin-4-yl)phenyl]thieno[3,2-d]pyrimidin-2-amine (Compound 9)

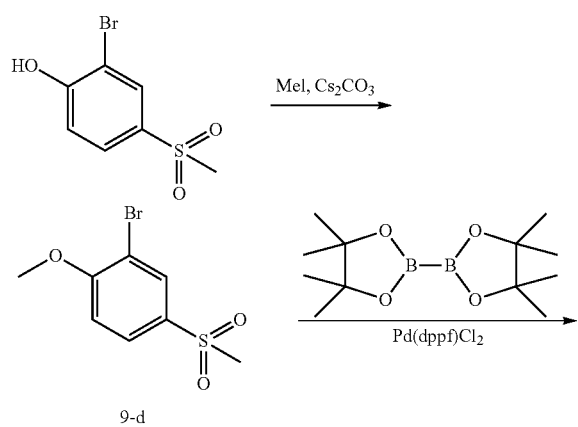

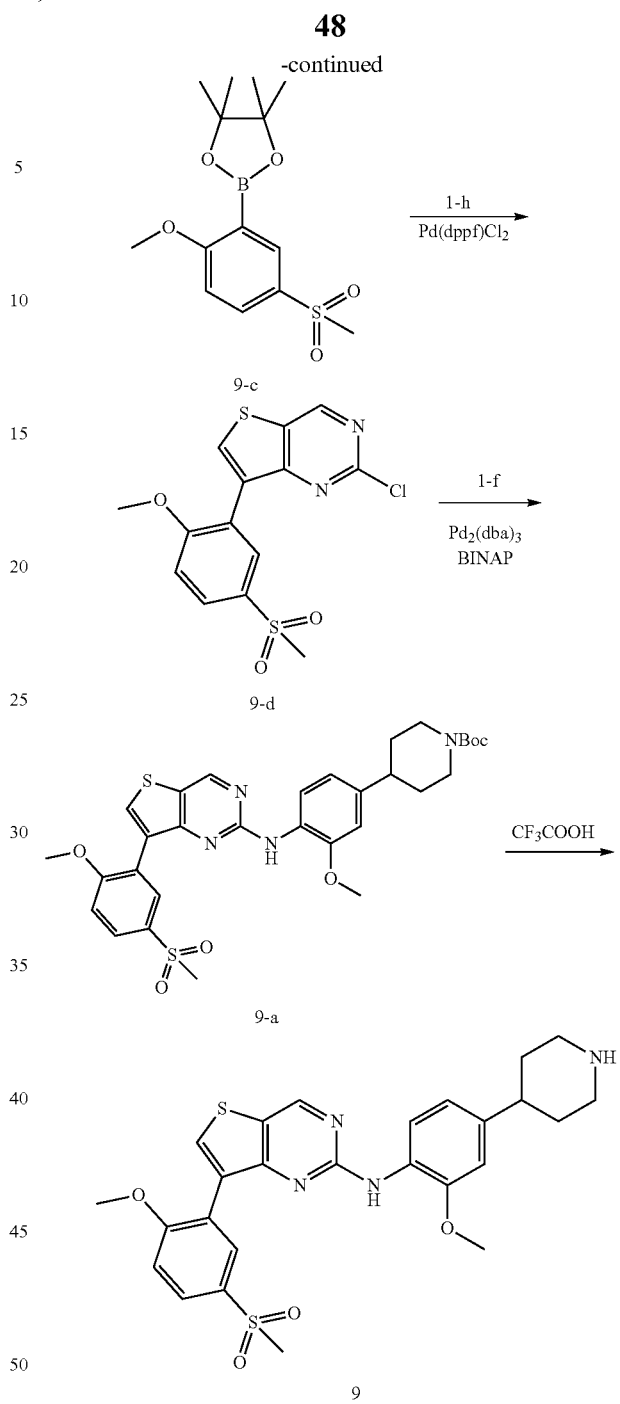

Preparation of Compound 9-d.

2-Bromo-4-(methylsulfonyl)phenol (2.0 g, 7.96 mmol) and iodomethane (3.39 g, 23.9 mmol) were dissolved in tetrahydrofuran (30 mL) and cesium carbonate (7.79 g, 23.9 mmol) was added thereto. The mixture was stirred at room temperature for 16 hours and the mixed solution was concentrated under reduced pressure. The residue was added to water (15 mL) and extracted with dichloromethane (30 mL×2). The combined organic phases were dried over anhydrous sodium sulfate and filtered, and the filtrate was concentrated under reduced pressure to deliver compound 9-d (2 g, yield: 94.7%). This product was used without further purification. LC-MS (ESI): m/z=267 [M+H]$^+$.

Preparation of Compound 9-c.

Compound 9-d (400 mg, 1.51 mmol), bis(pinacolato)diboron (1.15 g, 4.53 mmol), anhydrous potassium acetate (445 mg, 4.53 mmol) and [1,1'-bis(diphenylphosphino)ferrocene]dichloropalladium(II) (110 mg, 0.15 mmol) were dissolved in 1,4-dioxane (15 mL). The reaction mixture was replaced with nitrogen three times to remove the oxygen inside the system and then stirred at 90° C. for 16 hours. The reaction mixture was cooled to room temperature and the reaction mixture was concentrated under reduced pressure. The residue was purified by silica gel column chromatography (petroleum ether:ethyl acetate=2:1) to deliver compound 9-c (341 mg, yield: 72%). LC-MS (ESI): m/z=348 [M+H]+.

Preparation of Compound 9-b.

Compound 9-c (200 mg, 0.8 mmol), compound 1-h (300 mg, 0.96 mmol), sodium carbonate (24 mg, 2.4 mmol) and [1,1'-bis(diphenylphosphino)ferrocene]dichloropalladium (II) (117 mg, 0.16 mmol) were dissolved in 1,4-dioxane (12 mL) and water (2 mL). The reaction solution was replaced with nitrogen three times to remove the oxygen inside the system and then stirred at 90° C. for 16 hours. The reaction mixture was cooled to room temperature, and the reaction mixture was concentrated under reduced pressure. The residue was purified by silica gel column chromatography (petroleum ether:ethyl acetate=1:1) to deliver compound 9-b (140 mg, yield: 49%). LC-MS (ESI): m/z=355 [M+H]+.

Preparation of Compound 9-a.

Compounds 9-b (140 mg, 0.39 mmol), compound 1-f (133 mg, 0.43 mmol), cesium carbonate (381 mg, 0.43 mmol), tris(dibenzylideneacetone)dipalladium (14 mg, 0.01 mmol) and 2,2'-bis(diphenylphosphino)-1,1'-binaphthyl (15 mg, 0.02 mmol) were dissolved in toluene (15 mL). The reaction mixture was replaced with nitrogen three times to remove the oxygen inside the system and then heated at 110° C. for 16 hours. The reaction mixture was cooled to room temperature and the reaction mixture was concentrated under reduced pressure. The residue was purified by silica gel column chromatography (dichloromethane:methanol=40:1) to deliver compound 9-a (150 mg, yield: 63%). LC-MS (ESI): m/z=625 [M+H]+.

Preparation of Compound 9.

Compound 9-a (155 mg, 0.25 mmol) was dissolved in dichloromethane (6 mL). The reaction solution was cooled to 0° C., trifluoroacetic acid (2 mL) was added, and the reaction mixture was stirred at room temperature for 1 hour. The pH of the reaction mixture was adjusted to 8-9 with saturated aqueous sodium carbonate solution and then extracted with dichloromethane (15 mL×3). The combined organic phases were dried over anhydrous sodium sulfate, filtered and the filtrate was concentrated under reduced pressure. The residue was purified by preparative high performance liquid chromatography (mobile phase: 10 mM ammonium bicarbonate aqueous solution:acetonitrile=38% to 48%) to deliver compound 9 (10 mg, yield: 7.7%). LC-MS (ESI): m/z=525 [M+H]+.

1H-NMR (400 MHz, CDCl3) δ: 8.95 (s, 1H), 8.44-8.39 (m, 2H), 8.14 (s, 1H), 8.00 (dd, J=8.7, 2.4 Hz, 1H), 7.82 (s, 1H), 7.19 (d, J=8.8 Hz, 1H), 6.80 (d, J=8.3 Hz, 1H), 6.75 (s, 1H), 3.91 (d, J=12.4 Hz, 6H), 3.34 (d, J=12.2 Hz, 2H), 3.08 (s, 3H), 2.83 (t, J=10.8 Hz, 2H), 2.63 (s, 1H), 1.86 (dd, J=30.8, 10.5 Hz, 4H) ppm.

Example 10

7-(2,3-Dihydro-1-benzofuran-7-yl)-N-[4-(piperidin-4-yl)-2-isopropoxyphenyl]-6-methylthieno[3,2-d]pyrimidin-2-amine (Compound 10)

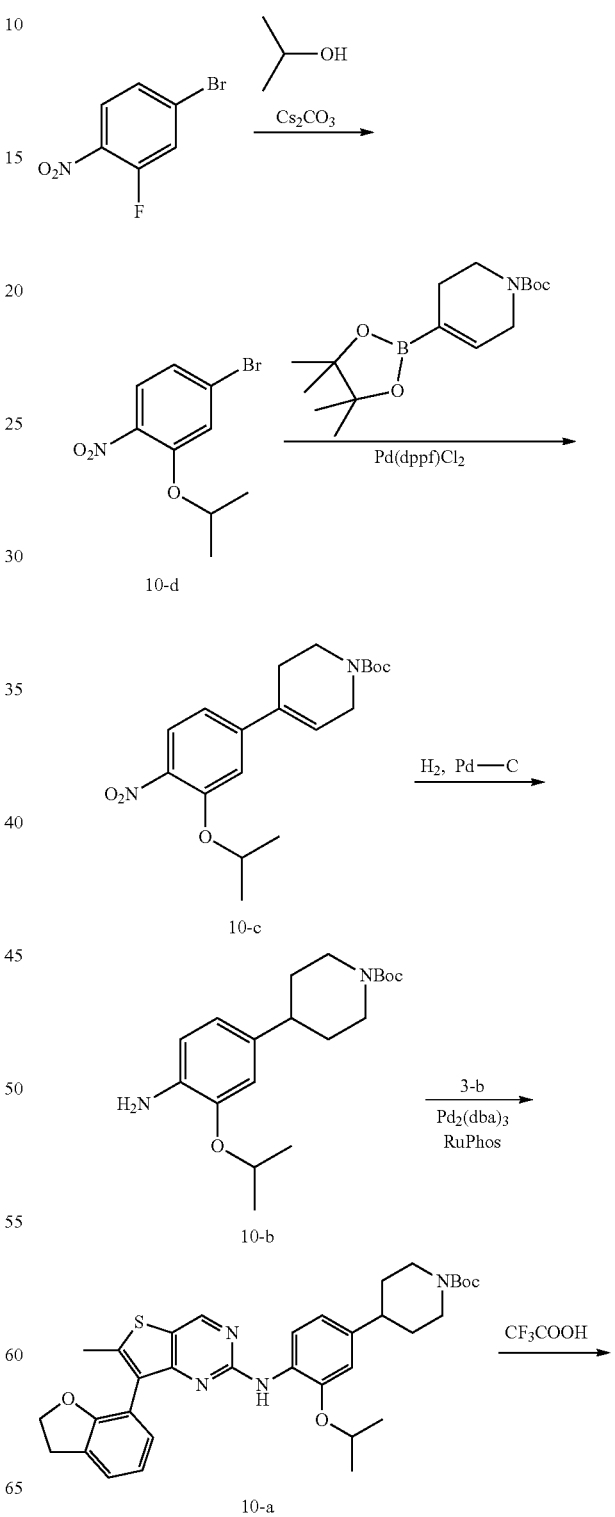

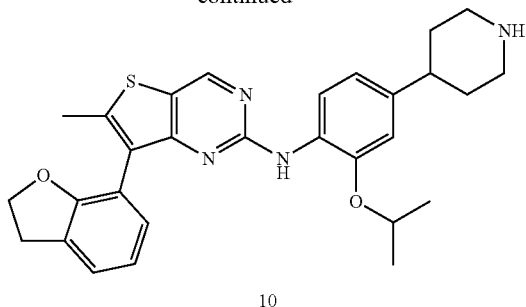

10

Preparation of Compound 10-d.

2-Fluoro-4-bromonitrobenzene (5.0 g, 22.83 mmol) was dissolved in isopropanol (100 mL) and cesium carbonate (37.2 g, 114.16 mmol) was added thereto. The reaction mixture was stirred at 60° C. for 16 hours. The reaction mixture was cooled to room temperature and the reaction mixture was concentrated under reduced pressure. The residue was dissolved in ethyl acetate (150 mL) and then water (150 mL) was added. The separated organic phase was dried over anhydrous sodium sulfate, filtered and the filtrate was concentrated under reduced pressure. The residue was recrystallized from petroleum ether (100 mL) to deliver a yellow solid 10-d (4.7 g, yield: 79%). This product was used without further purification.

Preparation of Compound 10-c.

Compound 10-d (1.2 g, 4.63 mmol), N-Boc-1,2,3,6-tetrahydropyridine-4-boronic acid pinacol ester (1.72 g, 5.56 mmol), sodium carbonate (147 g, 13.89 mmol) and [1,1'-bis(diphenylphosphino)ferrocene]dichloropalladium(II) (375 mg, 0.46 mmol) were dissolved in dioxane (15 mL) and water (15 mL). The reaction mixture was replaced with nitrogen three times to remove the oxygen inside the system and then heated at 80° C. for 16 hours. The reaction mixture was cooled to room temperature and concentrated under reduced pressure. The residue was dissolved in dichloromethane (100 mL). The organic phase was washed with water (100 mL), dried over anhydrous sodium sulfate, filtered, and the filtrate was concentrated under reduced pressure. The residue was purified by silica gel column chromatography (petroleum ether:ethyl acetate=5:1) to deliver a pale yellow solid 10-c (1.17 g, yield: 71%). LC-MS (ESI): m/z=307 [M+H-t-Bu]$^+$.

Preparation of Compound 10-b.

Compound 10-c (610 mg, 1.68 mmol) and 10% palladium-carbon (150 mg) were dissolved in ethanol (20 mL). The reaction mixture was replaced with hydrogen three times and then hydrogenated at room temperature for 16 hours. The reaction mixture was filtered to remove palladium-carbon and the filtrate was concentrated under reduced pressure to deliver a purple oil 10-b (435 mg, yield: 84%). This product was used without further purification. LC-MS (ESI): m/z=335 [M+H]$^+$.

Preparation of Compound 10-a.

Compound 10-b (132 mg, 0.39 mmol), compound 3-b (120 mg, 0.39 mmol), potassium carbonate (168 mg, 1.22 mmol), tris(dibenzylideneacetone)dipalladium (72 mg, 0.13 mmol) and 2-dicyclohexylphosphino-2',6'-di-iso-propoxy-1,1'-biphenyl (72 mg, 0.15 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature and the reaction mixture was filtered through diatomite. The filter cake was washed with dichloromethane (50 mL×3). The filtrate was washed with water (20 mL×3), dried over anhydrous sodium sulfate, filtered. The residue was purified by silica gel thin layer chromatography preparative plate (petroleum ether:ethyl acetate=3:1) to deliver a yellow solid 10-a (71 mg, yield: 30%). LC-MS (ESI): m/z=601 [M+H]$^+$.

Preparation of Compound 10.

Compound 10-a (71 mg, 0.12 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in dichloromethane (50 mL) and then saturated aqueous sodium carbonate solution (50 mL) was added. The organic phase was dried over anhydrous sodium sulfate, filtered, and the filtrate was concentrated under reduced pressure. The residue was purified by silica gel thin layer chromatography preparative plate (dichloromethane:methanol=10:1) to deliver a pale yellow solid 10 (35 mg, yield: 39%). LC-MS (ESI): m/z=501 [M+H]$^+$.

$^1$H-NMR (400 MHz, CDCl$_3$) δ: 8.77 (s, 1H), 8.59 (d, J=8 Hz, 1H), 7.80 (s, 1H), 7.37 (d, J=8 Hz, 1H), 7.31 (dd, J=8 Hz, J=2 Hz, 1H), 6.73 (m, 1H), 6.69 (s, 1H), 6.67 (dd, J=8 Hz, J=2 Hz, 1H), 4.56-4.65 (m, 3H), 3.57-3.60 (m, 2H), 3.31-3.36 (m, 2H), 2.98-3.04 (m, 1H), 2.57 (s, 3H), 2.07-2.13 (m, 2H), 2.00-2.07 (m, 2H), 1.37 (s, 3H), 1.38 (s, 3H) ppm.

Example 11

7-(2-Methylphenyl)-N-[4-(piperidin-4-yl)-2-isopropoxyphenyl]-6-methylthieno[3,2-d]pyrimidine-2-amine (Compound 11)

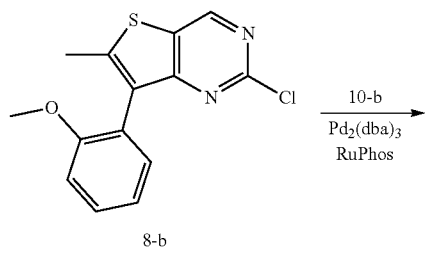

8-b

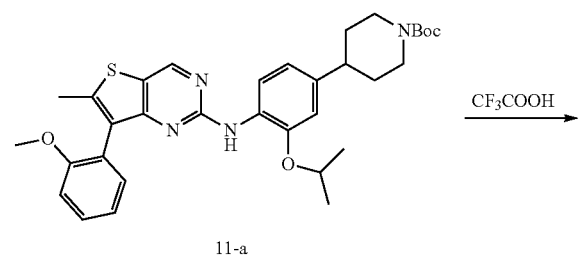

11-a

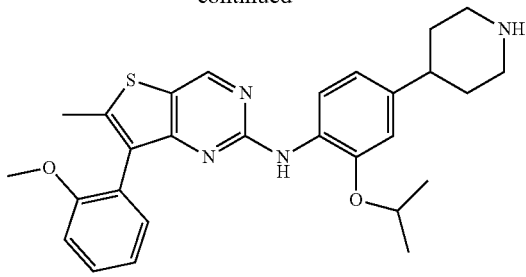

11

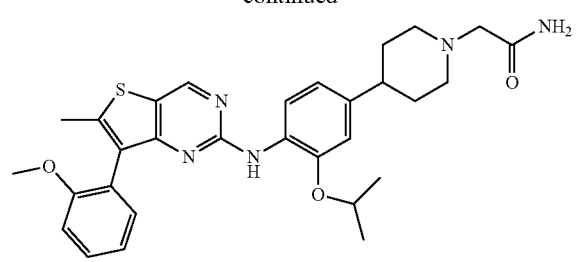

12

Preparation of Compound 11-a.

Compound 10-b (242 mg, 0.73 mmol), compound 8-b (210 mg, 0.73 mmol), potassium carbonate (300 mg, 2.17 mmol), tris(dibenzylideneacetone)dipalladium (124 mg, 0.73 mmol) and 2-dicyclohexylphosphino-2',6'-di-isopropoxy-1,1'-biphenyl (101 mg, 0.22 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature and the reaction was filtered through diatomite. The filter cake was washed with dichloromethane (50 mL×3) and the combined filtrates were concentrated under reduced pressure. The residue was purified by silica gel thin layer chromatography preparative plate (ether:ethyl acetate=3:1) to deliver a pale yellow solid 11-a (145 mg, yield: 34%). LC-MS (ESI): m/z=589 [M+H]$^+$.

Preparation of Compound 11.

Compound 11-a (145 mg, 0.25 mmol) was dissolved in dichloromethane (3 mL). The reaction solution was cooled to 0° C., trifluoroacetic acid (3 mL) was added, and the reaction mixture was stirred at room temperature for 2 hours. The reaction mixture was concentrated under reduced pressure and the residue was dissolved in dichloromethane (50 mL) and then saturated aqueous sodium carbonate solution (50 mL) was added. The organic phase was dried over anhydrous sodium sulfate, filtered, and the filtrate was concentrated under reduced pressure. The residue was purified by silica gel thin layer chromatography preparative plate (dichloromethane:methanol=10:1) to deliver a pale yellow solid 11 (125 mg, yield: 100%). LC-MS (ESI): m/z=488 [M+H]$^+$.

$^1$H-NMR (400 MHz, CDCl$_3$) δ: 8.76 (s, 1H), 8.46 (d, J=8 Hz, 1H), 7.74 (s, 1H), 7.42-7.47 (m, 2H), 7.10-7.14 (m, 1H), 7.06 (d, J=8 Hz, 1H), 6.72 (d, J=2 Hz, 1H), 6.63 (dd, J=8 Hz, J=2 Hz, 1H), 4.56-4.61 (m, 1H), 3.78 (s, 3H), 3.20-3.23 (m, 2H), 2.73-2.78 (m, 2H), 2.51-2.55 (m, 1H), 2.50 (s, 3H), 1.76-1.83 (m, 4H), 1.35 (d, J=8 Hz, 6H) ppm.

Example 12

2-[4-(4-{[7-(2-Methylphenyl)-6-methylthieno[3,2-d]pyrimidin-2-yl]amino}-3-isopropoxyphenyl)piperidin-1-yl]acetamide (Compound 12)

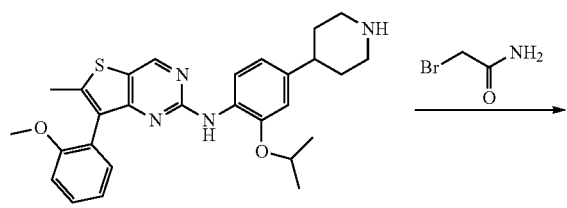

11

Preparation of Compound 12.

Compound 11 (50 mg, 0.11 mmol) and bromoacetamide (21 mg, 0.16 mmol) were dissolved in anhydrous ethanol (3 mL) and then potassium carbonate (22 mg, 0.16 mmol) was added. After the reaction mixture was stirred at room temperature for 16 hours, the mixture was filtered and the filter cake was washed with ethyl acetate (10 mL×3). The filtrate was concentrated under reduced pressure and the residue was purified by silica gel thin layer chromatography preparative plate (dichloromethane:methanol=10:1) to deliver compound 12 (35 mg, yield: 63%). LC-MS (ESI): m/z=546 [M+H]$^+$.

$^1$H-NMR (400 MHz, CDCl$_3$) δ: 8.76 (s, 1H), 8.46 (d, J=8 Hz, 1H), 7.74 (s, 1H), 7.43-7.47 (m, 2H), 7.10-7.14 (m, 1H), 7.06 (d, J=8 Hz, 1H), 6.72 (d, J=2 Hz, 1H), 6.63 (dd, J=8 Hz, J=2 Hz, 1H), 5.62 (br, 1H), 4.56-4.61 (m, 1H), 3.78 (s, 3H), 3.03 (s, 2H), 2.97-3.01 (m, 2H), 2.50 (s, 3H), 2.40-2.43 (m, 1H), 2.24-2.30 (m, 2H), 1.81-1.85 (m, 2H), 1.69-1.76 (m, 2H), 1.35 (d, J=8 Hz, 6H) ppm Example 13

7-(2-Methylphenyl)-N-[5-methyl-4-(piperidin-4-yl)-2-isopropoxyphenyl]-6-methylthieno[3,2-d]pyrimidin-2-amine (Compound 13)

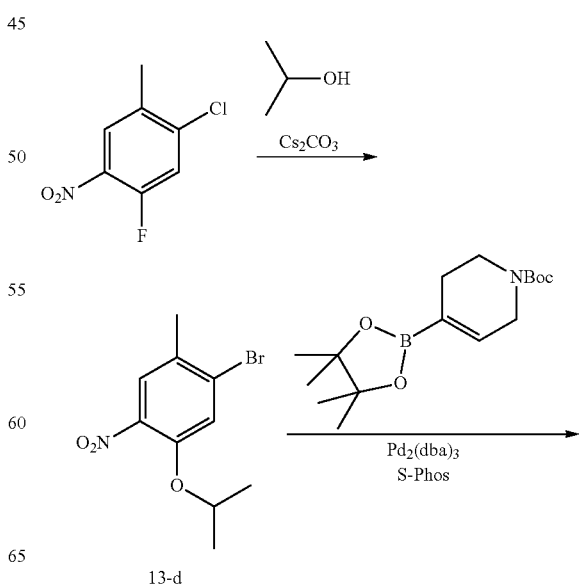

13-d

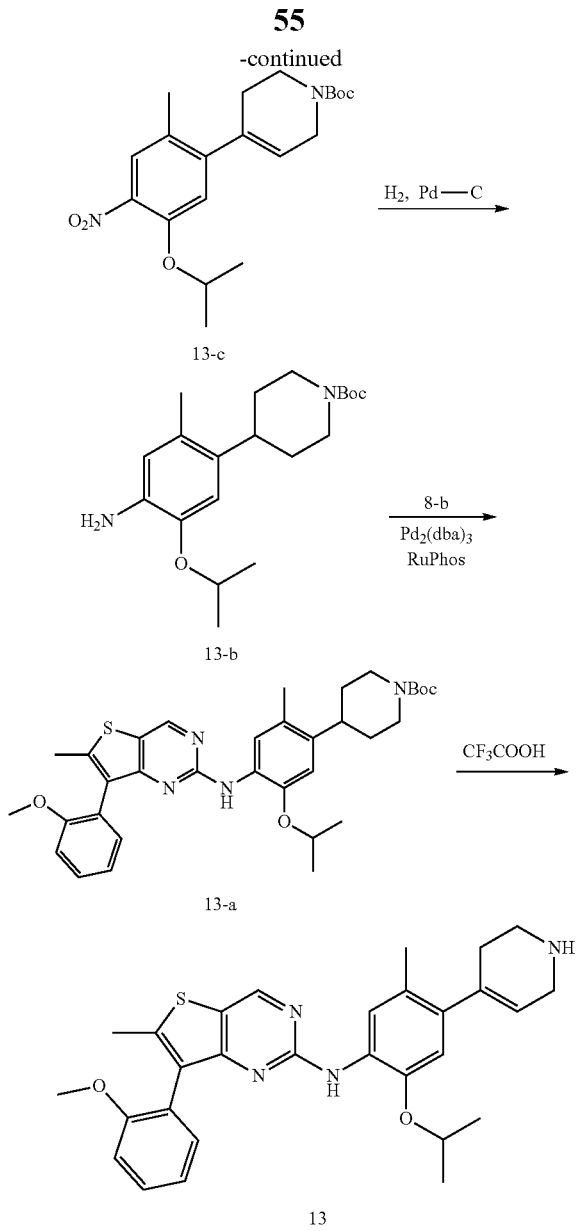

Preparation of Compound 13-d.

2-Chloro-4-fluoro-5-nitrobenzene (25 g, 131 mmol) was dissolved in isopropanol (250 mL) and cesium carbonate (208 g, 659 mmol) was added thereto. The reaction mixture was stirred at 60° C. for 16 hours. The reaction mixture was cooled to room temperature and the reaction mixture was concentrated under reduced pressure. The residue was dissolved in ethyl acetate (250 mL) and then water (250 mL) was added. The separated organic phase was dried over anhydrous sodium sulfate, filtered, and the filtrate was concentrated under reduced pressure. The residue was purified by silica gel column chromatography (petroleum ether: ethyl acetate=19:1) to deliver a yellow solid 13-d (28.7 g, yield: 95%).

$^1$H-NMR (400 MHz, DMSO-$d_6$) δ: 7.90 (d, J=0.6 Hz, 1H), 7.52 (s, 2H), 7.86 (m, 1H), 2.30 (s, 3H), 1.27 (d, J=6 Hz, 6H) ppm.

Preparation of Compound 13-c.

Compound 13-d (2.75 g, 12 mmol), N-Boc-1,2,3,6-tetrahydropyridine-4-boronic acid pinacol ester (4.65 g, 15 mmol), potassium carbonate (4.97 g, 24 mmol), tris(dibenzylideneacetone)dipalladium (375 mg, 0.46 mmol) and 2-dicyclohexylphosphino-2',6'-dimethoxybiphenyl (0.5 g, 1.2 mmol) were dissolved in dioxane (40 mL) and water (10 mL). The reaction mixture was replaced with nitrogen three times to remove the oxygen inside the system and then heated at 150° C. for 12 hours. The reaction mixture was cooled to room temperature and concentrated under reduced pressure to remove a part of dioxane. The residue was dissolved in ethyl acetate (50 mL) and filtered through diatomite. The filtrate was washed with water (50 mL×3), dried over anhydrous sodium sulfate, the filtrate was concentrated under reduced pressure and the residue was purified by silica gel column chromatography (petroleum ether: ethyl acetate=10:1) to deliver a yellow solid 13-c (3.15 g, yield: 70%). LC-MS (ESI): m/z=376 [M+H]$^+$.

Preparation of Compound 13-b.

Compound 13-c (3.15 g, 8.4 mmol) and 10% palladium-carbon (0.5 g) were dissolved in methanol (10 mL). The reaction mixture was replaced with hydrogen three times and then hydrogenated at 40° C. for 3 hours. The reaction mixture was filtered to remove palladium-carbon and the filtrate was concentrated under reduced pressure to deliver a white solid 13-b (2.8 g, yield: 88%). This product was used without further purification. LC-MS (ESI): m/z=378 [M+H]$^+$.

Preparation of Compound 13-a.

Compound 13-b (144 mg, 0.41 mmol), compound 8-b (120 mg, 0.41 mmol), potassium carbonate (173 mg, 1.25 mmol), tris(dibenzylideneacetone)dipalladium (72 mg, 0.13 mmol) and 2-dicyclohexylphosphino-2',6'-di-iso-propoxy-1,1'-biphenyl (59 mg, 0.13 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature and the reaction mixture was filtered through diatomite. The filter cake was washed with dichloromethane (50 mL×3). The filtrate was washed with water (20 mL), dried over anhydrous sodium sulfate, filtered, the filtrate was concentrated under reduced pressure, the residue was purified by silica gel thin layer chromatography preparative plate (petroleum ether:ethyl acetate=5:1) to deliver a yellow oil 13-a (67 mg, yield: 27%). LC-MS (ESI): m/z=603 [M+H]$^+$.

Preparation of Compound 13.

Compound 13-a (67 mg, 0.12 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in dichloromethane (50 mL) and then saturated aqueous sodium carbonate solution (50 mL) was added. The organic phase was dried over anhydrous sodium sulfate, filtered, the filtrate was concentrated under reduced pressure, and the residue was purified by silica gel thin layer chromatography preparative plate (dichloromethane:methanol=10:1) to deliver a pale yellow solid 13 (15 mg, yield: 27%). LC-MS (ESI): m/z=503 [M+H]$^+$.

$^1$H-NMR (400 MHz, CDCl$_3$) δ: 8.76 (s, 1H), 8.36 (s, 1H), 7.76 (s, 1H), 7.41-7.45 (m, 2H), 7.05-7.13 (m, 2H), 6.72 (s, 1H), 4.55-4.60 (m, 1H), 3.77 (s, 3H), 3.50-3.53 (m, 2H), 2.99-3.05 (m, 2H), 2.80-2.89 (m, 1H), 2.49 (s, 3H), 2.08 (s, 3H), 1.90-2.04 (m, 4H), 1.37 (d, J=8 Hz, 6H) ppm.

Example 14

7-(2,3-Dihydro-1-benzofuran-7-yl)-N-[5-methyl-4-(piperidin-4-yl)-2-isopropoxyphenyl]6-methylthieno[3,2-d]pyrimidin-2-amine (Compound 14)

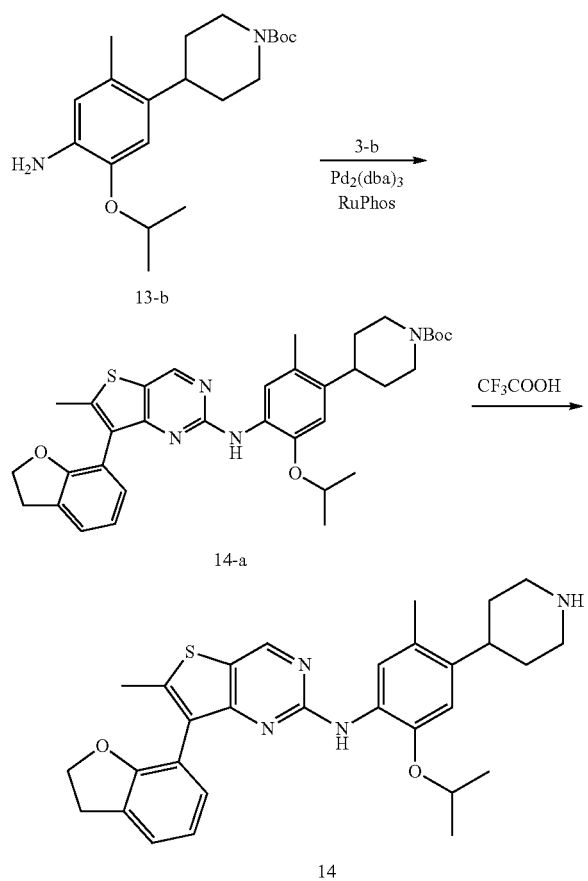

Preparation of Compound 14-a.

Compound 13-b (98 mg, 0.28 mmol), compound 3-b (85 mg, 0.28 mmol), potassium carbonate (116 mg, 0.84 mmol), tris(dibenzylideneacetone)dipalladium (48 mg, 0.09 mmol) and 2-dicyclohexylphosphino-2',6'-di-iso-propoxy-1,1'-biphenyl (39 mg, 0.09 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature and the reaction mixture was filtered through diatomite. The filter cake was washed with dichloromethane (50 mL×3). The filtrate was washed with water (20 mL), dried over anhydrous sodium sulfate, filtered, the filtrate was concentrated under reduced pressure. The residue was purified by silica gel thin layer chromatography preparative plate (petroleum ether:ethyl acetate=5:1) to deliver a yellow oil 14-a (45 mg, yield: 26%). LC-MS (ESI): m/z=615 [M+H]$^+$.

Preparation of Compound 14.

Compound 14-a (45 mg, 0.08 mmol) was dissolved in dichloromethane (3 mL). The reaction solution was cooled to 0° C., trifluoroacetic acid (3 mL) was added, and the reaction mixture was stirred at room temperature for 2 hours. The reaction was concentrated under reduced pressure and the residue was dissolved in dichloromethane (50 mL) and then saturated aqueous sodium carbonate solution (50 mL) was added. The organic phase was dried over anhydrous sodium sulfate, filtered, the filtrate was concentrated under reduced pressure, and the residue was purified by silica gel thin layer chromatography preparative plate (dichloromethane:methanol=10:1) to deliver a pale yellow solid 14 (26 mg, yield: 69%). LC-MS (ESI): m/z=515 [M+H]$^+$.

$^1$H-NMR (400 MHz, CDCl$_3$) δ: 8.75 (s, 1H), 8.40 (s, 1H), 7.75 (s, 1H), 7.405 (d, J=8 Hz, 1H), 7.26 (d, J=8 Hz, 1H), 7.02 (t, J=8 Hz, 1H), 6.75 (s, 1H), 4.52-4.59 (m, 1H), 3.28-3.32 (m, 2H), 3.17-3.20 (m, 2H), 2.71-2.78 (m, 3H), 2.55 (s, 3H), 2.16 (s, 3H), 1.84 (br, 2H), 1.71-1.74 (m, 2H), 1.57-1.64 (m, 2H), 1.34 (d, J=8 Hz, 6H) ppm.

Example 15

7-(2-Methylphenyl)-N-[4-(piperidin-4-yl)-2,3-dihydro-1-benzofuran-7-yl]-6-methylthieno[3,2-d]pyrimidin-2-amine (Compound 15)

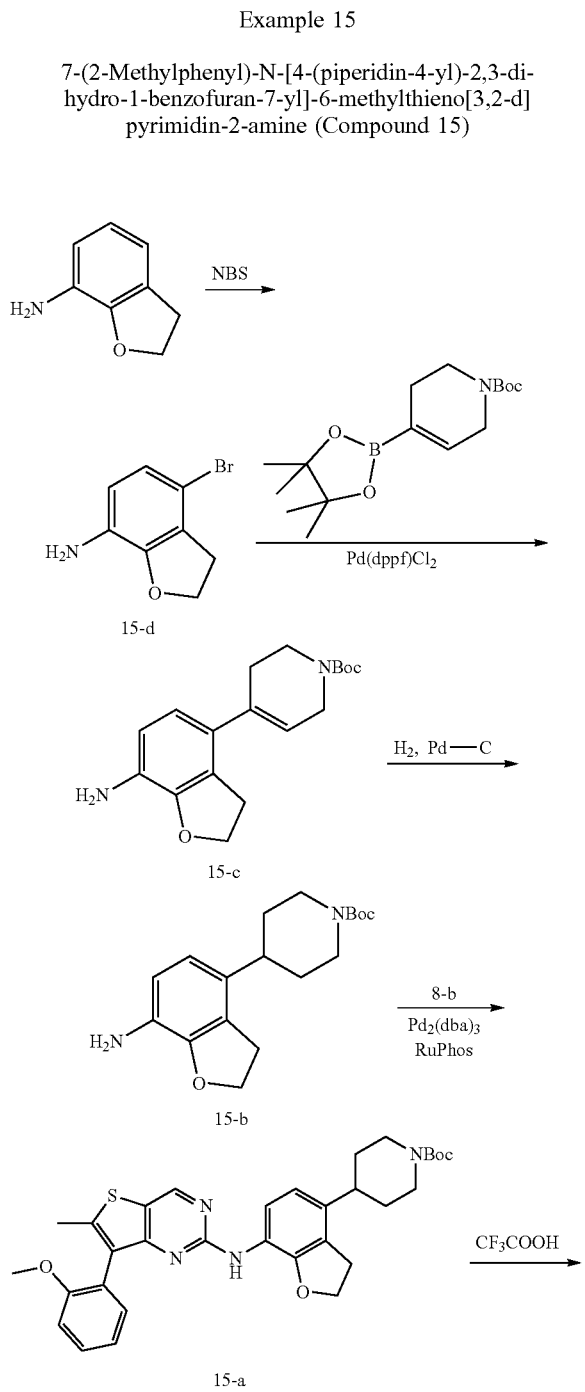

-continued

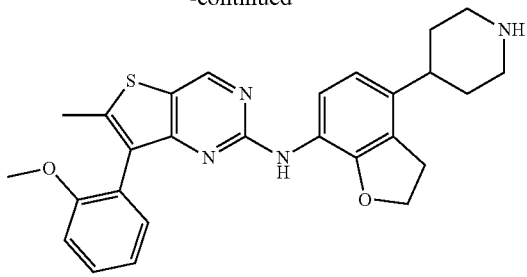

15

Preparation of Compound 15-d.

7-Aminobenzo-2,3-dihydrofuran (3 g, 22.22 mmol) was dissolved in N, N-dimethylformamide (7 mL) and the reaction solution was cooled to 0° C. A solution of N-bromosuccinimide (3.93 g, 22.22 mmol) in N,N-dimethylformamide (7 mL) was then added dropwise to the above solution over 30 minutes. After the addition, stirring was continued for 30 minutes. The reaction mixture was poured into water (100 mL) and extracted with ethyl acetate (100 mL). The organic phase was washed with saturated sodium chloride solution (50 mL×2), dried over anhydrous sodium sulfate, filtered, and the filtrate was concentrated under reduced pressure. And the residue was purified by silica gel column chromatography (petroleum ether:ethyl acetate=10:1) to deliver a yellow solid 15-d (2.5 g, yield: 53%). LC-MS (ESI): m/z=214 (M+H)$^+$.

Preparation of Compound 15-c.

Compound 15-d (2.2 g, 10 mmol), N-Boc-1,2,3,6-tetrahydropyridine-4-boronic acid pinacol ester (3.1 g, 10 mmol), sodium carbonate (2.12 g, 20 mmol) and [1,1'-bis(diphenylphosphino)ferrocene]dichloropalladium(II) (0.55 g, 1 mmol) were dissolved in dioxane (40 mL) and water (10 mL). The reaction mixture was replaced with nitrogen three times to remove the oxygen inside the system and then heated at 80° C. for 12 hours. The reaction mixture was cooled to room temperature and concentrated under reduced pressure to remove a part of dioxane. The residue was dissolved in ethyl acetate (50 mL) and filtered through diatomite. The filtrate was washed with water (20 mL×3) and brine (10 mL), dried over anhydrous magnesium sulfate, filtered, and the filtrate was concentrated under reduced pressure. The residue was purified by silica gel column chromatography (petroleum ether:ethyl acetate=10:1) to deliver a yellow solid 15-c (1.7 g, yield: 53.8%) LC-MS (ESI): m/z=317 [M+H]$^+$.

Preparation of Compound 15-b.

Compound 15-c (1.7 g, 5.38 mmol) and 10% palladium-carbon (0.3 g) were dissolved in methanol (10 mL). The reaction mixture was replaced with hydrogen three times and then hydrogenated at 40° C. for 3 hours. The reaction mixture was filtered to remove palladium-carbon and the filtrate was concentrated under reduced pressure to deliver a pink solid 15-b (1.5 g, yield: 87.7%). This product was used without further purification. LC-MS (ESI): m/z=263 [M+H-t-Bu]$^+$.

Preparation of Compound 15-a.

Compound 15-b (160 mg, 0.5 mmol), compound 8-b (150 mg, 0.5 mmol), potassium carbonate (140 mg, 0.05 mmol), tris(dibenzylideneacetone)dipalladium (46 mg, 0.05 mmol) and 2-dicyclohexylphosphino-2',6'-di-iso-propoxy-1,1'-biphenyl (24 mg, 0.05 mmol) were dissolved in N,N-dimethylformamide (5 mL), the reaction mixture was replaced with nitrogen three times to remove the oxygen inside the system and then heated at 110° C. for 16 hours. The reaction mixture was cooled to room temperature and the reaction mixture was filtered through diatomite. The filter cake was washed with dichloromethane (50 mL×3). The filtrate was washed with water (20 mL), dried over anhydrous sodium sulfate, filtered, the filtrate was concentrated under reduced pressure. The residue was purified by silica gel thin layer chromatography preparative plate (petroleum ether:ethyl acetate=1:1) to deliver a yellow oil 15-a (180 mg, yield: 63%). LC-MS (ESI): m/z=573 [M+H]$^+$.

Preparation of Compound 15.

Compound 15-a (180 mg, 0.31 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure, and the residue was dissolved with ethyl acetate (50 mL), and then 1 M aqueous hydrochloric acid solution (30 mL) was added. The pH of the separated aqueous phase was adjusted to 10 with saturated aqueous potassium carbonate solution, a solid was precipitated and filtered. The filter cake was washed with water (10 mL×3) and dried in vacuo to deliver a pale yellow solid 15 (110 mg, yield: 74%). LC-MS (ESI): m/z=473 [M+H]$^+$.

$^1$H-NMR (400 MHz, DMSO-d$_6$) δ: 8.94 (s, 1H), 8.00 (s, 1H), 7.56 (d, J=8 Hz, 1H), 7.44 (t, J=8 Hz, 1H), 7.30 (d, J=8 Hz, 1H), 7.06 (t, J=8 Hz, 1H), 6.51 (d, J=8 Hz, 1H), 4.51 (t, J=8 Hz, 2H), 3.71 (s, 3H), 3.18 (m, 4H), 2.40 (s, 3H), 1.62 (m, 4H) ppm.

Example 16

7-(2-Ethoxyphenyl)-6-methyl-N-[4-(piperidin-4-yl)-2,3-dihydro-1-benzofuran-7-yl]thieno[3,2-d]pyrimidin-2-amine (Compound 16)

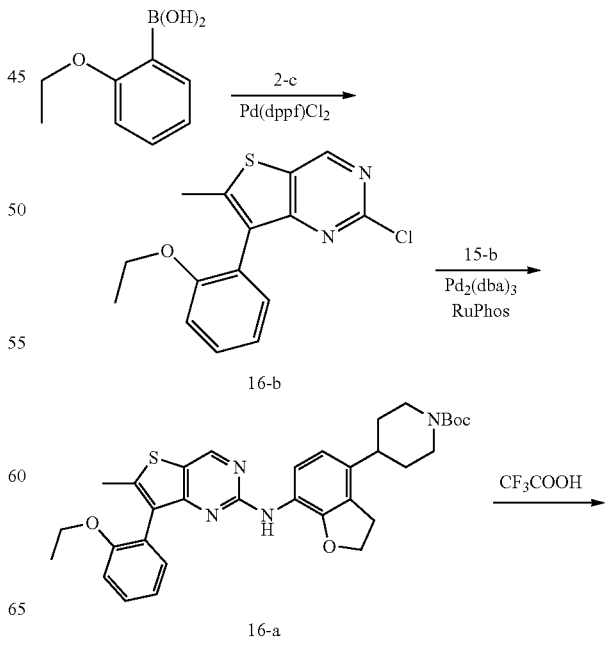

-continued

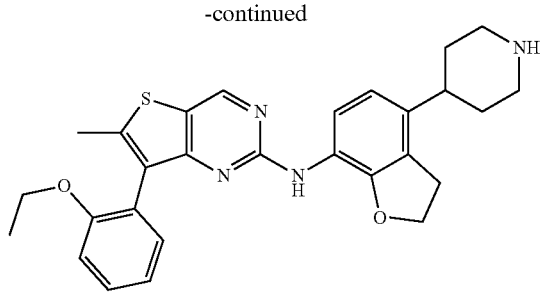

16

Preparation of Compound 16-b.

Compound 2-c (620 mg, 2 mmol), o-ethoxybenzeneboronic acid (330 mg, 2 mmol), [1,1'-bis(diphenylphosphino)ferrocene]dichloropalladium(II)(100 mg, 0.14 mmol) and sodium carbonate (500 mg, 4.7 mmol) were dissolved in 1,4-dioxane (20 mL) and water (5 mL). The reaction mixture was replaced with nitrogen three times to remove the oxygen inside the system and then heated at 80° C. for 16 hours. The reaction mixture was cooled to room temperature, diluted with water (10 mL) and extracted with ethyl acetate (50 mL×3). The combined organic phases were washed successively with water (20 mL×3) and brine (20 mL), dried over sodium sulfate, filtered, and the filtrate was concentrated under reduced pressure. The residue was purified by silica gel column chromatography (petroleum ether:ethyl acetate=5:1) to deliver a white solid 16-b (300 mg, yield: 49%). LC-MS (ESI): m/z=305 [M+H]$^+$.

Preparation of Compound 16-a.

Compound 16-b (300 mg, 0.98 mmol), compound 15-b (3.2 g, 1 mmol), potassium carbonate (400 mg, 2.89 mmol), tris(dibenzylideneacetone)dipalladium (70 mg, 0.07 mmol) and 2-dicyclohexylphosphino-2',6'-di-iso-propoxy-1,1'-biphenyl (50 mg, 0.1 mmol) were dissolved in N,N-dimethylformamide (10 mL), and the reaction mixture was replaced with nitrogen three times to remove the oxygen inside the system and then heated at 130° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=5:1) to deliver a yellow solid 16-a (200 mg, yield: 34%). LC-MS (ESI): m/z=578 [M+H]$^+$.

Preparation of Compound 16.

Compound 16-a (200 mg, 0.34 mmol) was dissolved in dichloromethane (10 mL). The reaction solution was cooled to 0° C., trifluoroacetic acid (2 mL) was added, and the reaction mixture was stirred at room temperature for 30 minutes. The reaction mixture was concentrated under reduced pressure and the residue was diluted with water (30 mL). The pH was adjusted to 10 with potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=2:1) to deliver a yellow solid 16 (70 mg, yield: 42%). LC-MS (ESI): m/z=487 [M+H]+.

$^1$H-NMR (400 MHz, CD$_3$OD) δ: 8.60 (s, 1H), 7.87 (d, J=8.4 Hz, 1H), 7.29-7.24 (m, 1H), 7.15 (dd, J$_1$=7.6 Hz, J$_2$=1.6 Hz, 1H), 6.95-6.90 (m, 2H), 6.36 (d, J=8.4 Hz, 1H), 4.37 (t, J=8.4 Hz, 2H), 7.29-7.24 (m, 1H), 3.92-3.74 (m, 2H), 3.11-3.07 (m, 2H), 3.00 (t, J=8.4 Hz, 2H), 2.70-2.63 (m, 2H), 2.53-2.45 (m, 1H), 2.30 (s, 1H), 1.60-1.50 (m, 4H), 1.01 (t, J=7.6 Hz, 2H) ppm.

Example 17

4-[7-({7-[2-Methoxy-4-trifluoromethylphenyl]-6-methylthieno[3,2-d]pyrimidin-2-yl}amino)-2,3-dihydro-1-benzofuran-4-yl]piperidin-3-ol (Compound 17)

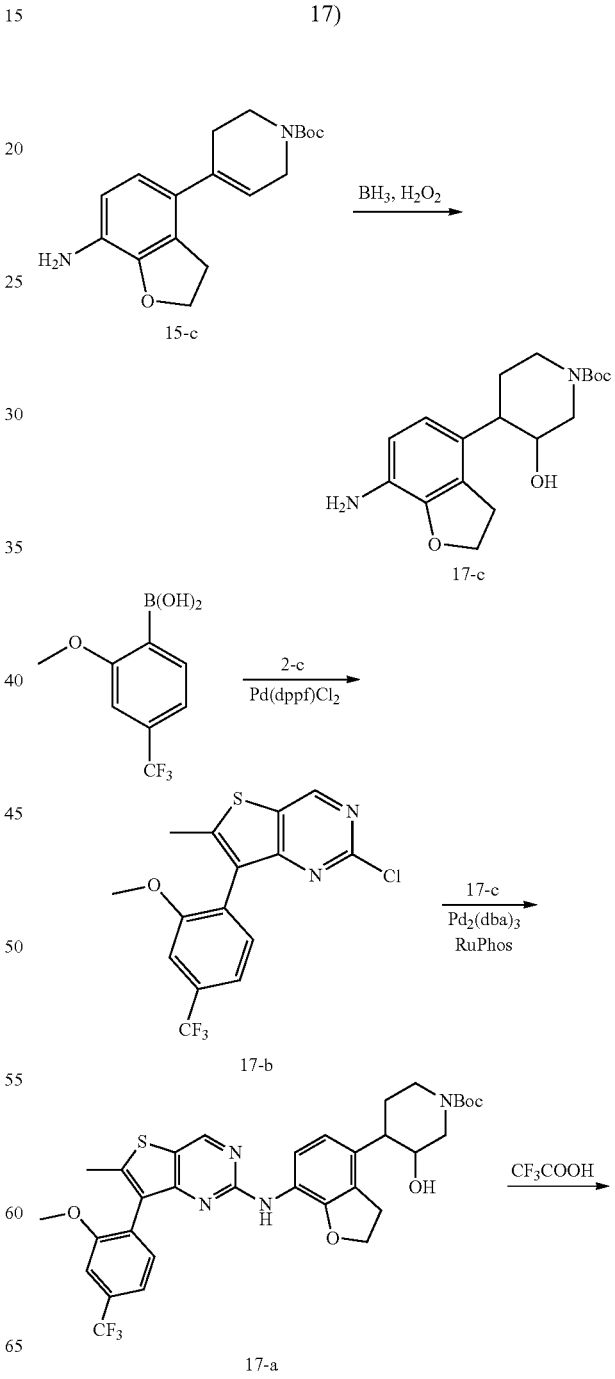

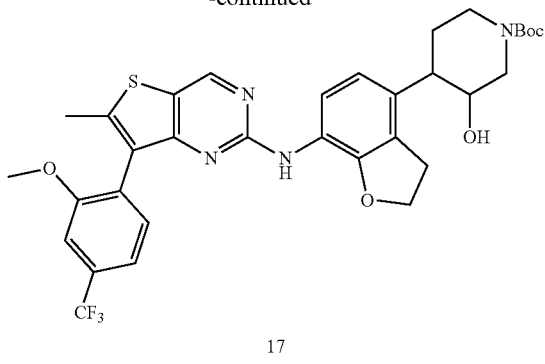

17

Preparation of Compound 17-c.

1 M Solution of borane in tetrahydrofuran (15.8 mL) was added dropwise to a solution of compound 15-c (1 g, 3.16 mmol) in tetrahydrofuran (10 mL) at 0° C. After the addition, the reaction mixture was allowed to warm to room temperature and stirring was continued for 30 minutes. The reaction mixture was cooled to 0° C. again, and 2 M aqueous sodium hydroxide solution was added dropwise to adjust the pH of the reaction mixture to 10, and then 30% hydrogen peroxide (1 mL) was added. The reaction mixture was allowed to warm to room temperature and the stirring was continued for 16 hours. The separated organic phase was dried over anhydrous sodium sulfate, filtered, and the filtrate was concentrated under reduced pressure. The residue was purified by silica gel column chromatography (petroleum ether:ethyl acetate=1:1) to deliver a pale yellow solid 17-c (653 mg, yield: 62%). LC-MS (ESI): m/z=279 [M+H-t-Bu]$^+$.

Preparation of Compound 17-b.

Compound 2-c (3.1 g, 10 mmol), o-methoxy-p-trifluoromethylphenylboronic acid (2.2 g, 10 mmol), [1,1'-bis (diphenylphosphino)ferrocene]dichloropalladium(II) (700 mg, 1 mmol) and sodium carbonate (3.0 g, 30 mmol) were dissolved in 1,4-dioxane (60 mL) and water (15 mL). The reaction mixture was replaced with nitrogen three times to remove the oxygen inside the system and then heated at 120° C. for 16 hours. The reaction mixture was cooled to room temperature, diluted with ice water (50 mL) and extracted with dichloromethane (150 mL×3). The combined organic phases were washed successively with water (50 mL×3) and brine (50 mL), dried over anhydrous sodium sulfate, filtered, and the filtrate was concentrated under reduced pressure. The residue was purified by silica gel column chromatography (petroleum ether:ethyl acetate=5:1) to deliver a white solid 17-b (2.25 g, yield: 63%). LC-MS (ESI): m/z=359 [M+H]$^+$.

Preparation of Compound 17-a.

Compound 17-b (500 mg, 1.4 mmol), compound 17-c (466 mg, 1.4 mmol), potassium carbonate (580 mg, 4.2 mmol), tris(dibenzylideneacetone)dipalladium (100 mg, 0.14 mmol) and 2-dicyclohexylphosphino-2',6'-di-isopropoxy-1,1'-biphenyl (65 mg, 0.14 mmol) were dissolved in N,N-dimethylformamide (10 mL), and the reaction mixture was replaced with nitrogen three times to remove the oxygen inside the system and then heated at 130° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=5:1) to deliver a yellow solid 17-a (200 mg, yield: 22%). LC-MS (ESI): m/z=657 [M+H]$^+$.

Preparation of Compound 17.

Compound 17-a (200 mg, 0.3 mmol) was dissolved in dichloromethane (5 mL). The reaction solution was cooled to 0° C., trifluoroacetic acid (2 mL) was added, and the reaction mixture was stirred at room temperature for 30 minutes. The reaction was concentrated under reduced pressure and the residue was diluted with water (30 mL), the pH was adjusted to 10 with saturated aqueous potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=2:1) to deliver a yellow solid 17 (40 mg, yield: 21%). LC-MS (ESI): m/z=557 [M+H]$^+$.

$^1$H-NMR (400 MHz, CDCl$_3$) δ: 8.78 (s, 1H), 8.11 (d, J=8.0 Hz, 1H), 7.50 (d, J=8.0 Hz, 1H), 7.38 (d, J=8.0 Hz, 1H), 7.19 (s, 1H), 6.65 (d, J=8.0 Hz, 1H), 4.61 (t, J=8.4 Hz, 1H), 3.83 (s, 4H), 3.46-3.12 (m, 4H), 2.78-2.50 (m, 3H), 2.48 (s, 3H), 2.07-1.95 (m, 2H) ppm.

Example 18

7-[2-Methoxy-4-trifluoromethylphenyl]-6-methyl-N-[4-(piperidin-4-yl)-2,3-dihydro-1-benzofuran-7-yl] thieno[3,2-d]pyrimidin-2-amine (Compound 18)

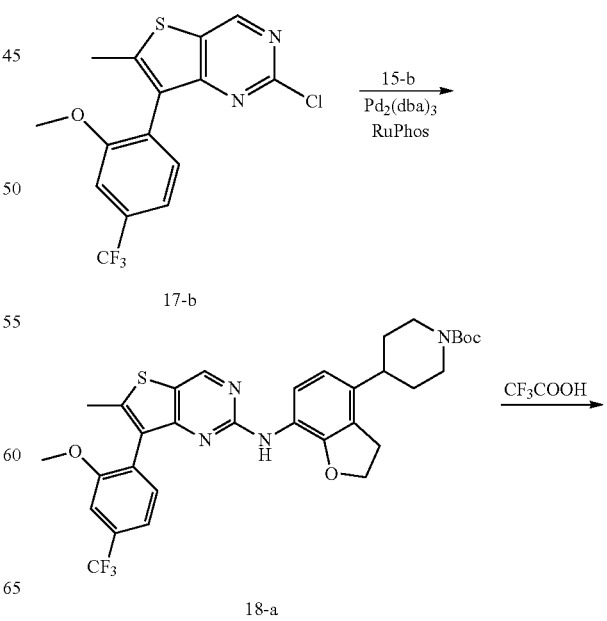

-continued

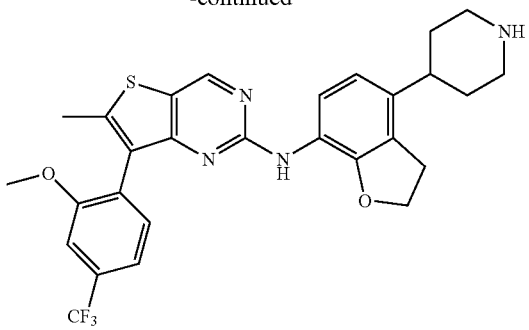

18

Preparation of Compound 18-a.

Compound 17-b (400 mg, 1.12 mmol), compound 15-b (355 mg, 1.12 mmol), potassium carbonate (460 mg, 3.33 mmol), tris(dibenzylideneacetone)dipalladium (80 mg, 0.11 mmol) and 2-dicyclohexylphosphino-2',6'-di-iso-propoxy-1,1'-biphenyl (460 mg, 3.33 mmol) were dissolved in N,N-dimethylformamide (10 mL), and the reaction mixture was replaced with nitrogen three times to remove the oxygen inside the system and then heated at 130° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=5:1) to deliver a yellow solid 18-a (100 mg, yield: 14%). LC-MS (ESI): m/z=641 [M+H]+.

Preparation of Compound 18.

Compound 18-a (200 mg, 0.15 mmol) was dissolved in dichloromethane (5 mL). The reaction solution was cooled to 0° C., trifluoroacetic acid (2 mL) was added, and the reaction mixture was stirred at room temperature for 30 minutes. The reaction mixture was concentrated under reduced pressure and the residue was diluted with water (30 mL), the pH was adjusted to 10 with saturated aqueous potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=2:1) to deliver a yellow solid 18 (24 mg, yield: 28%). LC-MS (ESI): m/z=541 [M+H]+.

1H-NMR (400 MHz, CDCl3) δ: 8.77 (s, 1H), 8.05 (d, J=8.0 Hz, 1H), 7.52 (d, J=8.0 Hz, 1H), 7.38 (d, J=8.0 Hz, 1H), 7.16 (s, 1H), 6.59 (d, J=8.0 Hz, 1H), 4.60 (t, J=8.4 Hz, 1H), 3.82 (s, 4H), 3.28-3.18 (m, 4H), 2.79-2.72 (m, 2H), 2.62-2.52 (m, 1H), 2.49 (s, 3H), 1.82-1.65 (m, 4H) ppm Example 19

N-[2-(2-{[2-Methoxy-4-(piperidin-4-yl)phenyl]amino}quinazolin-8-yl)-N-methylmethanesulfonamide (Compound 19)

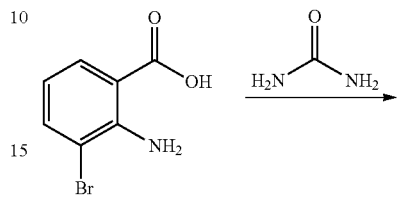

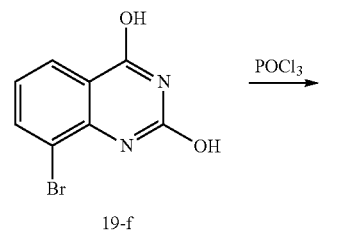

19-f

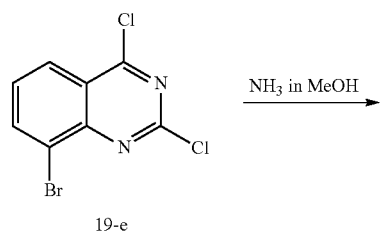

19-e

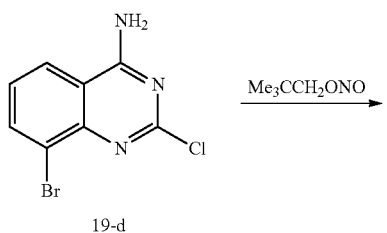

19-d

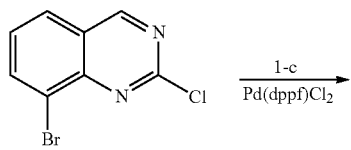

19-c

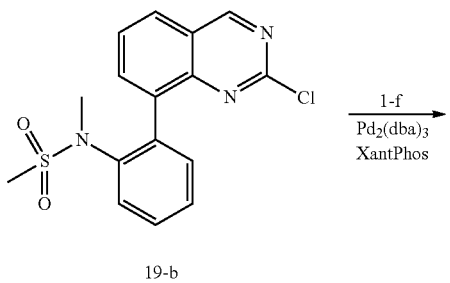

19-b

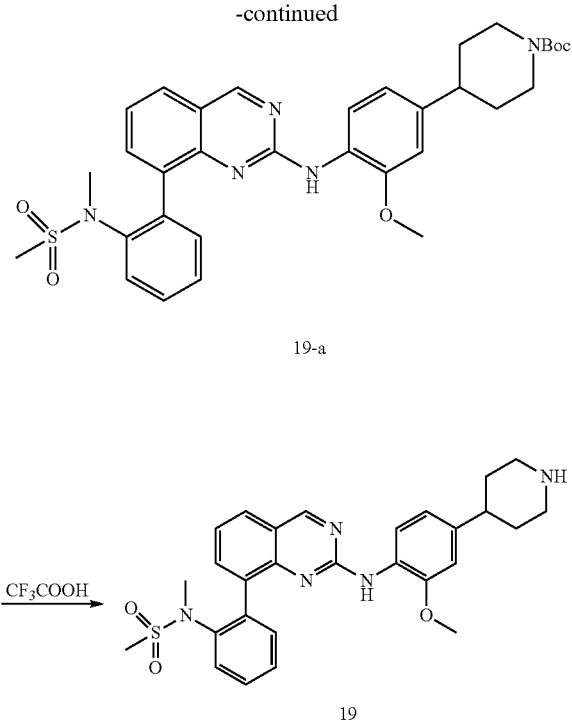

Preparation of Compound 19-f.

2-Amino-3-bromobenzoic acid (5.0 g, 23.26 mmol) was mixed with urea (7.0 g, 116.28 mmol) and the mixture was heated at 210° C. for 2 hours. The reaction mixture was cooled to 90° C. and then water (50 mL) was added and stirred for 30 minutes. The reaction mixture was cooled to room temperature and filtered, and the filter cake was dried in vacuo to deliver a yellow solid 19-f (5.5 g, yield: 98%). This product was used without further purification. LC-MS (ESI): m/z=241 [M+H]$^+$.

Preparation of Compound 19-e.

Compound 19-f (5.5 g, 22.9 mmol) was dissolved in phosphorus oxychloride (30 mL), N, N-dimethylaniline (5 mL) was added and the reaction mixture was heated at 110° C. for 18 hours. The reaction mixture was cooled to room temperature, the reaction mixture was concentrated under reduced pressure to remove phosphorus oxychloride. The residue was concentrated and dried. The residue was dissolved with dichloromethane (500 mL) and washed with water (500 mL). The separated organic phase was dried over anhydrous sodium sulfate, filtered, and the filtrate was concentrated under reduced pressure. The residue was purified by silica gel column chromatography (petroleum ether:dichloromethane=3:1) to deliver a pale yellow solid 19-e (2.5 g, yield: 40%). LC-MS (ESI): m/z=277 [M+H]$^+$.

Preparation of Compound 19-d.

Compound 19-e (1.2 g, 4.35 mmol) was dissolved in dichloromethane (5 mL) and then ammonia (50 mL, 7 M in methanol), was added and the reaction mixture was stirred at room temperature for 16 hours. The reaction mixture was concentrated under reduced pressure and the residue was added to water (50 mL), a solid was precipitated and filtered. The filter cake was washed with water (50 mL) and dried in vacuo to deliver a yellow solid 19-d (1.5 g, yield: 100%). This product was used directly for the next step without further purification.

Preparation of Compound 19-c.

Compound 19-d (1.5 g, 5.84 mmol) was dissolved in tetrahydrofuran (20 mL) and tertamyl nitrite (2.7 g, 23.36 mmol) was added. The reaction mixture was heated at 70° C. for 18 hours and the reaction mixture was concentrated under reduced pressure. The residue was purified by silica gel column chromatography (petroleum ether:dichloromethane=3:1) to deliver a pale yellow solid 19-c (0.79 g, yield: 56%). LC-MS (ESI): m/z=243 [M+H]$^+$.

Preparation of Compound 19-b.

Compound 19-c (300 mg, 1.24 mmol), compound 1-c (384 mg, 1.24 mmol), [1,1'-bis(diphenylphosphino)ferrocene]dichloropalladium(II) (144 mmol, 0.17 mmol) and sodium carbonate (396 mg, 3.74 mmol) were dissolved in 1,4-dioxane (5 mL) and water (5 mL). The reaction mixture was replaced with nitrogen three times to remove the oxygen inside the system and then heated at 90° C. for 30 minutes. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (dichloromethane:methanol=100:1) to deliver a pale yellow solid 19-b (158 mg, yield: 37%). LC-MS (ESI): m/z=348 [M+H]$^+$.

Preparation of Compound 19-a.

Compounds 19-b (100 mg, 0.29 mmol), compound 1-f (132 mg, 0.43 mmol), cesium carbonate (280 mg, 0.86 mmol), palladium acetate (102 mg, 0.46 mmol) and 4,5-bis(diphenylphosphino)-9,9-dimethylxanthene (332 mg, 0.58 mmol) were dissolved in dioxane (2 mL). The reaction mixture was replaced with nitrogen three times to remove the oxygen from the system and then heated at 110° C. for 40 minutes. The reaction mixture was cooled to room temperature and the reaction mixture was filtered through diatomite. The filter cake was washed with dichloromethane (50 mL×3) and the combined filtrates were concentrated under reduced pressure. The residue was purified by silica gel thin layer chromatography preparative plate (ether:ethyl acetate=1:1) to deliver a yellow solid 19-a (61 mg, yield: 35%). LC-MS (ESI): m/z=618 [M+H]$^+$.

Preparation of Compound 19.

Compound 19-a (61 mg, 0.1 mmol) was dissolved in dichloromethane (3 mL). The reaction solution was cooled to 0° C., trifluoroacetic acid (3 mL) was added, and the reaction mixture was stirred at room temperature for 16 hours. The reaction mixture was concentrated under reduced pressure and the residue was diluted with water (30 mL), the pH was adjusted to 10 with saturated aqueous sodium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by preparative high performance liquid chromatography (mobile phase: 10 mM ammonium bicarbonate aqueous solution:acetonitrile=35%-65%) to deliver a yellow solid 19 (30 mg, yield: 59%). LC-MS (ESI): m/z=518 [M+H]$^+$.

$^1$H-NMR (400 MHz, CDCl$_3$) δ: 9.09 (s, 1H), 7.99 (d, J=8 Hz, 1H), 7.92 (s, 1H), 7.85 (dd, J=5 Hz, J=2 Hz, 1H), 7.76 (dd, J=5 Hz, J=2 Hz, 1H), 7.40-7.61 (m, 5H), 6.70 (d, J=2 Hz, 1H), 6.40 (dd, J=5 Hz, J=2 Hz, 1H), 3.87 (s, 3H), 3.21 (m, 2H), 2.92 (s, 3H), 2.72-2.78 (m, 2H), 2.52-2.57 (m, 4H), 1.79-1.82 (m, 2H), 1.63-1.70 (m, 2H) ppm.

Example 20

N-[2-methoxy-4-(piperidin-4-yl)phenyl]-8-(2-methoxyphenyl)quinazolin-2-amine (Compound 20)

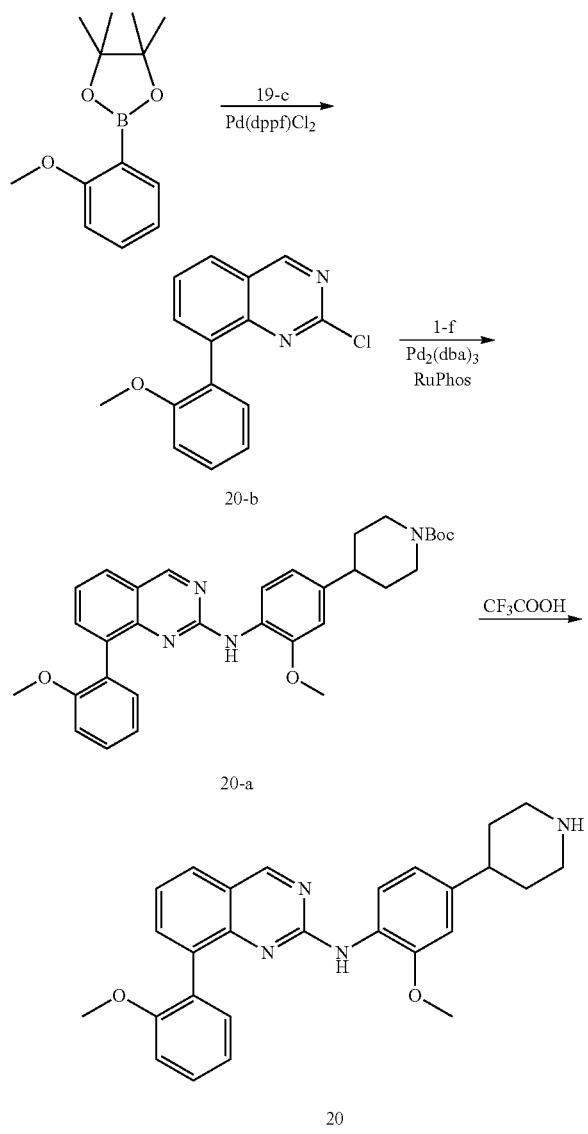

Preparation of Compound 20-b.

Compound 19-c (600 mg, 2.48 mmol), 2-methoxybenzeneboronicacid pinacol ester (415 mg, 2.73 mmol), [1,1'-bis(diphenylphosphino)ferrocene]dichloropalladium(II) (204 mg, 0.25 mmol) and sodium carbonate (804 mg, 7.44 mmol) were dissolved in 1,4-dioxane (5 mL) and water (3 mL). The reaction mixture was replaced with nitrogen three times to remove the oxygen inside the system and then heated at 80° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:dichloromethane=3:1) to deliver a white solid 20-b (450 mg, yield: 67%). LC-MS (ESI): m/z=271 [M+H]$^+$.

Preparation of Compound 20-a.

Compound 19-b (150 mg, 0.37 mmol), compound 1-f (255 mg, 0.56 mmol), cesium carbonate (362 mg, 1.11 mmol), tris(dibenzylideneacetone)dipalladium (64 mg, 0.12 mmol) and 2,2'-bis(diphenylphosphino)-1,1'-binaphthyl (75 mg, 0.12 mmol) were dissolved in dioxane (3 mL). The reaction mixture was replaced with nitrogen for three times to remove the oxygen inside the system and then heated at 110° C. for 2 hours. The reaction mixture was cooled to room temperature and the reaction mixture was filtered through diatomite. The filter cake was washed with dichloromethane (50 mL) and the combined filtrates were concentrated under reduced pressure. The residue was purified by silica gel thin layer chromatography preparative plate (petroleum ether:ethyl acetate=3:1) to deliver a yellow solid 20-a (98 mg, yield: 33%). LC-MS (ESI): m/z=541 [M+H]$^+$.

Preparation of Compound 20.

Compound 20-a (98 mg, 0.18 mmol) was dissolved in dichloromethane (3 mL). The reaction solution was cooled to 0° C., trifluoroacetic acid (3 mL) was added, and the reaction mixture was stirred at room temperature for 4 hours. The reaction mixture was concentrated under reduced pressure and the residue was diluted with water (30 mL), the pH was adjusted to 10 with saturated aqueous sodium carbonate solution. The aqueous phase was extracted with dichloromethane (50 mL×3). The combined organic phases were washed with water (20 mL×3) and brine (20 mL), dried over anhydrous sodium sulfate, filtered, the filtrate was concentrated under reduced pressure, and the residue was purified by silica gel thin layer chromatography preparative plate (dichloromethane:methanol=10:1) to deliver a yellow solid 20 (22 mg, yield: 28%). LC-MS (ESI): m/z=441 [M+H]$^+$.
$^1$H-NMR (400 MHz, CDCl$_3$) δ: 9.09 (s, 1H), 8.35 (d, J=8 Hz, 1H), 7.95 (s, 1H), 7.78 (dd, J=8 Hz, J=2 Hz, 1H), 7.75 (dd, J=8 Hz, J=2 Hz, 1H), 7.49-7.53 (m, 1H), 7.38-7.41 (m, 2H), 7.10-7.14 (m, 1H), 6.71 (d, J=2 Hz, 1H), 6.53 (dd, J=8 Hz, J=2 Hz, 1H), 3.88 (s, 3H), 3.68 (s, 3H), 3.58 (m, 2H), 3.02 (m, 2H), 2.69 (m, 1H), 1.99-2.14 (m, 4H) ppm.

Example 21

N-[2,2-dimethyl-4-(piperidin-4-yl)-2,3-dihydro-1-benzofuran-7-yl]-6-fluoro-8-(2-methoxyphenyl)quinazolin-2-amine (Compound 21)

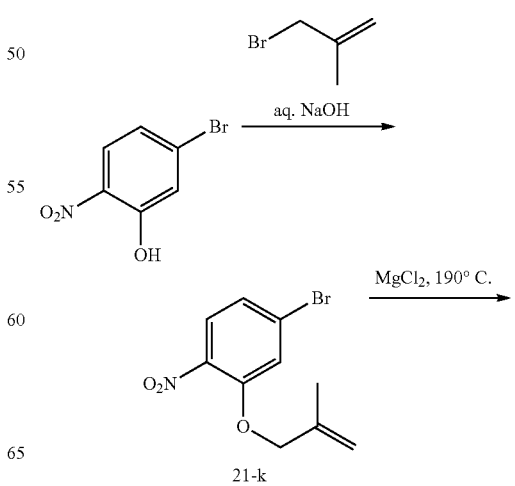

71
-continued
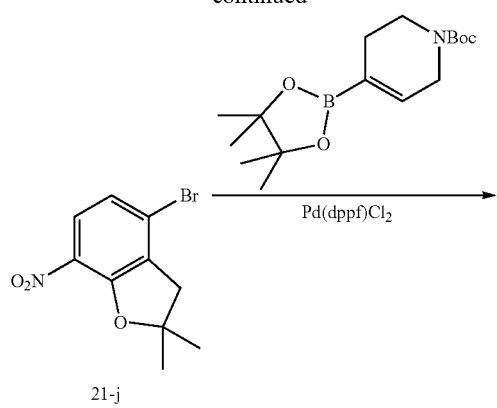
21-j
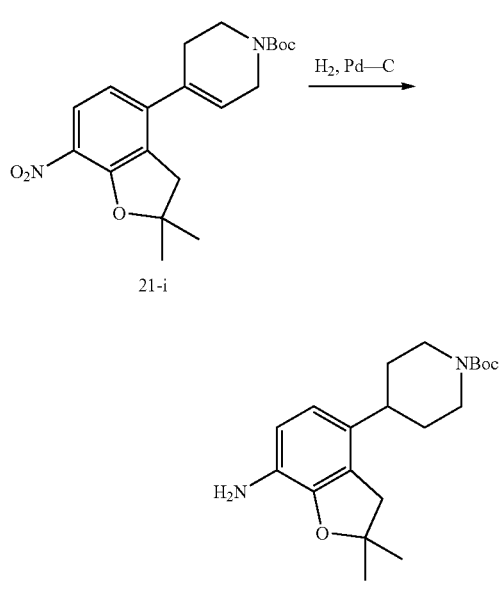
21-i
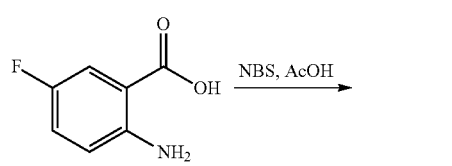
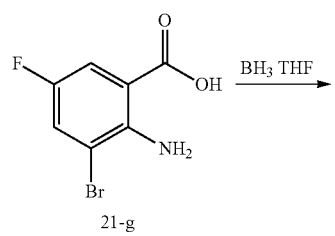
21-g
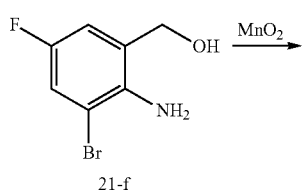
21-f
72
-continued
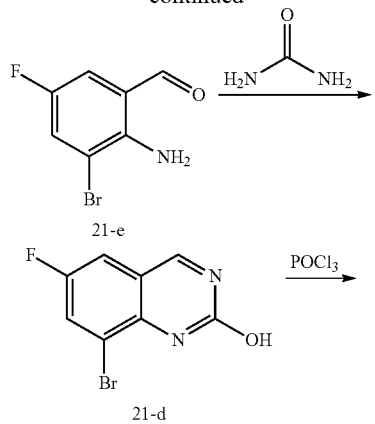
21-e
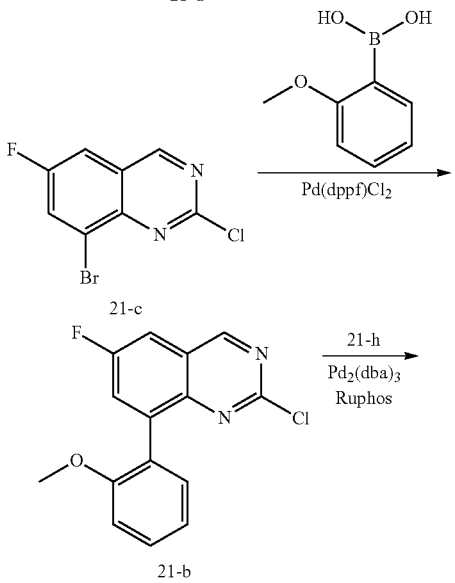
21-c, 21-d, 21-b
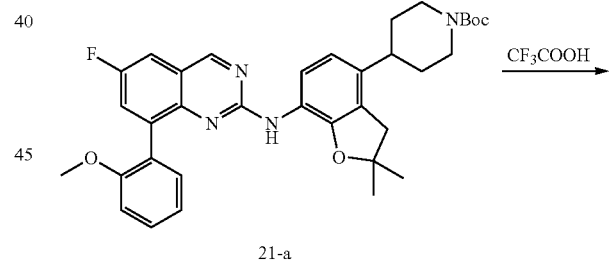
21-a
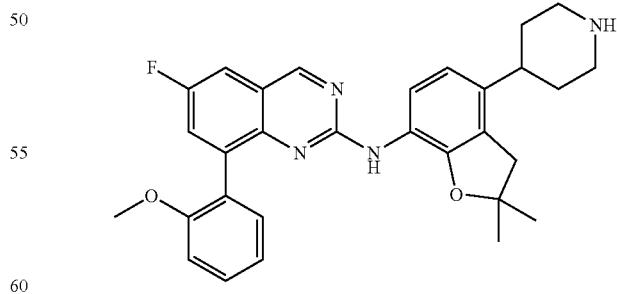
21
Preparation of Compound 21-k.
2-Nitro-5-bromophenol (1.0 g, 4.61 mmol) was dissolved in water (10 mL) and then sodium hydroxide (185 mg, 4.61 mmol) and 3-bromo-2-methylpropene (803 mg, 5.99 mmol)

were added to the above solution, respectively. The mixture was heated at 60° C. for 5 hours and the reaction mixture was cooled to room temperature and then diluted with ethyl acetate (50 mL). The separated organic phase was washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=10:1) to deliver a yellow solid 21-k (1.1 g, yield: 88%). LC-MS (ESI): m/z=599 $[M+H]^+$.

$^1$H-NMR (400 MHz, CDCl$_3$) δ: 7.75 (d, J=9 Hz, 1H), 7.21 (d, J=2 Hz, 1H), 7.17 (dd, J=9 Hz, J=2 Hz, 1H), 5.17 (s, 1H), 5.06 (t, J=2 Hz, 1H), 4.56 (s, 2H), 1.85 (s, 3H) ppm.

Preparation of Compound 21-j.

Compound 21-k (1.1 g, 4.06 mmol) and anhydrous magnesium chloride (110 mg) were mixed and the mixture was heated to 190° C. and reacted for 3 hours, then the mixture was cooled to room temperature and added with ethyl acetate (50 mL), a solid was precipitated. The mixture was filtered and the filtrate was concentrated under reduced pressure. The residue was purified by silica gel column chromatography (petroleum ether:ethyl acetate=10:1) to deliver a white solid 21-j (1.1 g, yield: 100%).

Preparation of Compound 21-i.

The compound 21-j (1.1 g, 4.06 mmol), N-Boc-1,2,3,6-tetrahydropyridine-4-boronic acid pinacol ester (1.51 g, 48.77 mmol), [1,1'-bis(diphenylphosphino)ferrocene]dichloropalladium(II) (341 mg, 0.43 mmol) and sodium carbonate (1.3 g, 12.25 mmol) were dissolved in 1,4-dioxane (15 mL) and water (15 mL). The reaction mixture was replaced with nitrogen three times to remove the oxygen inside the system and then heated at 80° C. for 16 hours. The reaction mixture was cooled to room temperature, diluted with ice water (100 mL) and extracted with dichloromethane (50 mL×3). The combined organic phases were washed successively with water (50 mL×3) and brine (50 mL), dried over anhydrous sodium sulfate, filtered, and the filtrate was concentrated under reduced pressure. The residue was purified by silica gel column chromatography (petroleum ether:ethyl acetate=5:1) to deliver a pale yellow solid 21-i (565 mg, yield: 37%).

$^1$H-NMR (400 MHz, CDCl$_3$) δ: 7.90 (d, J=9 Hz, 1H), 8.08 (d, J=9 Hz, 1H), 6.77 (d, J=9 Hz, 1H), 5.88 (s, 1H), 4.08-4.11 (m, 2H), 3.61-3.64 (m, 2H), 3.09 (s, 2H), 2.44 (s, 2H), 1.50 (s, 9H) ppm.

Preparation of Compound 21-h.

Compound 21-i (565 mg, 1.51 mmol) and 10% palladium-carbon (150 mg) were dissolved in ethanol (20 mL). The reaction mixture was replaced with hydrogen three times and then hydrogenated at room temperature for 16 hours. The reaction mixture was filtered to remove palladium-carbon and the filtrate was concentrated under reduced pressure to deliver a purple oil 21-h (435 mg, yield: 84%), this product was used without further purification. LC-MS (ESI): m/z=291 $[M+H]^+$.

Preparation of Compound 21-g.

2-Amino-5-fluorobenzoic acid (20 g, 129 mmol) was dissolved in acetic acid (250 mL) at 0° C., and then N-bromosuccinimide (25 g, 140 mmol) was added in batches to the above solution. The mixture was stirred at room temperature for 16 hours and then filtered. The filter cake was washed with petroleum ether (100 mL×3). The filter cake was dried in vacuo to deliver a white solid 21-g (18.8 g, yield: 62%), this product was used without further purification. LC-MS (ESI): m/z=234 $[M+H]^+$.

Preparation of Compound 21-f.

Borane/tetrahydrofuran solution (240 mL, 240 mmol) was added dropwise to a solution of compound 21-g (18.8 g, 80 mmol) in tetrahydrofuran (160 mL) at 0° C., and the reaction mixture was stirred at room temperature for 16 hours. Methanol (10 mL) was added to the reaction mixture to quench the reaction, and then the reaction mixture was concentrated under reduced pressure to remove the organic solvent. The residue was washed with ethyl acetate (200 mL) and the solution was washed successively with water (50 mL×3) and brine (50 mL), dried over anhydrous sodium sulfate, filtered and the filtrate was concentrated under reduced pressure to deliver a white solid 21-f (17.2 g, yield: 97%). LC-MS (ESI): m/z=220 $[M+H]^+$.

Preparation of Compound 21-e.

Manganese dioxide (34 g, 390 mmol) was added in batches to a solution of compound 21-f (17.2 g, 78 mmol) in chloroform (300 mL) at 0° C., and the reaction mixture was stirred at room temperature for 16 hours. The reaction mixture was filtered and the filtrate was concentrated under reduced pressure to deliver a white solid 21-e (16.5 g, yield: 95%), this product was used without further purification. LC-MS (ESI): m/z=218 $[M+H]^+$.

Preparation of Compound 21-d.

Compound 21-f (16.5 g, 76 mmol) was mixed with urea (64 g, 1070 mmol) and the mixture was heated at 185° C. for 30 minutes. The reaction mixture was cooled to room temperature and then water (200 mL) was added and stirred for 30 minutes. The reaction mixture was filtered and the filter cake was dried in vacuo to deliver a white solid 21-d (18 g, yield: 97%), this product was used without further purification. LC-MS (ESI): m/z=243 $[M+H]^+$.

Preparation of Compound 21-c.

Compound 21-d (18 g, 74 mmol) was dissolved in phosphorus oxychloride (120 mL, 860 mmol) at 0° C., and the reaction mixture was heated at 105° C. for 16 hours. The reaction mixture was cooled to room temperature, concentrated to remove phosphorus oxychloride under reduced pressure, and the residue was added to water (100 mL) and stirred. The reaction mixture was filtered and the filter cake was dried in vacuo to deliver a white solid 21-c (5 g, yield: 26%), this product was used without further purification. LC-MS (ESI): m/z=261 $[M+H]^+$.

Preparation of Compound 21-b.

Compound 21-c (1.03 g, 3.93 mmol), o-methoxyphenylboronic acid (600 mg, 3.95 mmol), [1,1'-bis(diphenylphosphino)ferrocene]dichloropalladium(II) (150 mg, 0.2 mmol) and sodium carbonate (1.2 g, 11.3 mmol) were dissolved in 1,4-dioxane (30 mL) and water (10 mL). The reaction mixture was replaced with nitrogen three times to remove the oxygen inside the system and then heated at 120° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=5:1) to deliver a white solid 21-b (0.49 g, yield: 43%). LC-MS (ESI): m/z=599 $[M+H]^+$.

Preparation of Compound 21-a.

Compound 21-b (140 mg, 0.48 mmol), compound 21-h (112 mg, 0.32 mmol), potassium carbonate (220 mg, 1.6 mmol), tris(dibenzylideneacetone)dipalladium (11 mg, 0.023 mmol) were dissolved in N,N-dimethylformamide (10 mL), and the reaction mixture was replaced with nitrogen three times to remove the oxygen inside the system and then heated at 130° C. for 16 hours. The reaction mixture was cooled to room temperature, diluted with ice water (10 mL) and extracted with dichloromethane (50 mL×3). The combined organic phases were washed successively with water (20 mL×3), and brine (20 mL), dried over anhydrous sodium sulfate, filtered, and the filtrate was concentrated under reduced pressure. The residue was purified by silica gel column chromatography (petroleum ether:ethyl acetate=5:1) to deliver a yellow solid 21-a (120 mg, yield: 42%). LC-MS (ESI): m/z=499 [M+H]$^+$.

Preparation of Compound 21.

Compound 21-a (120 mg, 0.2 mmol) was dissolved in dichloromethane (10 mL). The reaction solution was cooled to 0° C., trifluoroacetic acid (5 mL, 43 mmol) was added and the reaction mixture was stirred at room temperature for 30 minutes. The reaction mixture was concentrated under reduced pressure and the residue was diluted with water (30 mL). The pH was adjusted to 10 with potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether: ethyl acetate=2:1) to deliver a yellow solid 21 (20 mg, yield: 20%). LC-MS (ESI): m/z=499 [M+H]$^+$.

$^1$H-NMR (400 MHz, CD$_3$OD) δ: 9.17 (s, 1H), 7.95 (d, J=8.4 Hz, 1H), 7.59 (s, 1H), 7.56 (s, 1H), 7.52-7.47 (m, 1H), 7.37 (dd, J$_1$ 7.6 Hz, J$_2$=1.6 Hz, 1H), 7.16 (d, J=8.4 Hz, 1H), 7.11 (t, J=7.4 Hz, 1H), 6.40 (d, J=8.4 Hz, 1H), 3.69 (s, 3H), 3.53-3.46 (m, 2H), 3.16-3.08 (m, 4H), 2.85-2.76 (m, 1H), 2.05-1.97 (m, 2H), 1.95-1.83 (m, 2H) ppm.

Example 22

6-Fluoro-8-(2-methoxyphenyl)-N-[4-(piperidin-4-yl)-2,3-dihydro-1-benzofuran-7-yl]quinazoline-2-amine (Compound 22)

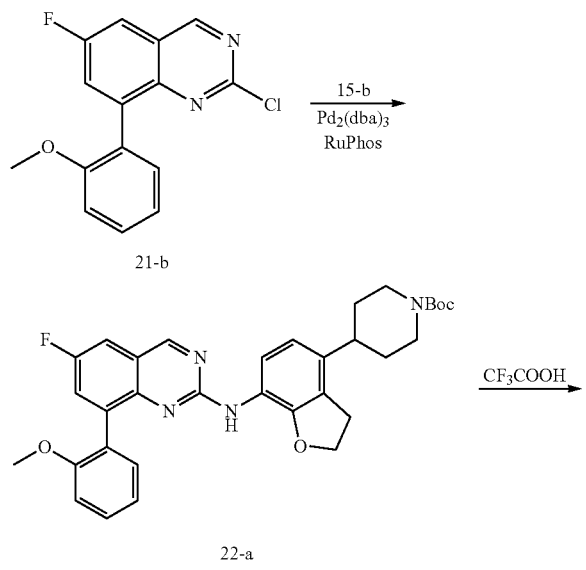

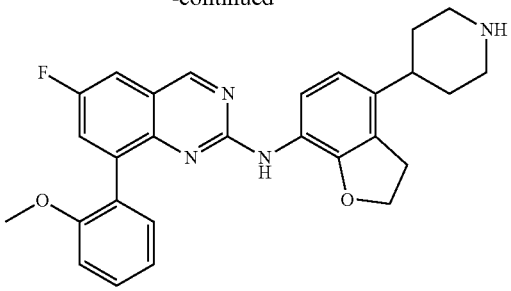

Preparation of Compound 22-a.

Compound 21-b (170 mg, 0.59 mmol), compound 15-b (190 mg, 0.60 mmol), tris(dibenzylideneacetone)dipalladium (20 mg, 0.02 mmol), potassium carbonate (250 mg, 1.8 mg) and 2-dicyclohexylphosphino-2',6'-di-iso-propoxy-1,1'-biphenyl (10 mg, 0.02 mmol) were dissolved in N,N-dimethylformamide (10 mL), and the reaction mixture was replaced with nitrogen three times to remove the oxygen inside the system and then heated at 130° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered and the filtrate was concentrated under reduced pressure. The residue was purified by silica gel column chromatography (petroleum ether:ethyl acetate=5:1) to deliver a yellow solid 22-a (200 mg, yield: 59%). LC-MS (ESI): m/z=571 [M+H]$^+$.

Preparation of Compound 22.

Compound 22-a (200 mg, 0.35 mmol) was dissolved in dichloromethane (10 mL). The reaction solution was cooled to 0° C., trifluoroacetic acid (5 mL, 43 mmol) was added and the reaction mixture was stirred at room temperature for 30 minutes. The reaction mixture was concentrated under reduced pressure and the residue was diluted with water (30 mL). The pH was adjusted to 10 with potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether: ethyl acetate=2:1) to deliver a yellow solid 22 (70 mg, yield: 42%). LC-MS (ESI): m/z=471 [M+H]$^+$.

$^1$H-NMR (400 MHz, CDCl$_3$) δ: 9.02 (s, 1H), 8.00 (d, J=8.4 Hz, 1H), 7.59-7.56 (m, 1H), 7.52-7.47 (m, 1H), 7.41 (d, J=6.8 Hz, 1H), 7.36-7.32 (m, 2H), 7.13-7.07 (m, 2H), 6.46 (d, J=8.4 Hz, 1H), 4.60 (t, J=8.8 Hz, 1H), 3.69 (s, 3H), 3.25-3.15 (m, 4H), 2.72 (t, J=8.8 Hz, 1H), 2.57-2.45 (m, 1H), 1.78-1.64 (m, 4H) ppm.

Example 23

8-(2-Methoxyphenyl)-N-[4-(piperidin-4-yl)-2,3-dihydro-1-benzofuran-7-yl]quinazolin-2-amine (Compound 23)

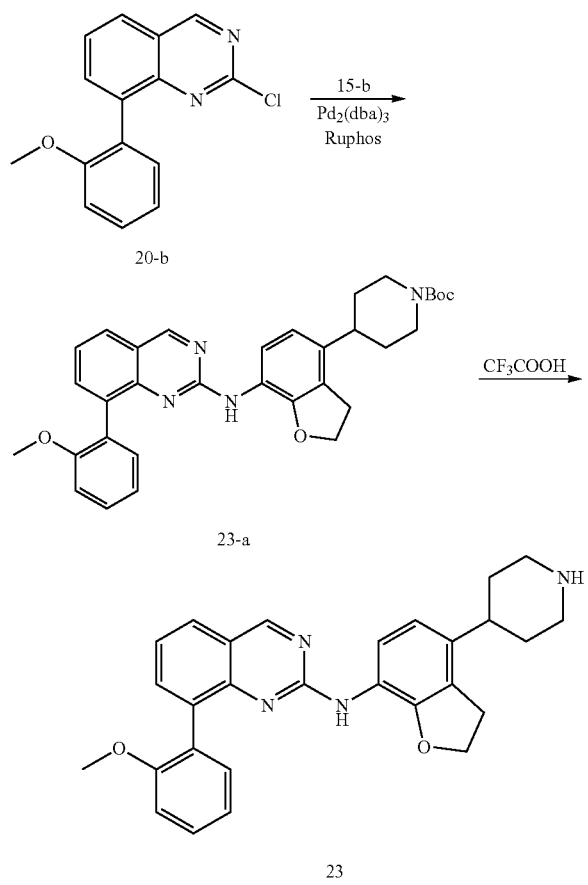

Preparation of Compound 23-a.

Compound 20-b (170 mg, 0.59 mmol), compound 15-b (160 mg, 0.5 mmol), potassium carbonate (140 mg, 1 mmol), tris(dibenzylideneacetone)dipalladium(46 mg, 0.05 mmol) and 2-dicyclohexylphosphino-2',6'-di-iso-propoxy-1,1'-biphenyl(24 mg, 0.05 mmol) were dissolved in N,N-dimethylformamide (5 mL), the reaction mixture was replaced with nitrogen three times to remove the oxygen inside the system and then heated at 110° C. for 16 hours. The reaction mixture was cooled to room temperature and the reaction mixture was filtered through diatomite. The filter cake was washed with dichloromethane (50 mL×3). The combined filtrates were washed with water (20 mL×3), dried over anhydrous sodium sulfate, filtered, and concentrated under reduced pressure. The residue was purified by silica gel thin layer chromatography preparative plate (petroleum ether:ethyl acetate=1:1) to deliver a pale yellow solid 23-a (161 mg, yield: 58%). LC-MS (ESI): m/z=553 [M+H]+.

Preparation of Compound 23.

Compound 23-a (160 mg, 0.29 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure, and the residue was dissolved with ethyl acetate (50 mL), and then 1 M aqueous hydrochloric acid solution (30 mL) was added. The pH of the separated aqueous phase was adjusted to 10 with saturated aqueous potassium carbonate solution, a solid was precipitated, filtered, the filter was washed with water (50 mL×3) and then dried in vacuo to deliver a pale yellow solid 23 (62 mg, yield: 47.3%). LC-MS (ESI): m/z=453 [M+H]+.

1H-NMR (400 MHz, CDCl3) δ: 9.06 (s, 1H), 8.06 (d, J=8 Hz, 1H), 7.76 (d, J=8 Hz, 1H), 7.71 (d, J=8 Hz, 1H), 7.43 (m, 4H), 7.10 (m, 2H), 6.46 (d, J=8 Hz, 1H), 6.56 (d, J=8 Hz, 1H), 4.60 (t, J=8 Hz, 2H), 3.68 (s, 3H), 3.21 (t, J=8 Hz, 2H), 3.20 (m, 2H), 2.73 (t, J=8 Hz, 2H), 2.53 (m, 1H), 1.73 (m, 4H) ppm.

Example 24

N-[2,2-Dimethyl-4-(piperidin-4-yl)-2,3-dihydro-1-benzofuran-7-yl]-8-(2-methoxyphenyl)quinazolin-2-amine (Compound 24)

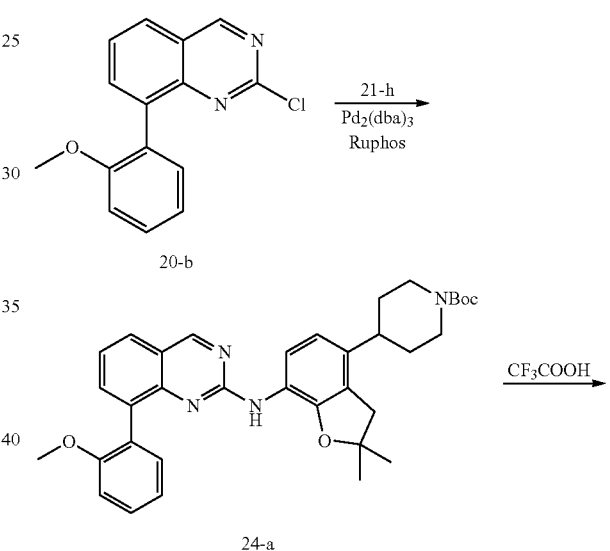

Preparation of Compound 24-a.

Compound 21-h (143 mg, 0.41 mmol), 20-b (120 mg, 0.41 mmol), cesium carbonate (401 mg, 1.23 mmol), tris (dibenzylideneacetone)dipalladium (71 mg, 0.13 mmol) and 2-dicyclohexylphosphino-2',6'-di-iso-propoxy-1,1'-biphenyl (58 mg, 0.13 mmol) were dissolved in N,N-dimethylformamide (3 mL), the reaction solution was replaced with nitrogen three times to remove the oxygen inside the system and then heated at 110° C. for 16 hours. The reaction mixture was cooled to room temperature and filtered through diatomite. The filter cake was washed with dichloromethane (50 mL×3) and the filtrate was washed successively with water (50 mL×3) and brine (50 mL), dried over anhydrous sodium sulfate, filtered, the filtrate was concentrated under reduced pressure, and the residue was purified by silica gel thin layer chromatography preparative plate (petroleum ether:ethyl acetate=3:1) to deliver a pale yellow solid 24-a (98 mg, yield: 40%). LC-MS (ESI): m/z=601 [M+H]+.

Preparation of Compound 24.

Compound 24-a (98 mg, 0.16 mmol) was dissolved in dichloromethane (3 mL). The reaction solution was cooled to 0° C., trifluoroacetic acid (3 mL, 25.8 mmol) was added and the reaction mixture was stirred at room temperature for 3 hours. The reaction mixture was concentrated under reduced pressure and the residue was dissolved in dichloromethane (50 mL) and diluted with saturated aqueous sodium carbonate solution (50 mL). The organic phase was separated, dried over anhydrous sodium sulfate, filtered, and the filtrate was concentrated under reduced pressure. The residue was purified by silica gel thin layer chromatography preparative plate (dichloromethane:methanol=10:1) to deliver a pale yellow solid 24 (35 mg, yield: 43%). LC-MS (ESI): m/z=501 [M+H]+.

$^1$H-NMR (400 MHz, CDCl$_3$) δ: 8.76 (s, 1H), 8.21 (d, J=8 Hz, 1H), 7.45-7.50 (m, 1H), 7.40 (dd, J=8 Hz, J=2 Hz, 1H), 7.23 (s, 1H), 7.12-7.15 (m, 1H), 7.08 (d, J=8 Hz, 1H), 6.56 (d, J=8 Hz, 1H), 3.79 (s, 3H), 3.56 (m, 2H), 3.03 (s, 2H), 2.98 (m, 2H), 2.63 (m, 1H), 2.50 (s, 3H), 2.13 (m, 2H), 1.97 (m, 2H), 1.47 (s, 6H) ppm.

Example 25

8-(2-Methoxyphenyl)-N-[3-(piperidin-4-yl)-1-isopropyl-1H-pyrazol-5-yl]quinazolin-2-amine (Compound 25)

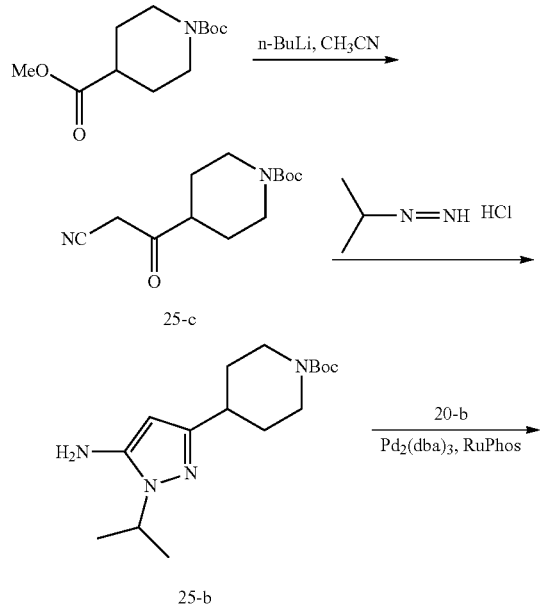

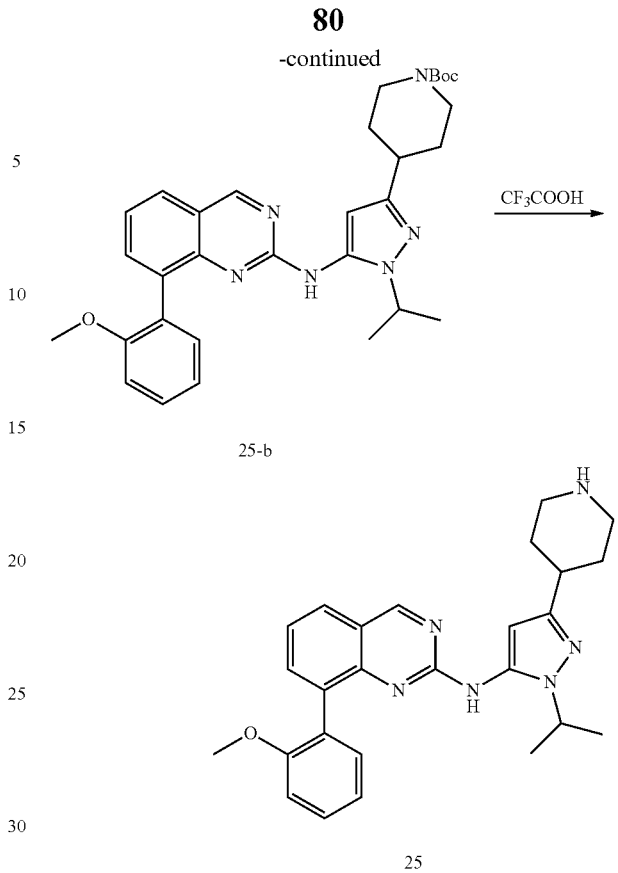

Preparation of Compound 25-c.

Anhydrous acetonitrile (1.18 g, 28.81 mmol) was dissolved in anhydrous tetrahydrofuran (50 mL) and the reaction solution was cooled to −78° C. And then n-butyllithium (11.5 mL, 28.75 mmol, 2.5 M solution in n-hexane) was added dropwise to the above solution, and after the addition, the stirring was continued for 4 hours. A solution of N-Boc-piperidine-4-carboxylic acid methyl ester (7.0 g, 28.81 mmol) in anhydrous tetrahydrofuran (50 mL) was added dropwise to the above reaction mixture. The reaction mixture was stirred at −78° C. for 30 minutes and slowly warmed to room temperature. And the stirring was continued for 2 hours. Then the reaction mixture was diluted with saturated aqueous ammonium chloride solution (100 mL). The mixed solution was extracted with ethyl acetate (50 mL×3). The combined organic phases were washed successively with water (50 mL×3) and brine (50 mL), dried over anhydrous sodium sulfate, filtered, the filtrate was concentrated under reduced pressure. The residue was purified by silica gel column chromatography (petroleum ether:ethyl acetate=5:1) to deliver a pale yellow solid 25-c (3.1 g, yield: 42%). LC-MS (ESI): m/z=197 [M+H-t-Bu]+.

Preparation of Compound 25-b.

Compound 25-c (1.6 g, 6.35 mmol) and isopropylhydrazine hydrochloride (769 mg, 6.99 mmol) were dissolved in anhydrous ethanol (20 mL) and triethylamine (962 mg, 9.53 mmol) was then added thereto. The reaction mixture was heated under reflux for 16 hours and then cooled to room temperature. The reaction mixture was concentrated under reduced pressure and the residue was dissolved in ethyl acetate (100 mL) and then washed successively with water (50 mL×3) and brine (50 mL), dried over anhydrous sodium sulfate, filtered and the filtrate was concentrated under reduced pressure to deliver a pale yellow solid 25-b (1.3 g, yield: 67%). This product was used without further purification. LC-MS (ESI): m/z=309 [M+H]+.

Preparation of Compound 25-a.

Compound 25-b (189 mg, 0.62 mmol), 20-b (150 mg, 0.56 mmol), tris(dibenzylideneacetone)dipalladium (97 mg, 0.17 mmol), potassium carbonate (232 mg, 1.68 mmol), and 2-dicyclohexylphosphino-2',6'-di-iso-propoxy-1,1'-biphenyl (78 mg, 0.17 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature, diluted with ethyl acetate (50 mL) and ice water (50 mL) and extracted with ethyl acetate (50 mL×2). The combined organic phases were washed with water (50 mL×3) and saturated (50 mL), dried over anhydrous sodium sulfate, filtered, and the filtrate was concentrated under reduced pressure. The residue was purified by silica gel thin layer chromatography preparative plate (petroleum ether:ethyl acetate=3:1) to deliver a pale yellow solid 25-a (208 mg, yield: 69%). LC-MS (ESI): m/z=543 [M+H]+.

Preparation of Compound 25.

Compound 25-a (208 mg, 0.38 mmol) was dissolved in dichloromethane (3 mL). The reaction solution was cooled to 0° C., trifluoroacetic acid (3 mL, 25.8 mmol) was added and the reaction was stirred at room temperature for 3 hours. The reaction was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a yellow solid 25 (130 mg, yield: 76%). LC-MS (ESI): m/z=543 [M+H]+.

$^1$H-NMR (400 MHz, CD$_3$OD) δ: 9.21 (s, 1H), 7.87 (dd, J=8 Hz, J=2 Hz, 1H), 7.69 (dd, J=8 Hz, J=2 Hz, 1H), 7.38-7.46 (m, 2H), 7.25-7.27 (dd, J=8 Hz, J=2 Hz, 1H), 7.04-7.11 (m, 2H), 6.08 (s, 1H), 4.49-4.52 (m, 1H), 3.64 (s, 3H), 3.15-3.20 (m, 2H), 2.69-2.81 (m, 3H), 1.83-1.86 (m, 2H), 1.55-1.59 (m, 2H), 1.31 (d, J=7 Hz, 6H) ppm.

Example 26

6-Fluoro-8-(2-methoxyphenyl)-N-[3-(piperidin-4-yl)-1-isopropyl-1H-pyrazol-5-yl]quinazolin-2-amine (Compound 26)

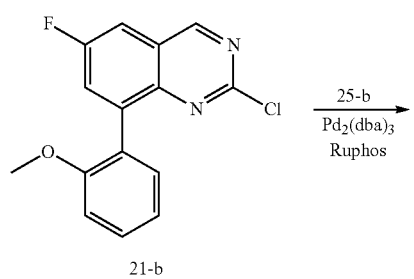

21-b

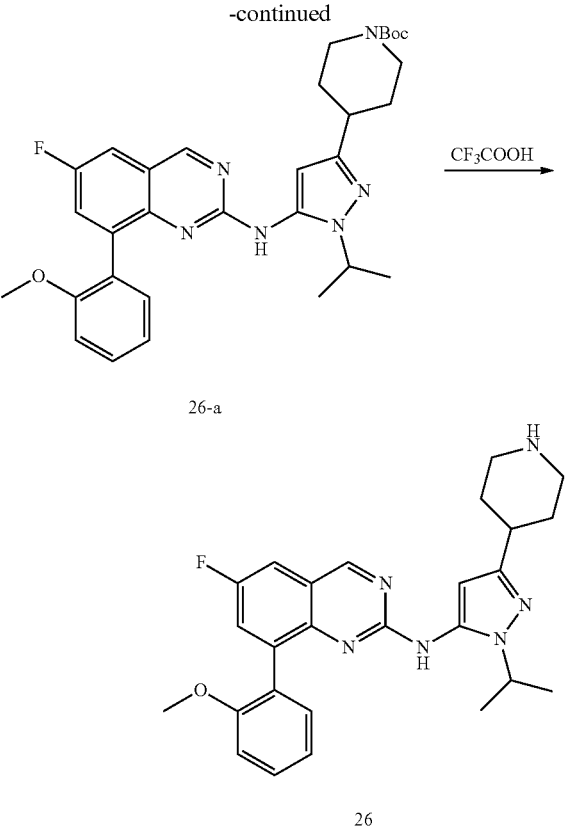

Preparation of Compound 26-a.

Compound 21-b (170 mg, 0.59 mmol), compound 25-b (160 mg, 0.52 mmol), tris(dibenzylideneacetone)dipalladium (20 mg, 0.02 mmol), potassium carbonate (210 mg, 1.5 mmol) and 2-dicyclohexylphosphino-2',6'-di-iso-propoxy-1,1'-biphenyl (10 mg, 0.02 mmol) were dissolved in N,N-dimethylformamide (10 mL), and the reaction mixture was replaced with nitrogen three times to remove the oxygen inside the system and then heated at 130° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered and the filtrate was concentrated under reduced pressure. The residue was purified by silica gel column chromatography (petroleum ether:ethyl acetate=4:1) to deliver a yellow solid 26-a (200 mg, yield: 68%). LC-MS (ESI): m/z=561 [M+H]+.

Preparation of Compound 26.

Compound 26-a (200 mg, 0.35 mmol) was dissolved in dichloromethane (10 mL). The reaction solution was cooled to 0° C., trifluoroacetic acid (5 mL, 43 mmol) was added and the reaction was stirred at room temperature for 30 minutes. The reaction was concentrated under reduced pressure and the residue was diluted with water (30 mL). The pH was adjusted to 10 with potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=1:1) to deliver a yellow solid 26 (33 mg, yield: 20%). LC-MS (ESI): m/z=461 (M+H)+.

$^1$H-NMR (400 MHz, CDCl$_3$) δ: 9.07 (s, 1H), 7.57 (dd, J$_1$=9.2 Hz, J$_2$=2.8 Hz, 1H), 7.45-7.32 (m, 3H), 7.09-7.02 (m, 2H), 6.93-6.85 (m, 1H), 6.04 (s, 1H), 4.34-4.25 (m, 1H), 3.67 (s, 3H), 3.21-3.12 (m, 2H), 2.77-2.65 (m, 3H), 1.88-1.80 (m, 2H), 1.55-1.45 (m, 2H), 1.35 (d, J=6.8 Hz, 1H) ppm.

Example 27

8-(4-Fluoro-2-methoxyphenyl)-N-[4-(piperidin-4-yl)-2,3-dihydro-1-benzofuran-7-yl]quinazoline-2-amine (Compound 27)

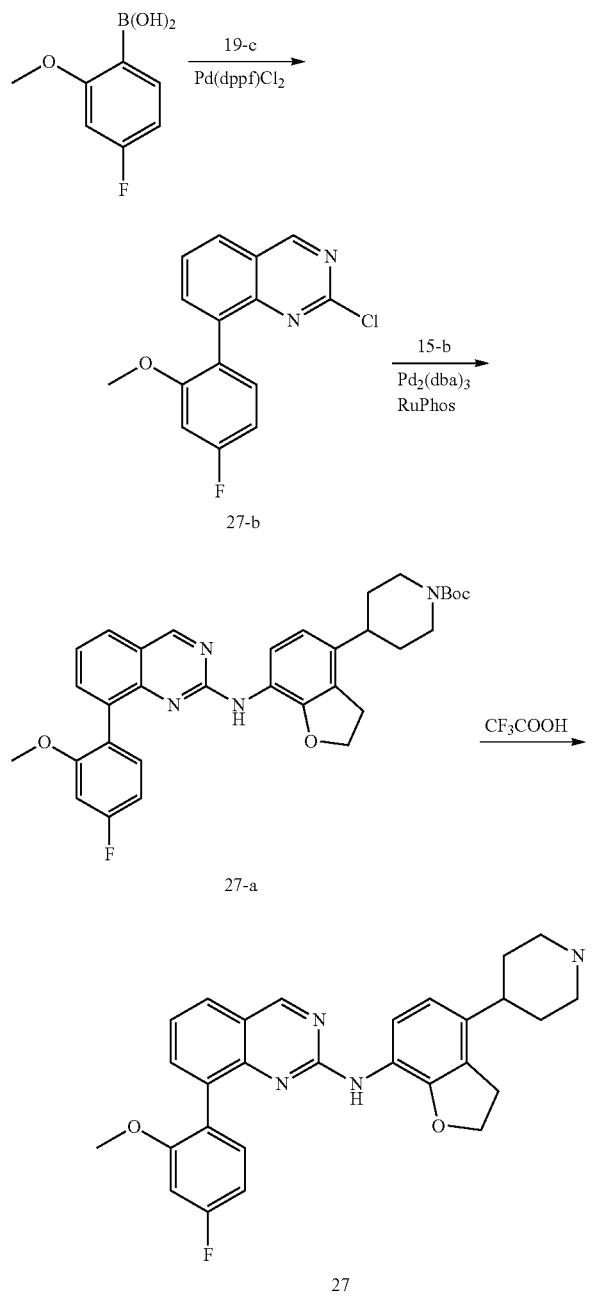

Preparation of Compound 27-b.

Compound 19-c (900 mg, 3.72 mmol), 2-methoxy-4-fluorobenzeneboronic acid (885 mg, 5.21 mmol), [1,1'-bis(diphenylphosphino)ferrocene]dichloropalladium(II) (245 mg, 1.16 mmol) and sodium carbonate (1.19 g, 11.16 mmol) were dissolved in 1,4-dioxane (5 mL) and water (5 mL). The reaction mixture was replaced with nitrogen three times to remove the oxygen inside the system and then heated at 80° C. for 16 hours. The reaction mixture was cooled to room temperature, diluted with ice water (50 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (dichloromethane:methanol=100:1) to deliver a white solid 27-b (335 mg, yield: 31%). LC-MS (ESI): m/z=289 [M+H]$^+$.

Preparation of Compound 27-a.

Compound 27-b (150 mg, 0.52 mmol), compound 15-b (166 mg, 0.52 mmol), potassium carbonate (216 mg, 1.56 mmol), tris(dibenzylideneacetone)dipalladium (90 mg, 0.16 mmol) and 2-dicyclohexylphosphino-2',6'-di-iso-propoxy-1,1'-biphenyl(73 mg, 0.16 mmol) were dissolved in N,N-dimethylformamide (3 mL), and the reaction mixture was replaced with nitrogen three times to remove the oxygen inside the system and then heated at 110° C. for 3 hours. The reaction mixture was cooled to room temperature, diluted with ice water (50 mL) and extracted with ethyl acetate (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=3:1) to deliver a pale yellow solid 27-a (98 mg, yield: 33%). LC-MS (ESI): m/z=571 [M+H]$^+$.

Preparation of Compound 27.

Compound 27-a (98 mg, 0.17 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure, and the residue was dissolved with ethyl acetate (50 mL), and then 1 M aqueous hydrochloric acid solution (50 mL) was added. The pH of the separated aqueous phase was adjusted to 10 with saturated aqueous potassium carbonate solution, a solid was precipitated and filtered. The filter cake was washed with water (10 mL×3) and dried in vacuo to deliver a pale yellow solid 27 (31 mg, yield: 39%). LC-MS (ESI): m/z=471 [M+H]$^+$.

$^1$H-NMR (400 MHz, CD$_3$OD) δ: 9.16 (s, 1H), 7.94 (d, J=8 Hz, 1H), 7.85 (dd, J=1 Hz, J=8 Hz, 1H), 7.72 (dd, J=Hz, J=8 Hz, 1H), 7.42 (d, J=1 Hz, J=8 Hz, 1H), 7.31 (d, J=1 Hz, J=8 Hz, 1H), 6.92 (d, J=1 Hz, J=8 Hz, 1H), 6.82 (m, 1H), 6.47 (d, J=8 Hz, 1H), 4.62 (t, J=8 Hz, 2H), 3.64 (s, 3H), 3.26 (t, J=8 Hz, 2H), 3.31 (m, 2H), 2.92 (m, 2H), 2.73 (m, 1H), 1.76-1.89 (m, 4H) ppm.

Example 28

8-(4-Fluoro-2-methoxyphenyl)-N-[3-(piperidin-4-yl)-1-isopropyl-1H-pyrazol-5-yl]quinazolin-2-amine (Compound 28)

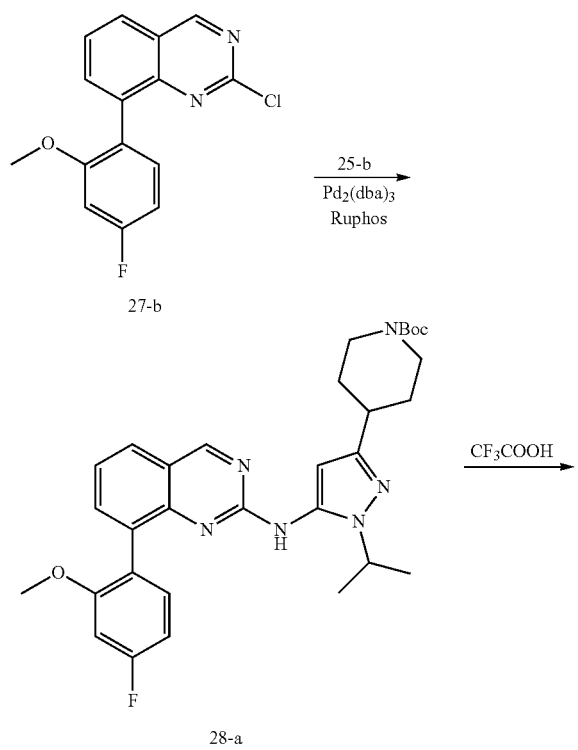

Preparation of Compound 28-a.

Compound 25-b (161 mg, 0.52 mmol), compound 27-b (150 mg, 0.52 mmol), tris(dibenzylideneacetone)dipalladium (90 mg, 0.16 mmol), potassium carbonate (216 mg, 1.56 mmol) and 2-dicyclohexylphosphino-2',6'-di-isopropoxy-1,1'-biphenyl (73 mg, 0.16 mmol) were dissolved in N,N-dimethylformamide (3 mL), and the reaction mixture was replaced with nitrogen three times to remove the oxygen inside the system and then heated at 110° C. for 3 hours. The reaction mixture was cooled to room temperature, diluted with ethyl acetate (50 mL) and ice water (50 mL) and extracted with ethyl acetate (50 mL×2). The combined organic phases were washed with water (50 mL×3) and brine (50 mL), dried over anhydrous sodium sulfate, filtered, and the filtrate was concentrated under reduced pressure. The residue was purified by silica gel thin layer chromatography preparative plate (petroleum ether:ethyl acetate=1:1) to deliver a pale yellow solid 28-a (128 mg, yield: 44%). LC-MS (ESI): m/z=561 [M+H]$^+$.

Preparation of Compound 28.

Compound 28-a (128 mg, 0.23 mmol) was dissolved in dichloromethane (3 mL). The reaction solution was cooled to 0° C., trifluoroacetic acid (3 mL, 25.8 mmol) was added and the reaction mixture was stirred at room temperature for 3 hours. The reaction mixture was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a yellow solid 28 (86 mg, yield: 82%). LC-MS (ESI): m/z=461 [M+H]$^+$.

$^1$H-NMR (400 MHz, MeOD) δ: 9.27 (s, 1H), 7.88 (dd, J=2 Hz, J=8 Hz, 1H), 7.70 (dd, J=2 Hz, J=8 Hz, 1H), 7.45 (m, 1H), 7.25 (m, 1H), 6.92 (m, 1H), 6.78 (m, 1H), 6.07 (s, 1H), 4.53 (s, 1H), 3.64 (m, 3H), 3.17 (m, 2H), 2.67-2.77 (m, 3H), 1.84 (m, 2H), 1.55 (m, 2H), 1.32 (d, J=8 Hz, 6H) ppm.

Example 29

8-(5-Fluoro-2-methoxyphenyl)-N-[4-(piperidin-4-yl)-2,3-dihydro-1-benzofuran-7-yl]quinazolin-2-amine (Compound 29)

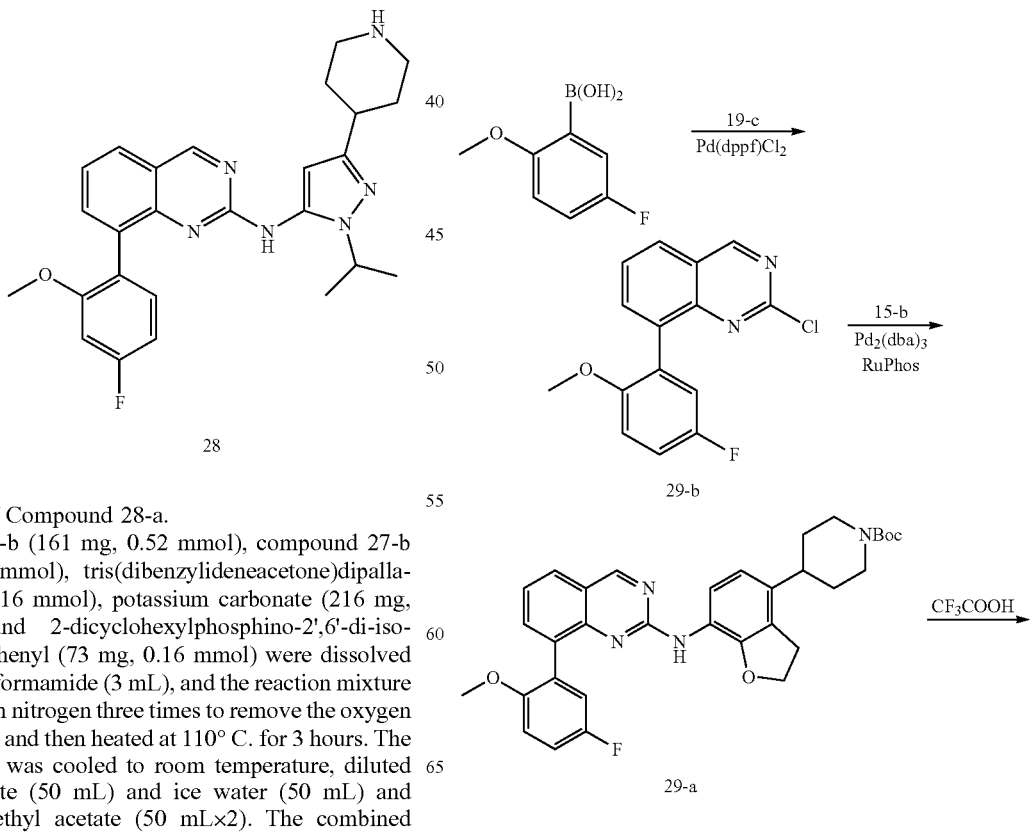

-continued

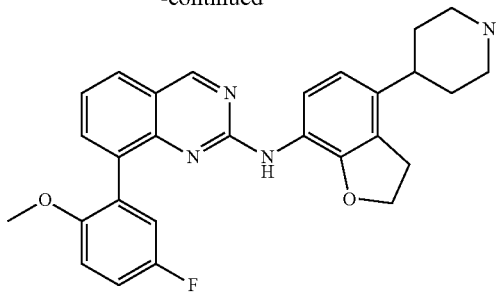

29

Preparation of Compound 29-b.

Compound 19-c (1.02 g, 4.20 mmol), 2-methoxy-5-fluorobenzeneboronic acid (1.0 g, 5.88 mmol), [1,1'-bis(diphenylphosphino)ferrocene]dichloropalladium(II) (343 mg, 0.42 mmol) and sodium carbonate (1.34 g, 12.6 mmol) were dissolved in 1,4-dioxane (10 mL) and water (10 mL). The reaction mixture was replaced with nitrogen three times to remove the oxygen inside the system and then heated at 80° C. for 16 hours. The reaction mixture was cooled to room temperature, diluted with water (50 mL) and extracted with dichloromethane (50 mL×3). The combined organic phases were washed successively with water (20 mL×3) and brine (20 mL), dried over sodium sulfate, filtered, and the filtrate was concentrated under reduced pressure. The residue was purified by silica gel column chromatography (dichloromethane:methanol=100:1) to deliver a white solid 29-b (137 mg, yield: 12%). LC-MS (ESI): m/z=289 [M+H]$^+$.

Preparation of Compound 29-a.

Compound 29-b (137 mg, 0.48 mmol), compound 15-b (151 mg, 0.48 mmol), potassium carbonate (197 mg, 1.43 mmol), tris(dibenzylideneacetone)dipalladium (82 mg, 0.14 mmol) and 2-dicyclohexylphosphino-2',6'-di-iso-propoxy-1,1'-biphenyl (67 mg, 0.14 mmol) were dissolved in N,N-dimethylformamide (3 mL), and the reaction mixture was replaced with nitrogen three times to remove the oxygen inside the system and then heated at 110° C. for 3 hours. The reaction mixture was cooled to room temperature, diluted with ice water (50 mL) and extracted with ethyl acetate (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=3:1) to deliver a pale yellow solid 29-a (80 mg, yield: 30%). LC-MS (ESI): m/z=571 [M+H]$^+$.

Preparation of Compound 29.

Compound 29-a (80 mg, 0.14 mmol) was dissolved in dichloromethane (3 mL). The reaction solution was cooled to 0° C., trifluoroacetic acid (3 mL) was added, and the reaction was stirred at room temperature for 3 hours. The reaction was concentrated under reduced pressure and the residue was dissolved in ethyl acetate (50 mL) and diluted with 1 M aqueous hydrochloric acid (50 mL). The separated aqueous phase was adjusted to pH 10 with saturated aqueous potassium carbonate solution. The solid was precipitated and filtered. The filter cake was washed with water (20 mL×3) and the solid was dried in vacuo to deliver a yellow solid 29 (37 mg, yield: 67%). LC-MS (ESI): m/z=471 [M+H]$^+$.

$^1$H-NMR (400 MHz, CD$_3$OD) δ: 9.17 (s, 1H), 7.95 (d, J=8 Hz, 1H), 7.87 (dd, J=1 Hz, J=8 Hz, 1H), 7.76 (dd, J=Hz, J=8 Hz, 1H), 7.43 (d, J=1 Hz, J=8 Hz, 1H), 7.10-1.79 (m, 3H), 6.48 (d, J=8 Hz, 1H), 4.63 (m, 2H), 3.63 (s, 3H), 3.26 (m, 4H), 2.87 (m, 2H), 2.73 (m, 1H), 1.73-1.85 (m, 4H) ppm.

Example 30

8-[2-Methoxy-4-(trifluoromethyl)phenyl])-N-[4-(piperidin-4-yl)-2,3-dihydro-1-benzofuran-7-yl]quinazolin-2-amine (Compound 30)

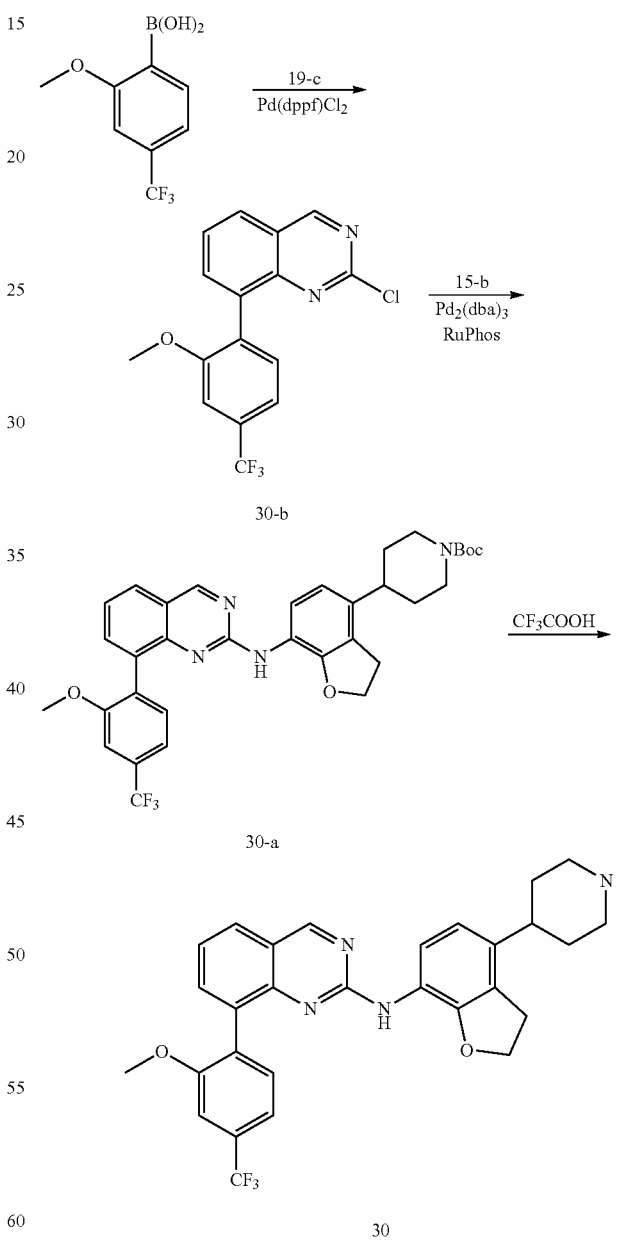

Preparation of Compound 30-b.

Compound 19-c (1.0 g, 4.13 mmol), 2-methoxy-4-trifluoromethylbenzeneboronic acid (1.1 g, 4.96 mmol), [1,1'-bis(diphenylphosphino)ferrocene]dichloropalladium(II) (335 mg, 0.41 mmol) and sodium carbonate (1.31 g, 12.4 mmol)

were dissolved in 1,4-dioxane (10 mL) and water (10 mL). The reaction mixture was replaced with nitrogen three times to remove the oxygen inside the system and then heated at 80° C. for 16 hours. The reaction mixture was cooled to room temperature, diluted with water (50 mL) and extracted with dichloromethane (50 mL×3). The combined organic phases were washed successively with water (20 mL×3) and brine (20 mL), dried over sodium sulfate, filtered, and the filtrate was concentrated under reduced pressure. The residue was purified by silica gel column chromatography (dichloromethane:methanol=100:1) to deliver a white solid 30-b (280 mg, yield: 21%). LC-MS (ESI): m/z=339 [M+H]+.

Preparation of Compound 30-a.

Compound 30-b (110 mg, 0.33 mmol), compound 15-b (87 mg, 0.33 mmol), potassium carbonate (135 mg, 0.98 mmol), tris(dibenzylideneacetone)dipalladium (56 mg, 0.1 mmol) and 2-dicyclohexylphosphino-2',6'-di-iso-propoxy-1,1'-biphenyl(46 mg, 0.1 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature, diluted with water (50 mL) and extracted with ethyl acetate (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=1:1) to deliver a pale yellow solid 30-a (80 mg, yield: 30%). LC-MS (ESI): m/z=621 [M+H]+.

Preparation of Compound 30.

Compound 30-a (85 mg, 0.15 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a yellow solid 30 (47 mg, yield: 67%). LC-MS (ESI): m/z=521 [M+H]+.

1H-NMR (400 MHz, CDCl3) δ: 9.08 (s, 1H), 7.88 (d, J=8 Hz, 2H), 7.75 (dd, J=1 Hz, J=8 Hz, 1H), 7.49 (d, J=8 Hz, 1H), 7.36-7.41 (m, 3H), 7.26 (d, J=8 Hz, 1H), 6.42 (d, J=8 Hz, 1H), 4.60 (t, J=8 Hz, 2H), 3.71 (s, 3H), 3.19-3.23 (m, 4H), 2.69-2.76 (m, 2H), 2.53 (m, 1H), 2.13 (m, 1H), 1.58-1.76 (m, 4H) ppm.

Example 31

4-[7-({8-[2-Methoxy-4-(trifluoromethyl)phenyl]quinazolin-2-yl}amino)-2,3-dihydro-1-benzofuran-4-yl]-piperidin-3-ol (Compound 31)

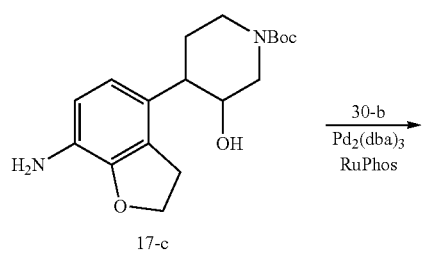

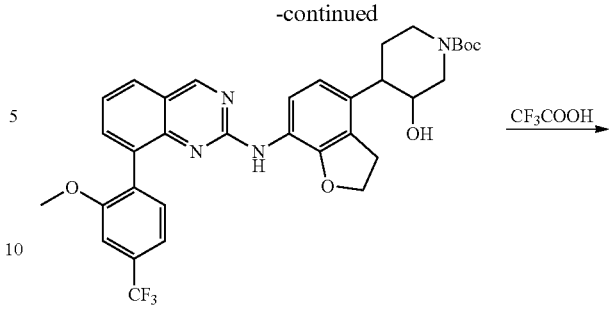

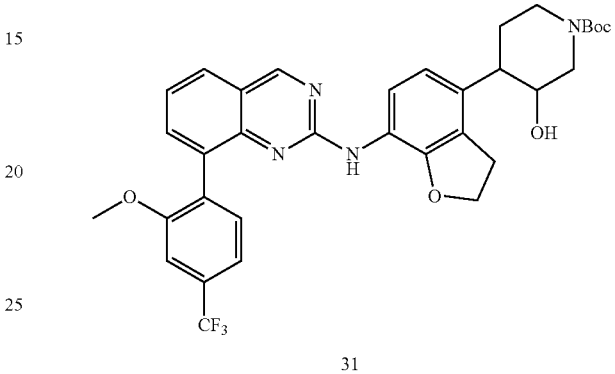

Preparation of Compound 31-a.

Compound 17-c (148 mg, 0.45 mmol), compound 30-b (150 mg, 0.45 mmol), potassium carbonate (183 mg, 1.33 mmol), tris(dibenzylideneacetone)dipalladium(76 mg, 0.13 mmol) and 2-dicyclohexylphosphino-2',6'-di-iso-propoxy-1,1'-biphenyl(62 mg, 0.13 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature, diluted with water (50 mL) and extracted with ethyl acetate (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=1:1) to deliver a pale yellow solid 31-a (87 mg, yield: 31%). LC-MS (ESI): m/z=637 [M+H]+.

Preparation of Compound 31.

Compound 31-a (87 mg, 0.15 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a pale yellow solid 31 (31 mg, yield: 43%). LC-MS (ESI): m/z=537 [M+H]+.

1H-NMR (400 MHz, CDCl3) δ: 9.08 (s, 1H), 7.93 (d, J=8 Hz, 1H), 7.76 (m, 1H), 7.49 (d, J=8 Hz, 1H), 7.28-7.42 (m, 3H), 7.26 (d, J=8 Hz, 1H), 6.47 (d, J=8 Hz, 1H), 4.61 (t, J=8 Hz, 2H), 3.71 (s, 3H), 3.71 (m, 1H), 3.24-3.39 (m, 4H), 2.53-2.67 (m, 1H), 1.75 (m, 2H) ppm.

Example 32

8-{2-Methoxy-4-[(morpholin-4-yl)carbonyl]phenyl}-N-[4-(piperidin-4-yl)-2,3-dihydro-1-benzofuran-7-yl]quinazolin-2-amine (Compound 32)

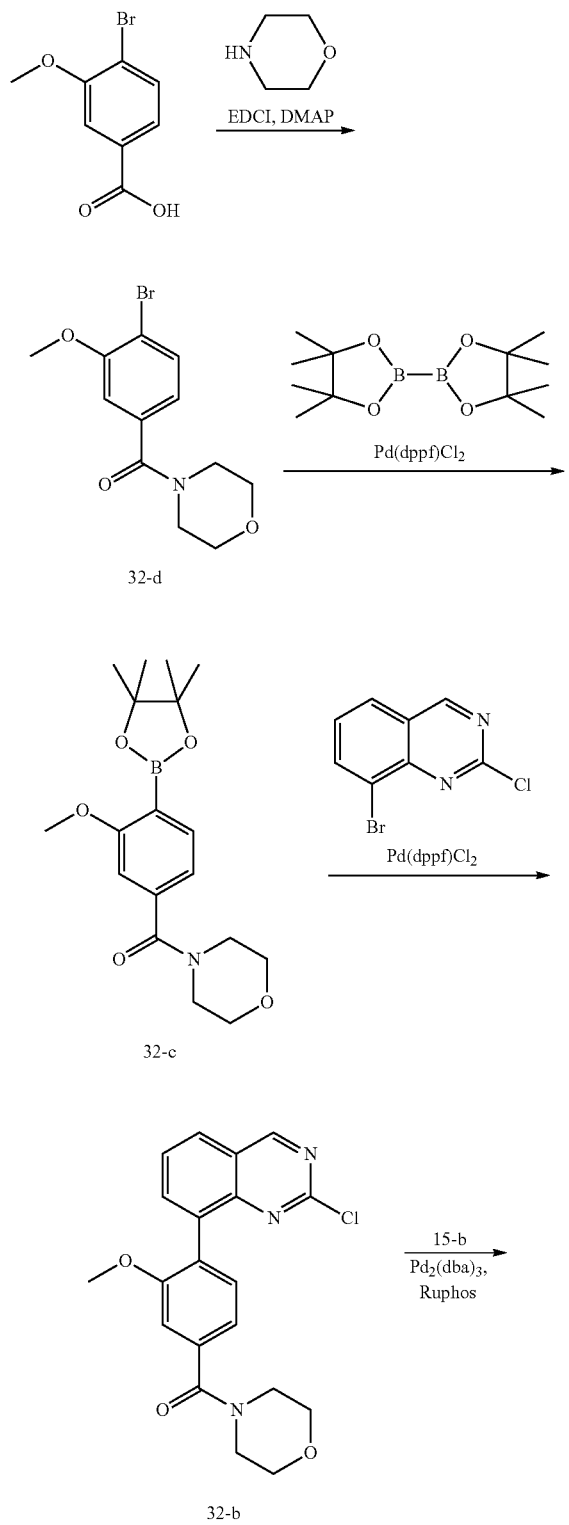

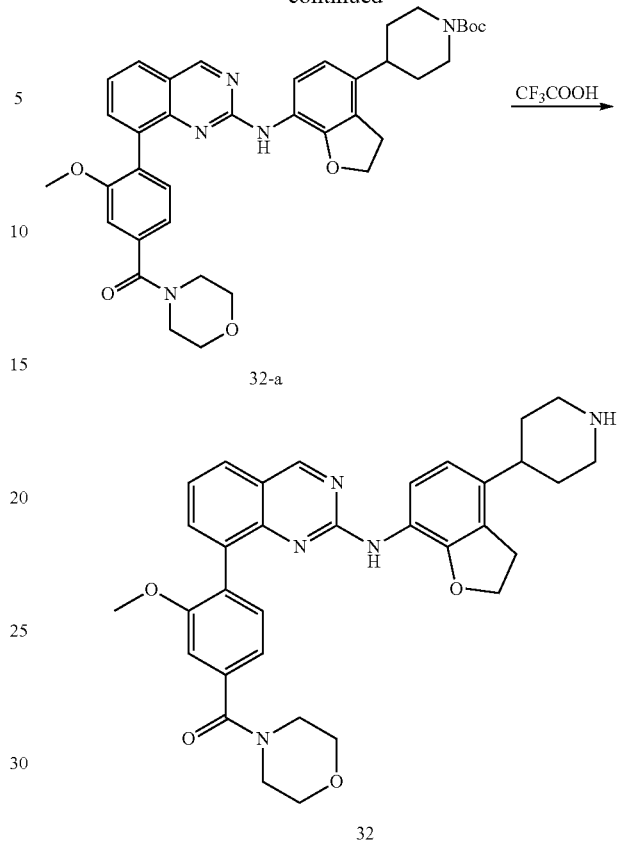

Preparation of Compound 32-d.

4-Bromo-3-methoxybenzoic acid (1.16 g, 5 mmol), morpholine (650 mg, 7.5 mmol), 1-(3-dimethylaminopropyl)-3-ethylcarbodiimide hydrochloride (1.5 g, 6 mmol), 4-dimethylaminopyridine (60 mg, 0.5 mmol) and triethylamine (2 mL, 15 mmol) were dissolved in dichloromethane (20 mL). After the reaction mixture was stirred at 20° C. for 16 hours, the reaction mixture was diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=2:1) to deliver a white solid 32-d (1.15 g, yield: 76%). LC-MS (ESI): m/z=300 [M+H]$^+$.

Preparation of Compound 32-c.

Compound 32-d (1.15 g, 3.85 mmol), bis(pinacolato)diboron (1.5 g, 5.77 mmol), anhydrous potassium acetate (1.14 g, 11.5 mmol) and [1,1'-bis(diphenylphosphino)ferrocene]dichloropalladium(II) (135 mg, 0.19 mmol) were dissolved in 1,4-dioxane (20 mL). The reaction mixture was replaced with nitrogen three times to remove the oxygen inside the system and then stirred at 80° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=5:1) to deliver a white solid 32-c (800 mg, yield: 60%). LC-MS (ESI): m/z=348 [M+H]$^+$.

Preparation of Compound 32-b.

Compound 32-c (800 mg, 2.3 mmol), 2-chloro-8-bromoquinazoline (600 mg, 2.46 mmol), anhydrous sodium carbonate (700 mg, 6.6 mmol) and [1,1'-bis(diphenylphosphino)ferrocene]dichloropalladium(II) (70 mg, 0.1 mmol) were dissolved in 1,4-dioxane (30 mL) and water (10 mL). The reaction mixture was replaced with nitrogen three times to remove the oxygen inside the system and then stirred at 80° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=5:1) to deliver a white solid 32-b (340 mg, yield: 38%). LC-MS (ESI): m/z=587 [M+H]$^+$.

Preparation of Compound 32-a.

Compound 32-b (340 mg, 0.89 mmol), compound 15-b (260 mg, 0.81 mmol), tris(dibenzylideneacetone)dipalladium (80 mg, 0.1 mmol), potassium carbonate (380 mg, 3.0 mmol) and 2-dicyclohexylphosphino-2',6'-di-iso-propoxy-1,1'-biphenyl(50 mg, 0.1 mmol) were dissolved in N,N-dimethylformamide (10 mL), and the reaction mixture was replaced with nitrogen three times to remove the oxygen inside the system and then heated at 130° C. for 16 hours. The reaction solution was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=4:1) to deliver a yellow solid 32-a (300 mg, yield: 50%). LC-MS (ESI): m/z=666 [M+H]$^+$.

Preparation of Compound 32.

Compound 32-a (300 mg, 0.45 mmol) was dissolved in dichloromethane (5 mL). The reaction solution was cooled to 0° C., trifluoroacetic acid (2 mL, 25.9 mmol) was added and the reaction mixture was stirred at room temperature for 30 minutes. The reaction mixture was concentrated under reduced pressure and the residue was diluted with water (10 mL). The pH of the mixed solution was adjusted to 10 with potassium carbonate solution. The aqueous phase was extracted with dichloromethane (50 mL×3). The combined organic phases were washed with water (20 mL) and brine (20 mL), dried over anhydrous sodium sulfate, filtered, and the filtrate was concentrated under reduced pressure. The residue was purified by silica gel column chromatography (petroleum ether:ethyl acetate=1:1) to deliver a yellow solid 32 (5 mg, yield: 2%). LC-MS (ESI): m/z=566 [M+H]$^+$.

$^1$H-NMR (400 MHz, CDCl$_3$) δ: 9.07 (s, 1H), 7.97 (d, J=8.8 Hz, 1H), 7.73 (t, J=6 Hz, 1H), 7.36-7.40 (m, 3H), 7.15 (s, 1H), 7.08 (d, J=8.0 Hz, 1H), 6.62 (d, J=8.0 Hz, 1H), 4.59 (t, J=8.0 Hz, 2H), 3.62-3.98 (m, 13H), 3.22 (t, J=8.0 Hz, 2H), 3.02 (t, J=8.0 Hz, 2H), 2.62-2.72 (m, 1H), 2.11-2.24 (m, 2H), 1.86-1.96 (m, 2H) ppm.

Example 33

3-Methoxy-4-(2-{[4-(piperidin-4-yl)-2,3-dihydro-1-benzofuran-7-yl]amino}quinazolin-8-yl)benzamide (Compound 33)

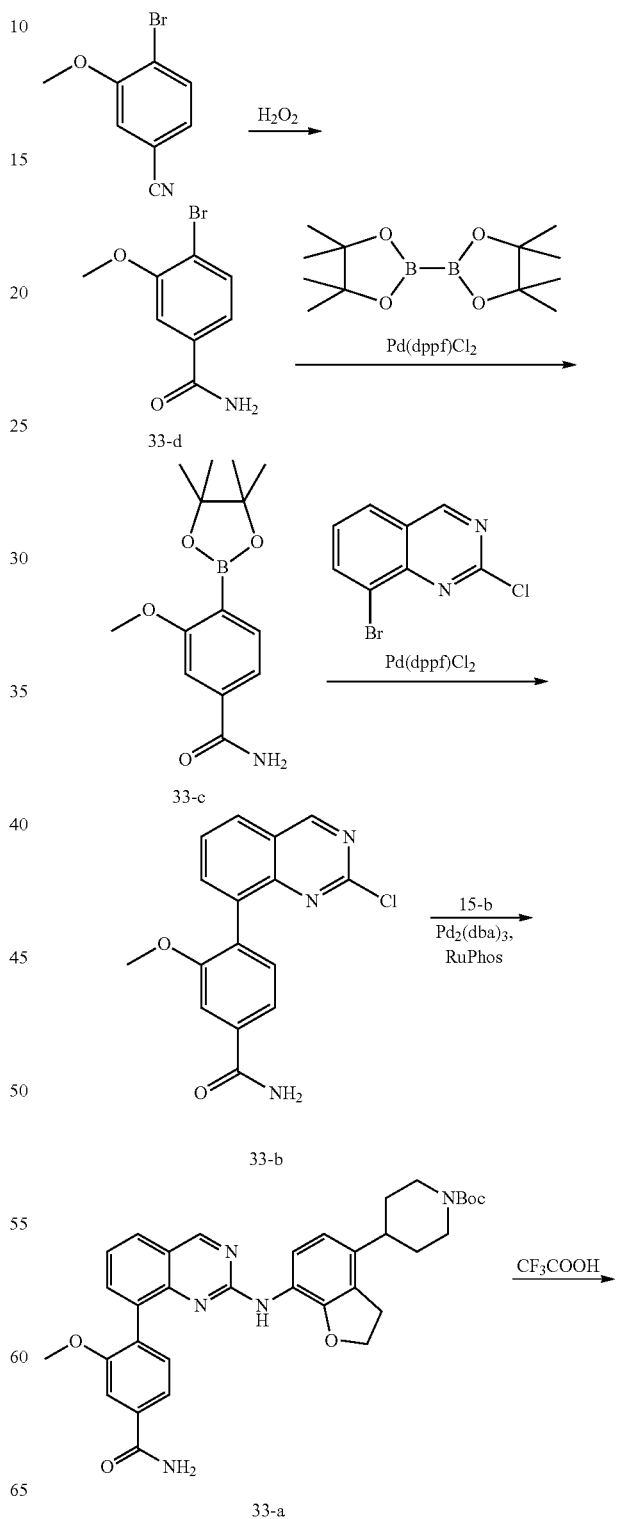

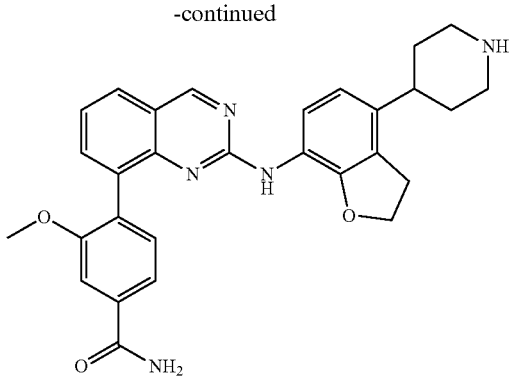

33

Preparation of Compound 33-d.

4-Bromo-3-fluorobenzonitrile (1.06 g, 5 mmol) and potassium carbonate (10.35 g, 7.5 mmol) were dissolved in dimethylsulfoxide (5 mL) at 0° C., and 30% hydrogen peroxide (2.5 g, 6.5 mmol) was added and then the mixture was stirred at 0° C. for 1 hour. The reaction mixture was diluted with ice water (10 mL) and extracted with dichloromethane (50 mL×3). The combined organic phases were washed successively with water (20 mL×3) and brine (20 mL), dried over anhydrous sodium sulfate and filtered, and the filtrate was concentrated under reduced pressure to deliver a yellow solid 33-d (1.05 g, yield: 91%). This product was used without further purification. LC-MS (ESI): m/z=230 (M+H)$^+$.

Preparation of Compound 33-c.

Compound 33-d (1.05 g, 4.56 mmol), bis(pinacolato) diboron (1.95 g, 7.65 mmol), anhydrous potassium acetate (1.5 g, 15.3 mmol) and [1,1'-bis(diphenylphosphino)ferrocene]dichloropalladium(II) (100 mg, 0.142 mmol) were dissolved in 1,4-dioxane (20 mL). The reaction mixture was replaced with nitrogen three times to remove the oxygen inside the system and then stirred at 80° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=5:1) to deliver a white solid 33-c (800 mg, yield: 63%). LC-MS (ESI): m/z=278 (M+H)$^+$.

Preparation of Compound 33-b.

Compound 33-c (800 mg, 2.81 mmol), 2-chloro-8-bromoquinazoline (562 mg, 2.31 mmol), anhydrous sodium carbonate (920 mg, 8.67 mmol) and [1,1'-bis(diphenylphosphino)ferrocene]dichloropalladium(II) (100 mg, 0.142 mmol) were dissolved in 1,4-dioxane (15 mL) and water (5 mL). The reaction mixture was replaced with nitrogen three times to remove the oxygen inside the system and then stirred at 80° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=4:1) to deliver a white solid 33-b (160 mg, yield: 18%). LC-MS (ESI): m/z=314 [M+H]$^+$.

Preparation of Compound 33-a.

Compound 33-b (340 mg, 0.89 mmol), compound 15-b (143 mg, 0.45 mmol), tris(dibenzylideneacetone)dipalladium (46 mg, 0.05 mmol), potassium carbonate (208 mg, 1.5 mmol) and 2-dicyclohexylphosphino-2',6'-di-iso-propoxy-1,1'-biphenyl(30 mg, 0.064 mmol) were dissolved in N,N-dimethylformamide (10 mL), and the reaction mixture was replaced with nitrogen three times to remove the oxygen inside the system and then heated at 130° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=4:1) to deliver a yellow solid 33-a (70 mg, yield: 23%). LC-MS (ESI): m/z=596 [M+H]$^+$.

Preparation of Compound 33.

Compound 33-a (70 mg, 0.12 mmol) was dissolved in dichloromethane (5 mL). The reaction solution was cooled to 0° C., trifluoroacetic acid (2 mL, 25.9 mmol) was added and the reaction mixture was stirred at room temperature for 30 minutes. The reaction mixture was concentrated under reduced pressure and the residue was diluted with water (10 mL). The pH of the mixed solution was adjusted to 10 with 1 M aqueous potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=1:1) to deliver a yellow solid 33 (6 mg, yield: 10%) was obtained. LC-MS (ESI): m/z=496 [M+H]$^+$.

$^1$H-NMR (400 MHz, CD$_3$OD) δ: 9.05 (s, 1H), 7.77 (d, J=8.0 Hz, 1H), 7.68 (d, J=8.0 Hz, 1H), 7.65 (d, J=6.8 Hz, 1H), 7.55 (s, 1H), 7.53 (d, J=8.0 Hz, 1H), 7.32 (t, J=8.0 Hz, 1H), 7.28 (d, J=8.0 Hz, 1H), 6.31 (d, J=8.0 Hz, 1H), 4.48 (t, J=8.8 Hz, 2H), 3.55 (s, 3H), 3.36-3.44 (m, 2H), 2.98-3.15 (m, 4H), 2.64-2.74 (m, 1H), 1.74-1.94 (m, 4H) ppm.

Example 34

8-(4-Methylsulfonyl-2-methoxyphenyl)-N-[4-(piperidin-4-yl)-2,3-dihydro-1-benzofuran-7-yl]oxazolin-2-amine (Compound 34)

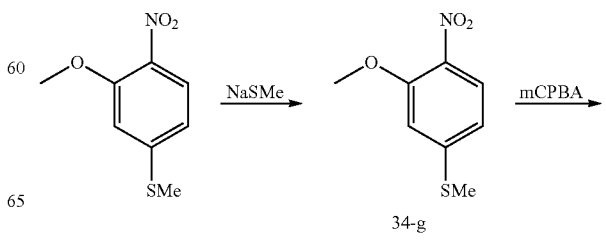

34-g

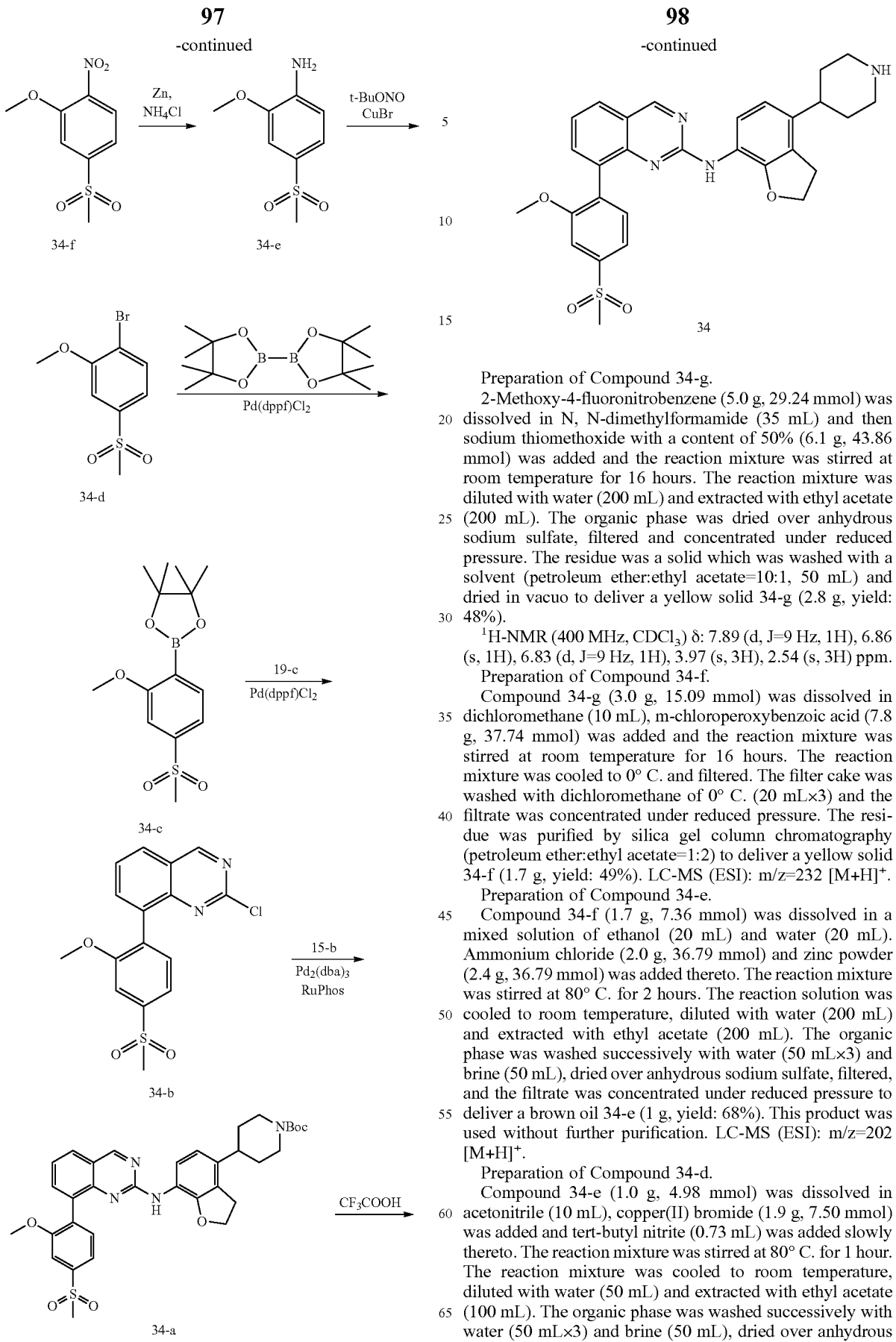

Preparation of Compound 34-g.

2-Methoxy-4-fluoronitrobenzene (5.0 g, 29.24 mmol) was dissolved in N, N-dimethylformamide (35 mL) and then sodium thiomethoxide with a content of 50% (6.1 g, 43.86 mmol) was added and the reaction mixture was stirred at room temperature for 16 hours. The reaction mixture was diluted with water (200 mL) and extracted with ethyl acetate (200 mL). The organic phase was dried over anhydrous sodium sulfate, filtered and concentrated under reduced pressure. The residue was a solid which was washed with a solvent (petroleum ether:ethyl acetate=10:1, 50 mL) and dried in vacuo to deliver a yellow solid 34-g (2.8 g, yield: 48%).

$^1$H-NMR (400 MHz, CDCl$_3$) δ: 7.89 (d, J=9 Hz, 1H), 6.86 (s, 1H), 6.83 (d, J=9 Hz, 1H), 3.97 (s, 3H), 2.54 (s, 3H) ppm.

Preparation of Compound 34-f.

Compound 34-g (3.0 g, 15.09 mmol) was dissolved in dichloromethane (10 mL), m-chloroperoxybenzoic acid (7.8 g, 37.74 mmol) was added and the reaction mixture was stirred at room temperature for 16 hours. The reaction mixture was cooled to 0° C. and filtered. The filter cake was washed with dichloromethane of 0° C. (20 mL×3) and the filtrate was concentrated under reduced pressure. The residue was purified by silica gel column chromatography (petroleum ether:ethyl acetate=1:2) to deliver a yellow solid 34-f (1.7 g, yield: 49%). LC-MS (ESI): m/z=232 [M+H]$^+$.

Preparation of Compound 34-e.

Compound 34-f (1.7 g, 7.36 mmol) was dissolved in a mixed solution of ethanol (20 mL) and water (20 mL). Ammonium chloride (2.0 g, 36.79 mmol) and zinc powder (2.4 g, 36.79 mmol) was added thereto. The reaction mixture was stirred at 80° C. for 2 hours. The reaction solution was cooled to room temperature, diluted with water (200 mL) and extracted with ethyl acetate (200 mL). The organic phase was washed successively with water (50 mL×3) and brine (50 mL), dried over anhydrous sodium sulfate, filtered, and the filtrate was concentrated under reduced pressure to deliver a brown oil 34-e (1 g, yield: 68%). This product was used without further purification. LC-MS (ESI): m/z=202 [M+H]$^+$.

Preparation of Compound 34-d.

Compound 34-e (1.0 g, 4.98 mmol) was dissolved in acetonitrile (10 mL), copper(II) bromide (1.9 g, 7.50 mmol) was added and tert-butyl nitrite (0.73 mL) was added slowly thereto. The reaction mixture was stirred at 80° C. for 1 hour. The reaction mixture was cooled to room temperature, diluted with water (50 mL) and extracted with ethyl acetate (100 mL). The organic phase was washed successively with water (50 mL×3) and brine (50 mL), dried over anhydrous sodium sulfate, filtered, and the filtrate was concentrated under reduced pressure. The residue was purified by silica gel column chromatography (petroleum ether:ethyl acetate=1:1) to deliver a pale yellow solid 34-d (540 mg, yield: 41%). LC-MS (ESI): m/z=202 [M+H]⁺.

Preparation of Compound 34-c.

Compound 34-d (300 mg, 1.14 mmol), bis(pinacolato)diboron (433 mg, 1.71 mmol) and anhydrous potassium acetate (281 mg, 3.42 mmol) were suspended in dioxane (5 mL), and then [1,1'-bis(diphenylphosphino)ferrocene]dichloropalladium(II) (98 mg, 0.15 mmol) was added. The reaction mixture was replaced with nitrogen three times to remove the oxygen inside the system and then heated at 85° C. for 16 hours. The reaction mixture was cooled to room temperature and diluted with ethyl acetate (20 mL). The mixture was filtered through diatomite and the filtrate was concentrated under reduced pressure to deliver a black oil 34-c (350 mg). This product was used without further purification.

Preparation of Compound 34-b.

Compound 19-c (387 mg, 1.61 mmol), 2-methoxy-4-methanesulfonyl benzeneboronic acid pinacol ester (500 mg, 1.61 mmol), [1,1'-bis(diphenylphosphino)ferrocene]dichloropalladium(II)(374 mg, 0.5 mmol) and sodium carbonate (512 mg, 4.83 mmol) were dissolved in 1,4-dioxane (5 mL) and water (5 mL). The reaction mixture was replaced with nitrogen three times to remove the oxygen inside the system and then heated at 80° C. for 16 hours. The reaction mixture was cooled to room temperature, diluted with water (50 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (dichloromethane:methanol=100:1) to deliver a pale yellow solid 34-b (148 mg, yield: 27%). LC-MS (ESI): m/z=349 [M+H]⁺.

Preparation of Compound 34-a.

Compound 34-b (148 mg, 0.43 mmol), compound 15-b (113 mg, 0.43 mmol), potassium carbonate (176 mg, 1.28 mmol), tris(dibenzylideneacetone)dipalladium(73 mg, 0.13 mmol) and 2-dicyclohexylphosphino-2',6'-di-iso-propoxy-1,1'-biphenyl(60 mg, 0.13 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature, diluted with water (50 mL) and extracted with ethyl acetate (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=1:1) to deliver a pale yellow solid 34-a (40 mg, yield: 17%). LC-MS (ESI): m/z=579 [M+H]⁺.

Preparation of Compound 34.

Compound 34-a (40 mg, 0.07 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a pale yellow solid 34 (18 mg, yield: 55%). LC-MS (ESI): m/z=479 [M+H]⁺.

¹H-NMR (400 MHz, CDCl₃) δ: 9.09 (s, 1H), 7.88 (d, J=8 Hz, 2H), 7.74-7.78 (m, 2H), 7.67-7.69 (m, 1H), 7.59-7.61 (m, 2H), 7.36-7.41 (m, 2H), 6.47 (d, J=8 Hz, 1H), 4.61 (t, J=8 Hz, 2H), 3.76 (s, 3H), 3.17-3.25 (m, 7H), 2.69-2.741 (m, 2H), 2.51-2.57 (m, 1H), 2.73 (m, 1H), 1.55-1.65 (m, 4H) ppm Example 35

8-(4-Methylsulfonyl-2-methoxyphenyl)-N-[2-methyl-4-(piperidin-4-yl)-2,3-dihydro-1-benzofuran-7-yl]quinazolin-2-amine (Compound 35)

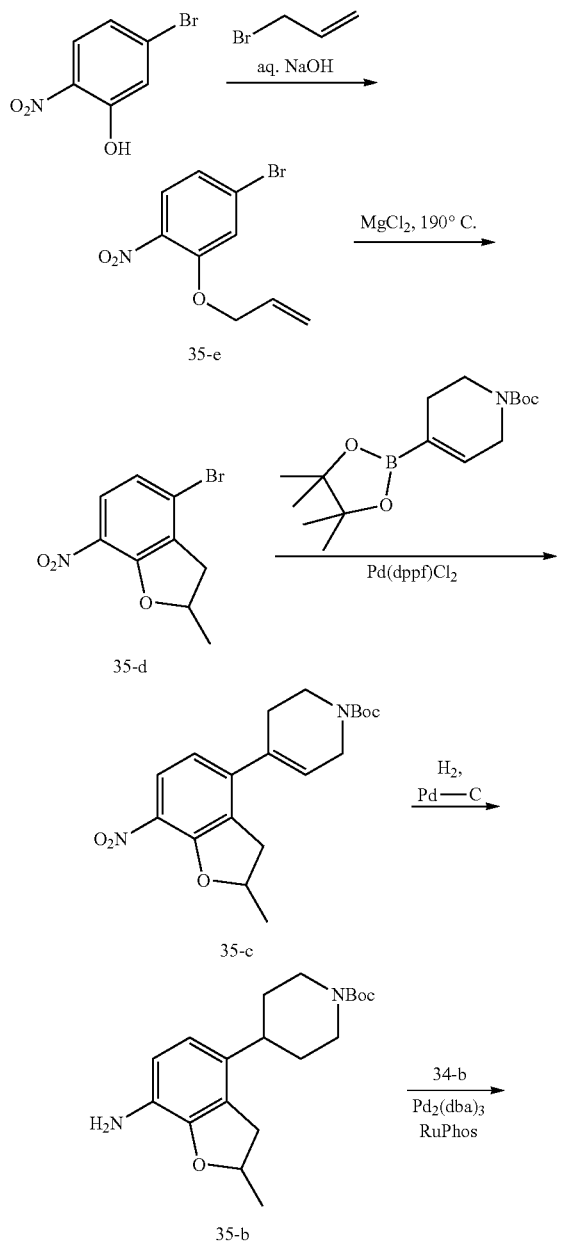

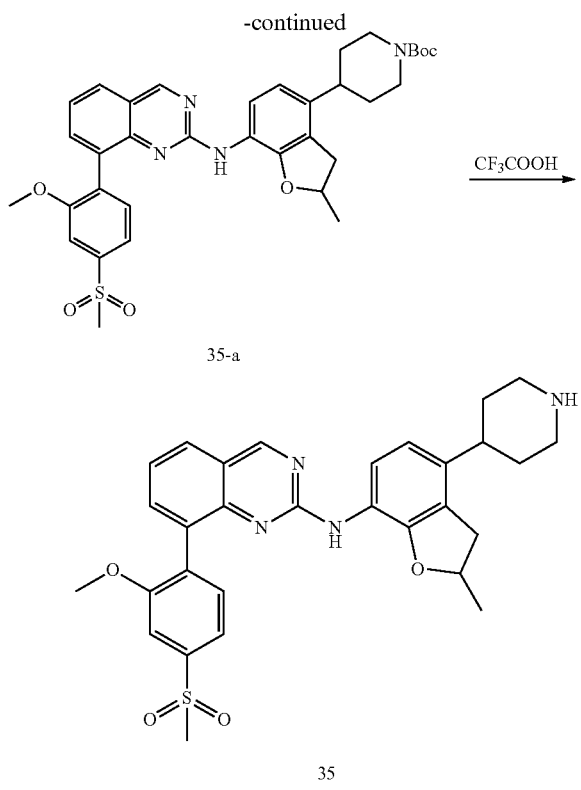

Preparation of Compound 35-e.

3-Bromopropene (2.5 g, 20.74 mmol) was added to a solution of 2-nitro-5-bromophenol (3.0 g, 13.82 mmol) and sodium hydroxide (830 mg, 20.74 mmol) in water (50 mL). The reaction mixture was stirred at 50° C. for 16 hours. The reaction mixture was cooled to room temperature and the organic phase was dried over anhydrous sodium sulfate. The filtrate was concentrated under reduced pressure and the residue was purified by silica gel column chromatography (petroleum ether:ethyl acetate=10:1) to deliver a yellow solid 35-e (1.1 g, yield: 37%).

Preparation of Compound 35-d.

Compound 35-e (1.1 g, 4.29 mmol) and anhydrous magnesium chloride (100 mg) were mixed and the mixture was heated to 200° C. for 2 hours and then cooled to room temperature. 0.1 M aqueous hydrochloric acid solution (50 mL) was added to the mixture and then extracted with ethyl acetate (50 mL×3). The combined organic phases were dried over anhydrous sodium sulfate, filtered, and the filtrate was concentrated under reduced pressure. The residue was purified by silica gel column chromatography (petroleum ether: ethyl acetate=10:1) to deliver a yellow solid 35-d (250 mg, yield: 23%).

$^1$H-NMR (400 MHz, CDCl$_3$) δ: 7.81 (d, J=8 Hz, 1H), 7.06 (d, J=8 Hz, 1H), 5.27 (m, 1H), 3.42 (dd, J=8 Hz, 16 Hz, 1H), 2.90 (dd, J=8 Hz, 16 Hz, 1H), 1.59 (d, J=6 Hz, 3H) ppm.

Preparation of Compound 35-c.

Compound 35-d (250 mg, 0.97 mmol), N-Boc-1,2,3,6-tetrahydropyridine-4-boronic acid pinacol ester (360 mg, 1.17 mmol), sodium carbonate (308 mg, 2.91 mmol) and [1,1'-bis(diphenylphosphino)ferrocene]dichloropalladium (II) (236 mg, 0.29 mmol) were dissolved in dioxane (5 mL) and water (5 mL). The reaction mixture was replaced with nitrogen three times to remove the oxygen inside the system and then heated at 80° C. for 12 hours. The reaction mixture was cooled to room temperature and concentrated under reduced pressure. The residue was diluted with water (100 mL) and extracted with dichloromethane (100 mL×3). The combined organic phases were dried over anhydrous sodium sulfate, filtered, and the residue was purified by silica gel column chromatography (petroleum ether:ethyl acetate=5:1) to deliver a pale yellow solid 35-c (190 mg, yield: 54%). LC-MS (ESI): m/z=305 [M+H-t-Bu]$^+$.

Preparation of Compound 35-b.

Compound 35-c (190 mg, 0.53 mmol) and 10% palladium-carbon (150 mg) were dissolved in ethanol (10 mL). The reaction mixture was replaced with hydrogen three times and then hydrogenated at room temperature for 16 hours. The reaction mixture was filtered to remove palladium-carbon and the filtrate was concentrated under reduced pressure to deliver a purple oil 35-b (143 mg, yield: 82%). The product was used without further purification. LC-MS (ESI): m/z=333 [M+H]$^+$.

Preparation of Compound 35-a.

Compound 34-b (150 mg, 0.43 mmol), compound 35-b (143 mg, 0.43 mmol), potassium carbonate (178 mg, 1.29 mmol), tris(dibenzylideneacetone)dipalladium (74 mg, 0.13 mmol) and 2-dicyclohexylphosphino-2',6'-di-iso-propoxy-1,1'-biphenyl (60 mg, 0.13 mmol) were dissolved in N,N-dimethylformamide (3 mL), the reaction mixture was replaced with nitrogen three times to remove the oxygen inside the system and then heated at 110° C. for 16 hours. The reaction mixture was cooled to room temperature, diluted with water (50 mL) and extracted with ethyl acetate (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=1:1) to deliver a pale yellow solid 35-a (183 mg, yield: 66%). LC-MS (ESI): m/z=645 [M+H]$^+$.

Preparation of Compound 35.

Compound 35-a (183 mg, 0.28 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a pale yellow solid 35 (121 mg, yield: 79%). LC-MS (ESI): m/z=545 [M+H]$^+$.

$^1$H-NMR (400 MHz, CDCl$_3$) δ: 9.09 (s, 1H), 7.88 (d, J=8 Hz, 2H), 7.74-7.78 (m, 2H), 7.67-7.69 (m, 1H), 7.60-7.62 (m, 2H), 7.37-7.41 (m, 2H), 6.45 (d, J=8 Hz, 1H), 4.97 (m, 1H), 3.34 (m, 1H), 3.32 (s, 3H), 3.21 (m, 2H), 2.83 (m, 1H), 2.71 (m, 2H), 2.53 (m, 1H), 1.55-1.65 (m, 4H), 1.25 (d, J=8 Hz, 3H) ppm.

Example 36

7-{[8-(4-Methylsulfonyl-2-methoxyphenyl)quinazolin-2-yl]amino}-2,3-dihydro-1-benzofuran-4-carboxamide (Compound 36)

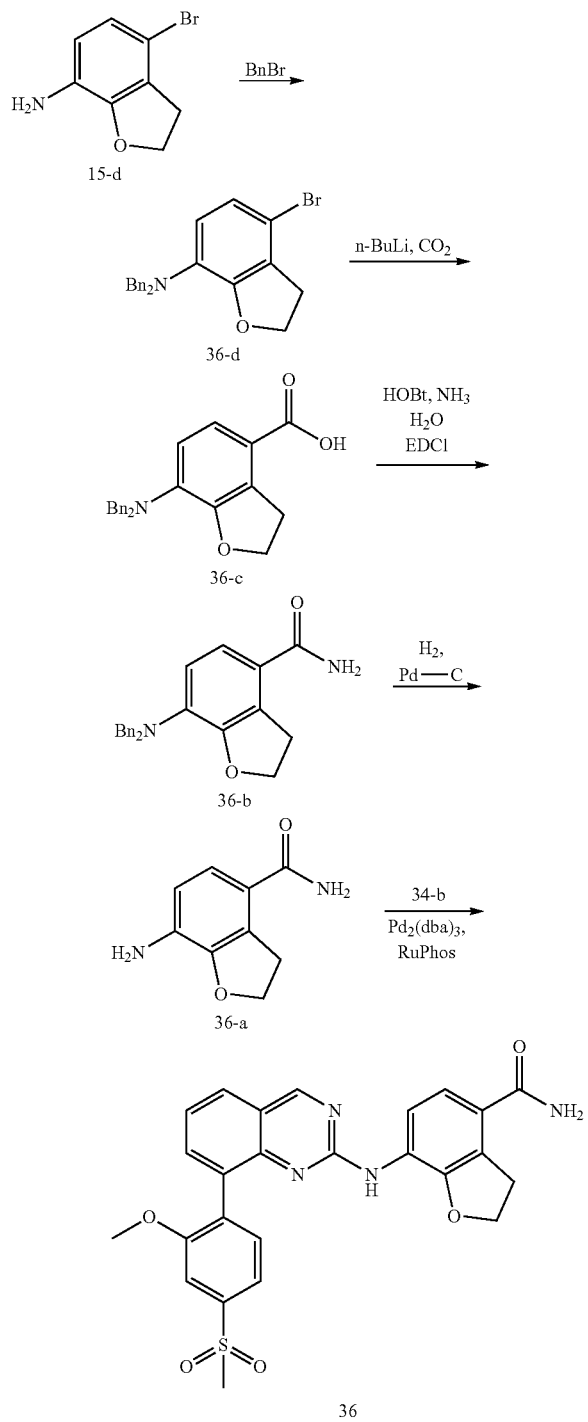

Preparation of Compound 36-d.

Compound 15-d (1.07 g, 5 mmol), benzyl bromide (2.66 g, 15 mmol) and potassium carbonate (2.8 g, 15 mmol) were dissolved in acetonitrile (30 mL). The reaction mixture was replaced with nitrogen three times to remove the oxygen inside the system and then heated at 80° C. for 16 hours. The reaction mixture was cooled to room temperature, diluted with ice water (50 mL) and extracted with dichloromethane (50 mL×3). The combined organic phases were washed successively with water (50 mL×3) and brine (50 mL), dried over anhydrous sodium sulfate, filtered, and the filtrate was concentrated under reduced pressure. The residue was purified by silica gel column chromatography (petroleum ether: ethyl acetate=10:1) to deliver a yellow solid 36-d (1.8 g, yield: 91%). LC-MS (ESI): m/z=394 [M+H]$^+$.

Preparation of Compound 36-c.

Compound 36-d (2.4 g, 6.1 mmol) was dissolved in anhydrous tetrahydrofuran (50 mL) and the reaction solution was cooled to −78° C. Then n-butyllithium (5 mL, 12.5 mmol, 2.5 M solution in n-hexane), was added dropwise to the above solution, and the stirring was continued for 3 hours after the dropwise addition. The reaction mixture was poured into dry ice (5 g) and then diluted with ice water (50 mL), then the pH was adjusted to 3 with 1.0 M hydrochloric acid. The mixed solution was extracted with dichloromethane (50 mL×3). The combined organic phases were washed successively with water (50 mL×3) and brine (50 mL), dried over anhydrous sodium sulfate, filtered, the filtrate was concentrated under reduced pressure. The residue was purified by silica gel column chromatography (petroleum ether: ethyl acetate=2:1) to deliver a white solid 36-c (1.5 g, yield: 63%). LC-MS (ESI): m/z=360 [M+H]$^+$.

Preparation of Compound 36-b.

Ammonium Hydroxide (1 mL) was added dropwise to a solution of 1-hydroxybenzotriazole (740 mg, 5.48 mmol) in tetrahydrofuran (5 mL). The reaction mixture was stirred for 30 minutes and then filtered. The filter cake was dried in vacuo to deliver a solid (960 mg). The solid, compound 36-c (1.5 g, 4.2 mmol), 1-(3-dimethylaminopropyl)-3-ethylcarbodiimide hydrochloride (1.2 g, 6.3 mmol) and triethylamine (1.5 mL, 12.6 mmol) were dissolved in dichloromethane (30 mL) and the reaction mixture was stirred at room temperature for 16 hours. The reaction mixture was diluted with ice water (50 mL) and extracted with dichloromethane (50 mL×3). The combined organic phases were washed successively with water (50 mL×3) and brine (50 mL), dried over sodium, filtered, and the filtrate was concentrated under reduced pressure. The residue was purified by silica gel thin layer chromatography preparative plate (petroleum ether: ethyl acetate=3:1) to deliver a white solid 36-b (1.1 g, yield: 73%). LC-MS (ESI): m/z=359 [M+H]$^+$.

Preparation of Compound 36-a.

Compound 36-b (1.1 g, 3.07 mmol) and 10% palladium-carbon (100 mg) were dissolved in methanol (20 mL). The reaction mixture was replaced with hydrogen three times and then hydrogenated at room temperature for 16 hours. The reaction mixture was filtered to remove the palladium-carbon, and the filtrate was concentrated under reduced pressure. The residue was purified by silica gel thin layer chromatography preparative plate (petroleum ether:ethyl acetate=2:1) to deliver a white solid 36-a (500 mg, yield: 91%). LC-MS (ESI): m/z=179 [M+H]$^+$.

Preparation of Compound 36.

Compound 36-a (86 mg, 0.48 mmol), compound 34-b (166 mg, 0.48 mmol), tris(dibenzylideneacetone)dipalladium (22 mg, 0.024 mmol), potassium carbonate (207 mg, 1.5 mmol) and 2-dicyclohexylphosphino-2',6'-di-isopropoxy-1,1'-biphenyl(10 mg, 0.024 mmol) were dissolved in N,N-dimethylformamide (10 mL). The reaction mixture was replaced with nitrogen three times to remove the oxygen inside the system and then heated at 130° C. for 16 hours.

The reaction solution was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=1:1) to deliver a white solid 36 (25 mg, yield: 10%). LC-MS (ESI): m/z=491 [M+H]⁺.

$^1$H-NMR (400 MHz, CDCl$_3$) δ: 9.13 (s, 1H), 7.80-7.83 (m, 3H), 7.69-7.71 (m, 1H), 7.44-7.60 (m, 5H), 6.97 (d, J=8.8 Hz, 1H), 4.64 (t, J=8.8 Hz, 2H), 3.71 (s, 3H), 3.62 (t, J=8.8 Hz, 2H), 3.25 (s, 3H) ppm Example 37

4-[7-({8-[2-Methoxy-4-trifluoromethylphenyl]quinazolin-2-yl}amino)-2,3-dihydro-1-benzofuran-4-yl]piperidin-4-ol (Compound 37)

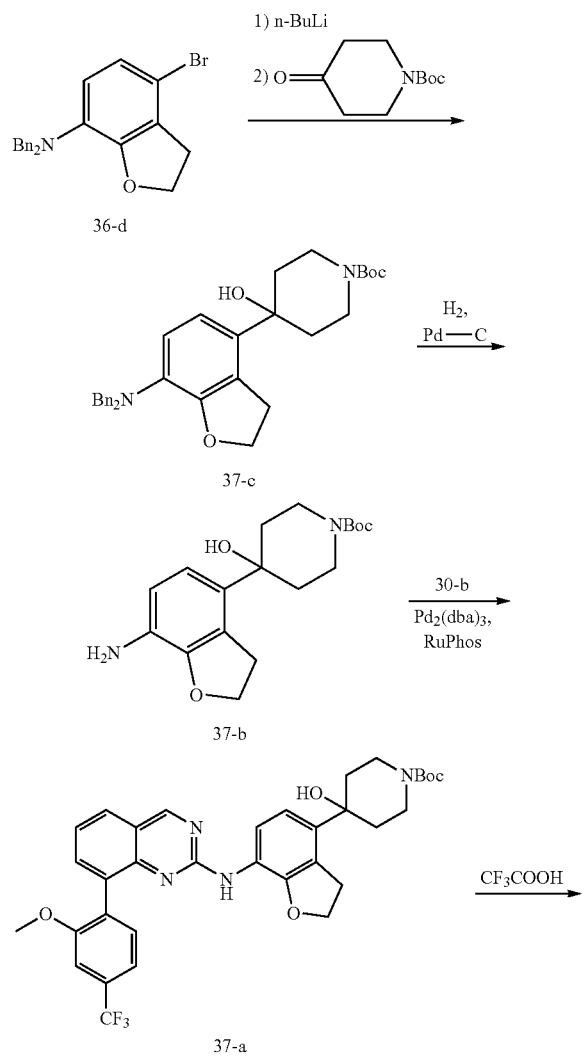

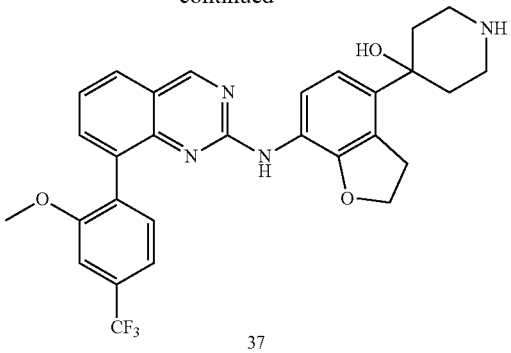

37

Preparation of Compound 37-c.

Compound 36-d (3.6 g, 9.1 mmol) was dissolved in anhydrous tetrahydrofuran (30 mL) and the reaction solution was cooled to −78° C. Then n-butyllithium (7.5 mL, 18.75 mmol, 2.5 M solution in n-hexane), was added dropwise to the above solution, and stirring was continued for 3 hours after the addition. A solution of N-Boc-piperidone (3.62 g, 18.7 mmol) in anhydrous tetrahydrofuran (20 mL) was added dropwise to the above reaction solution. The reaction mixture was stirred at room temperature for 16 hours and then diluted with saturated aqueous ammonium chloride solution (50 mL). The mixed solution was extracted with dichloromethane (50 mL×3). The combined organic phases were washed successively with water (50 mL×3) and brine (50 mL), dried over anhydrous sodium sulfate, filtered, the filtrate was concentrated under reduced pressure. The residue was purified by silica gel column chromatography (petroleum ether:ethyl acetate=4:1) to deliver a white solid 37-c (2.5 g, yield: 53%). LC-MS (ESI): m/z=515 [M+H]⁺.

Preparation of Compound 37-b.

Compound 37-c (2.5 g, 4.86 mmol) and 10% palladium-carbon (200 mg) were dissolved in methanol (30 mL). The reaction mixture was replaced with hydrogen three times and then hydrogenated at room temperature for 16 hours. The reaction mixture was filtered to remove palladium-carbon and the filtrate was concentrated under reduced pressure. The residue was purified by silica gel thin layer chromatography preparative plate (petroleum ether:ethyl acetate=2:1) to deliver a white solid 37-b (700 mg, yield: 43%). LC-MS (ESI): m/z=357 [M+Na]⁺.

Preparation of Compound 37-a.

Compound 37-b (300 mg, 0.94 mmol), compound 30-b (300 mg, 0.86 mmol), tris(dibenzylideneacetone)dipalladium (30 mg, 0.033 mmol), potassium carbonate (300 mg, 2.17 mmol) and 2-dicyclohexylphosphino-2',6'-di-isopropoxy-1,1'-biphenyl(90 mg, 0.19 mmol) were dissolved in N,N-dimethylformamide (10 mL). The reaction mixture was replaced with nitrogen three times to remove the oxygen inside the system and then heated at 130° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=5:1) to deliver a white solid 37-a (250 mg, yield: 40%). LC-MS (ESI): m/z=637 [M+H]⁺.

Preparation of Compound 37.

Compound 37-a (250 mg, 0.39 mmol) was dissolved in dichloromethane (5 mL). The reaction solution was cooled to 0° C., trifluoroacetic acid (2 mL, 25.9 mmol) was added and the reaction mixture was stirred at room temperature for 30 minutes. The reaction mixture was concentrated under reduced pressure and the residue was diluted with water (10 mL). The pH of the mixed solution was adjusted to 10 with 1 M aqueous potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=1:1) to deliver a yellow solid 37 (42 mg, yield: 10%). LC-MS (ESI): m/z=537 [M+H]$^+$.

$^1$H-NMR (400 MHz, CDCl$_3$) δ: 9.10 (s, 1H), 7.90 (d, J=8.4 Hz, 1H), 7.76-7.79 (m, 2H), 7.38-7.50 (m, 4H), 7.29 (s, 1H), 6.56 (d, J=8.0 Hz, 1H), 4.58 (t, J=8.8 Hz, 2H), 3.72 (s, 3H), 3.48 (t, J=8.8 Hz, 2H), 3.12-3.18 (m, 2H), 2.98-3.06 (m, 2H), 1.99-2.09 (m, 2H), 1.78-1.85 (m, 2H) ppm Example 38

8-[2-Methoxy-4-trifluoromethylphenyl]-N-[(2R)-2-methyl-4-(piperidin-4-yl)-2,3-dihydro-1-benzofuran-7-yl]quinazolin-2-amine (Compound 38)

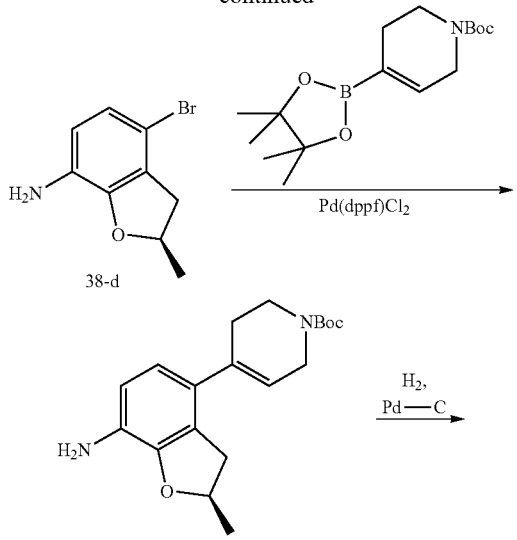

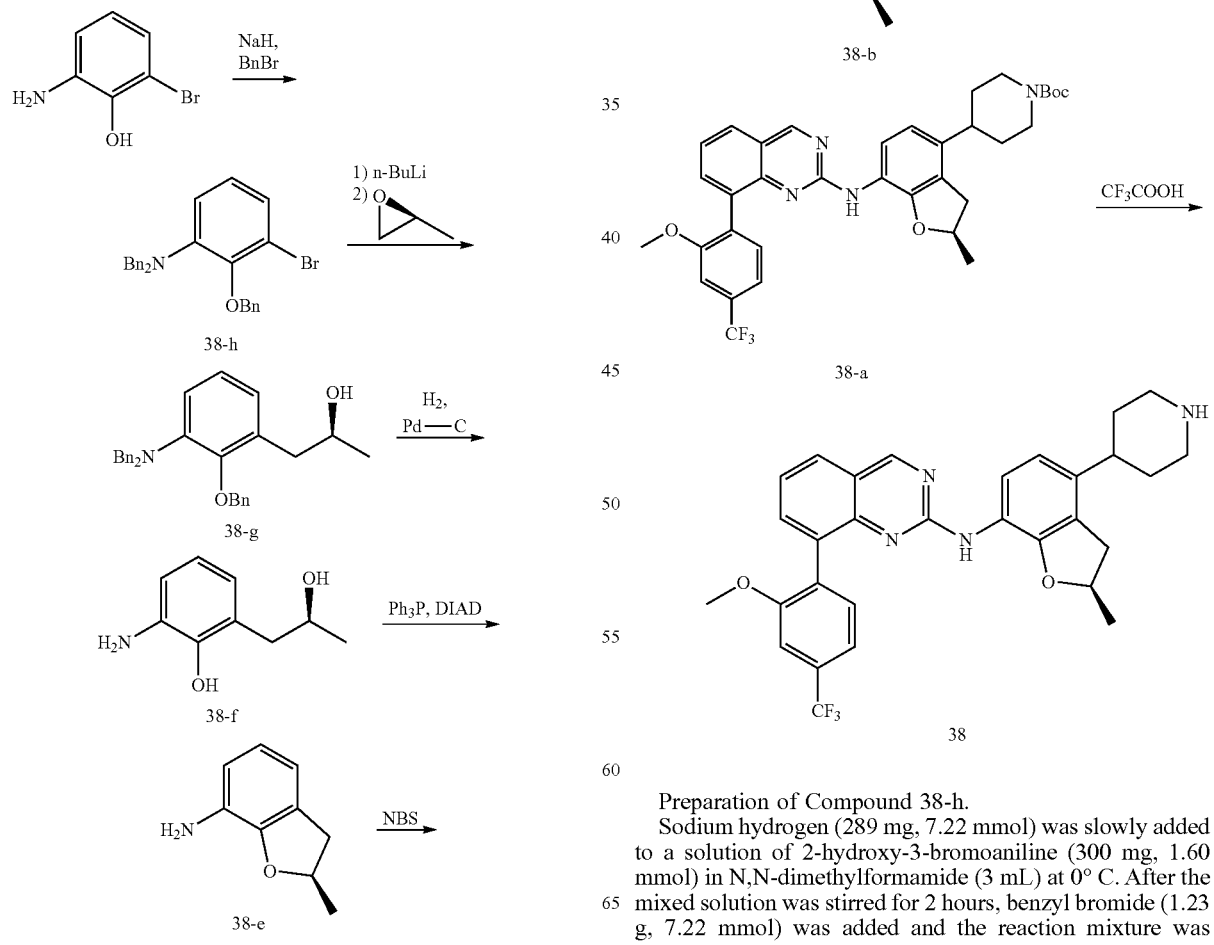

Preparation of Compound 38-h.

Sodium hydrogen (289 mg, 7.22 mmol) was slowly added to a solution of 2-hydroxy-3-bromoaniline (300 mg, 1.60 mmol) in N,N-dimethylformamide (3 mL) at 0° C. After the mixed solution was stirred for 2 hours, benzyl bromide (1.23 g, 7.22 mmol) was added and the reaction mixture was stirred at room temperature for 18 hours. The reaction mixture was poured into water (50 mL) and extracted with ethyl acetate (50 mL×3). The combined organic phases were washed successively with water (20 mL×3) and brine (20 mL), dried over sodium, filtered, and the filtrate was concentrated under reduced pressure. The residue was purified by silica gel column chromatography (petroleum ether:ethyl acetate=100:1) to deliver a pale brown solid 38-h (690 mg, yield: 94%). LC-MS (ESI): m/z=458 [M+H]$^+$.

Preparation of Compound 38-g.

Compound 38-h (3 g, 6.56 mmol) was dissolved in anhydrous tetrahydrofuran (30 mL) and the reaction solution was cooled to −78° C. Then n-butyllithium (7.5 mL, 18.75 mmol, 2.5 M solution in n-hexane), was added dropwise to the above solution, and the stirring was continued for 30 minutes after the addition. A solution of S-propylene oxide (580 mg, 9.84 mmol) in anhydrous tetrahydrofuran (2 mL) was added dropwise to the above reaction solution. After the addition, boron trifluoride diethyl etherate (1.4 g, 9.84 mmol) was added. The resulting yellow solution was slowly warmed to room temperature and stirring was continued for 16 hours and then diluted with saturated aqueous ammonium chloride solution (50 mL). The mixed solution was extracted with ethyl acetate (50 mL×3). The combined organic phases were washed successively with water (50 mL×3) and brine (50 mL), dried over anhydrous sodium sulfate, filtered, the filtrate was concentrated under reduced pressure. The residue was purified by silica gel column chromatography (petroleum ether:ethyl acetate=5:1) to deliver a pale yellow oil 38-g (2.1 g, yield: 66%). LC-MS (ESI): m/z=438 [M+H]$^+$.

Preparation of Compound 38-f.

Compound 38-g (1.6 g, 3.66 mmol) and 10% palladium-carbon (200 mg) were dissolved in ethanol (50 mL). The reaction mixture was replaced with hydrogen three times and then hydrogenated at room temperature for 16 hours. The reaction mixture was filtered to remove palladium-carbon, and the filtrate was concentrated under reduced pressure to deliver a brown oil 38-f (460 mg, yield: 61%). This product was used without further purification. LC-MS (ESI): m/z=168 [M+H]$^+$.

Preparation of Compound 38-e.

Compound 38-f (460 mg, 2.75 mmol) and triphenylphosphine (1.08 g, 4.12 mmol) were dissolved in anhydrous tetrahydrofuran (10 mL). The reaction mixture was cooled to 0° C. and diisopropyl azodicarboxylate (838 mg, 4.15 mmol) was slowly added dropwise. After the addition, the reaction mixture was slowly warmed to room temperature and the stirring was continued for 16 hours. The reaction mixture was concentrated under reduced pressure and the residue was purified by silica gel column chromatography (petroleum ether:ethyl acetate=5:1) to deliver a pale brown solid 38-e (190 mg, yield: 46%). LC-MS (ESI): m/z=150 [M+H]$^+$.

Preparation of Compound 38-d.

Compound 38-e (190 mg, 1.28 mmol) was dissolved in N,N-dimethylformamide (2 mL). The reaction solution was cooled to 0° C., and N-bromosuccinimide (237 mg, 1.34 mmol) was added in batches and the reaction mixture was stirred at room temperature for 3 hours. The reaction mixture was poured into water (40 mL) and extracted with ethyl acetate (50 mL×3). The combined organic phases were washed successively with water (50 mL×3) and brine (50 mL), dried over sodium, filtered and the filtrate was concentrated under reduced pressure to deliver a pale brown solid 38-d (261 mg, yield: 90%). This product was used without further purification.

Preparation of Compound 38-c.

Compound 38-d (250 mg, 1.11 mmol), N-Boc-1,2,3,6-tetrahydropyridine-4-boronic acid pinacol ester (510 mg, 1.65 mmol), anhydrous sodium carbonate (350 mg, 3.31 mmol) and [1,1'-bis(diphenylphosphino)ferrocene]dichloropalladium(II) (50 mg, 0.06 mmol) were suspended in 1,4-dioxane (5 mL) and water (5 mL). The reaction mixture was replaced with nitrogen three times to remove the oxygen inside the system and then stirred at 80° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, the filtrate was concentrated under reduced pressure. The residue was purified by silica gel thin layer chromatography preparative plate (petroleum ether:ethyl acetate=3:1) to deliver a light brown solid 38-c (140 mg, yield: 39%). LC-MS (ESI): m/z=331 [M+H]$^+$.

Preparation of Compound 38-b.

Compound 38-c (140 mg, 0.42 mmol) and 10% palladium-carbon (150 mg) were dissolved in ethanol (10 mL). The reaction mixture was replaced with hydrogen three times and then hydrogenated at room temperature for 16 hours. The reaction mixture was filtered to remove palladium-carbon and the filtrate was concentrated under reduced pressure to deliver a brown solid 38-b (128 mg, yield: 91%). This product was used without further purification. LC-MS (ESI): m/z=277 [M+H-t-Bu]$^+$.

Preparation of Compound 38-a.

Compound 38-b (128 mg, 0.39 mmol), compound 30-b (130 mg, 0.39 mmol), tris(dibenzylideneacetone)dipalladium (66 mg, 0.12 mmol), potassium carbonate (159 mg, 1.16 mmol) and 2-dicyclohexylphosphino-2',6'-di-isopropoxy-1,1'-biphenyl(54 mg, 0.12 mmol) were dissolved in N,N-dimethylformamide (3 mL). The reaction mixture was replaced with nitrogen three times to remove the oxygen inside the system and then heated at 110° C. for 16 hours. The reaction mixture was cooled to room temperature, diluted with ice water (10 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=1:1) to deliver a yellow solid 38-a (82 mg, yield: 34%). LC-MS (ESI): m/z=635 [M+H]$^+$.

Preparation of Compound 38.

Compound 38-a (82 mg, 0.13 mmol) was dissolved in dichloromethane (3 mL). The reaction solution was cooled to 0° C., trifluoroacetic acid (3 mL, 38.85 mmol) was added and the reaction was stirred at room temperature for 3 hours. The reaction was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a yellow solid 38 (15 mg, yield: 22%). LC-MS (ESI): m/z=535 [M+H]$^+$.

$^1$H-NMR (400 MHz, CDCl$_3$) δ: 9.08 (s, 1H), 7.88 (d, J=8 Hz, 2H), 7.76 (dd, J=1 Hz, J=8 Hz, 1H), 7.49 (d, J=8 Hz, 1H), 7.36-7.41 (m, 3H), 7.26 (d, J=8 Hz, 1H), 6.40 (d, J=8 Hz, 1H), 4.60 (t, J=8 Hz, 2H), 3.73 (s, 3H), 3.35 (m, 1H), 3.21 (m, 2H), 2.76 (m, 1H), 2.73 (m, 2H), 2.53 (m, 1H), 1.71 (m, 1H), 1.46 (d, J=8 Hz, 3H), 1.25 (m, 2H) ppm.

Example 39

7-({8-[2-methoxy-4-trifluoromethylphenyl]quinazolin-2-yl}amino)-N-(piperidin-4-yl)-2,3-dihydro-1-benzofuran-4-carboxamide (Compound 39)

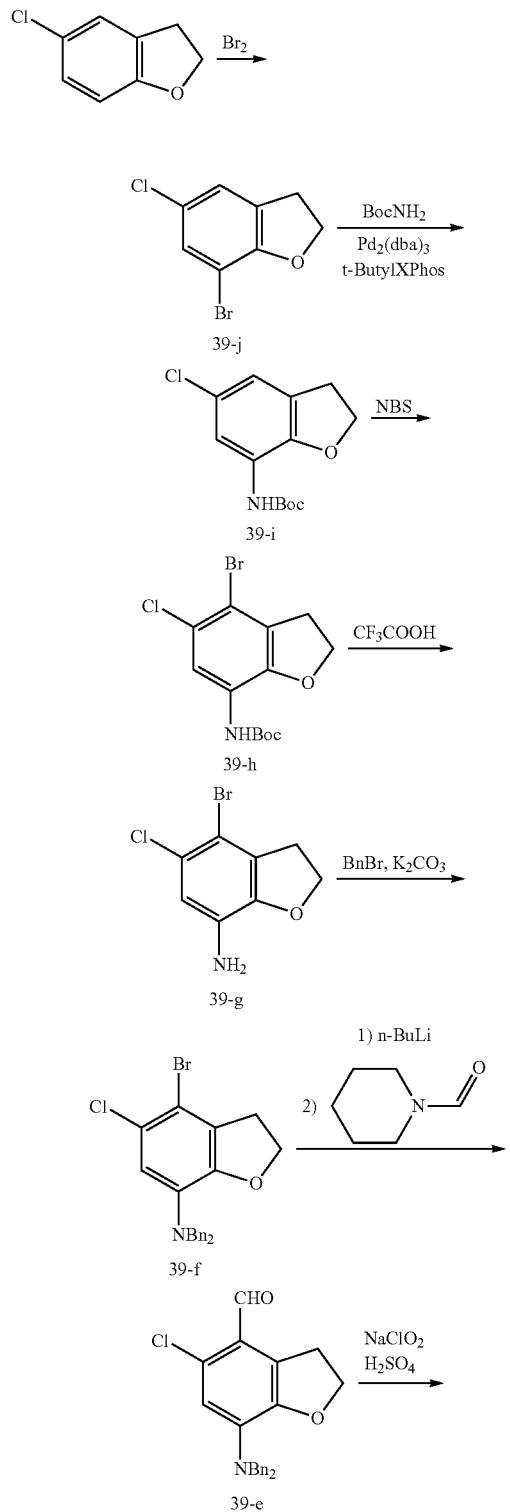

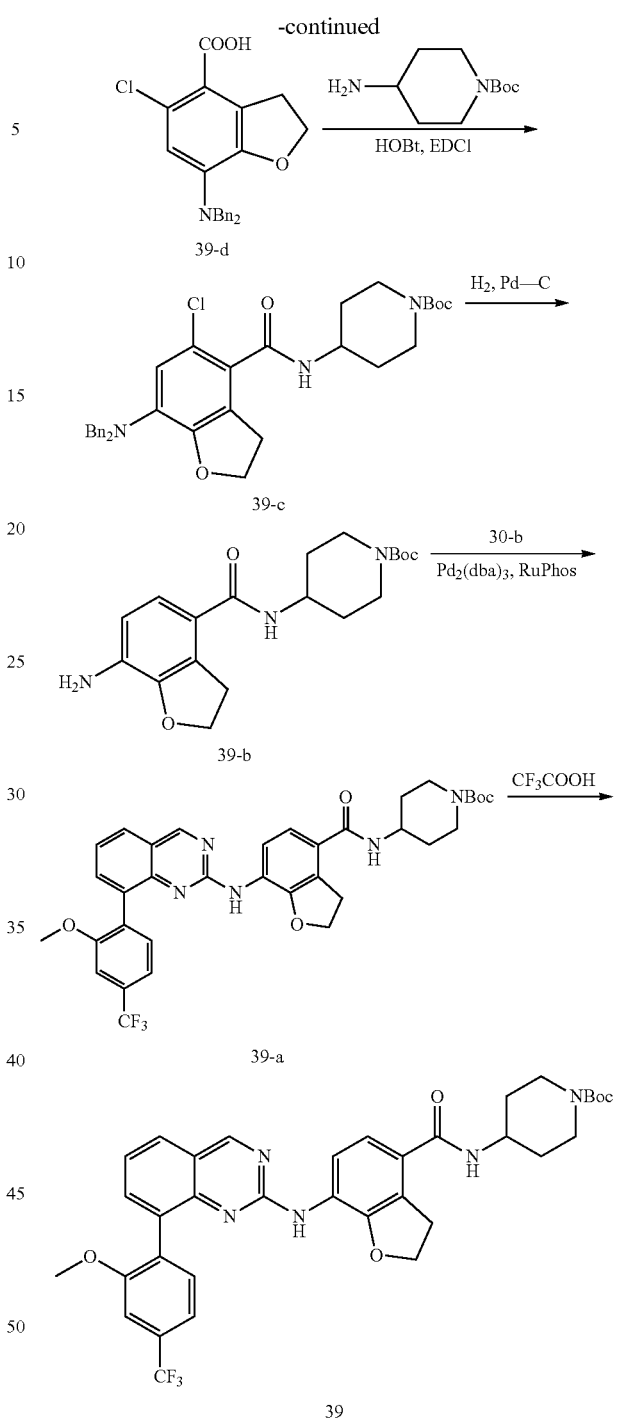

Preparation of Compound 39-j.

5-Chloro-2,3-dihydrobenzofuran (1.84 g, 10 mmol) was dissolved in acetic acid (15 mL) and the reaction solution was cooled to 0° C. A solution of liquid bromine (0.62 mL, 12 mmol) in acetic acid (5 mL) was added dropwise thereto. After the addition, the reaction mixture was stirred at room temperature for 16 hours. The pH of the reaction mixture was adjusted to 8 with saturated aqueous sodium carbonate solution and then extracted with petroleum ether (50 mL×3). The organic phase was dried over anhydrous sodium sulfate and filtered. The filtrate was concentrated under reduced pressure to deliver a yellow oil 39-j (2.5 g, yield: 90%), this product was used without further purification.

Preparation of Compound 39-i.

Compound 39-j (2.5 g, 10.5 mmol), BocNH$_2$ (1.5 g, 12.8 mmol), sodium tert-butoxide (3.2 g, 32.6 mmol), tris(dibenzylideneacetone)dipalladium (66 mg, 0.12 mmol) and 2-di-tert-butylphosphino-2',4',6'-triisopropylbiphenyl (30 mg, 0.06 mmol) were dissolved in toluene (30 mL). The reaction mixture was replaced with nitrogen three times to remove the oxygen inside the system and then heated at 80° C. for 16 hours. The reaction mixture was cooled to room temperature and filtered through diatomite. The filter cake was washed with ethyl acetate (50 mL×2). The combined filtrates were dried over anhydrous sodium sulfate, filtered, and the filtrate was concentrated under reduced pressure. The residue was purified by silica gel column chromatography (petroleum ether:ethyl acetate=10:1) to deliver a yellow solid 39-i (2 g, yield: 71%). LC-MS (ESI): m/z=214 [M+H-t-Bu]$^+$.

Preparation of Compound 39-h.

Compound 39-i (540 mg, 2 mmol) was dissolved in N,N-dimethylformamide (2 mL) and the reaction solution was cooled to 0° C. and N-bromosuccinimide (360 mg, 2 mmol) was added in batches and stirred at room temperature for 16 hours at room temperature. The reaction mixture was diluted with water (50 mL) and extracted with ethyl acetate (50 mL×3). The combined organic phases were dried over anhydrous sodium sulfate, filtered and concentrated under reduced pressure to deliver a yellow solid 39-h (650 mg, yield: 93%). This product was used without further purification. LC-MS (ESI): m/z=292 [M+H-t-Bu]$^+$.

Preparation of Compound 39-g.

Compound 39-h (2.8 g, 5.16 mmol) was dissolved in dichloromethane (30 mL). The reaction solution was cooled to 0° C., trifluoroacetic acid (10 mL) was added, and the reaction mixture was stirred at room temperature for 2 hours. The reaction mixture was concentrated under reduced pressure and the residue was diluted with saturated aqueous potassium carbonate solution (30 mL) and extracted with ethyl acetate (50 mL×3). The combined organic phases were dried over anhydrous sodium sulfate, filtered and the filtrate was concentrated under reduced pressure to deliver compound 39-g (1.8 g, yield: 91%). The product was used without further purification. LC-MS (ESI): m/z=248 [M+H]$^+$.

Preparation of Compound 39-f.

Compound 39-g (1.8 g, 7.28 mmol), benzyl bromide (4.4 g, 25.5 mmol) and potassium carbonate (3.52 g, 25.5 mmol) were dissolved in acetonitrile (50 mL). The reaction mixture was replaced with nitrogen three times to remove the oxygen inside the system and then heated at 80° C. for 16 hours. The reaction mixture was cooled to room temperature, diluted with water (50 mL) and extracted with ethyl acetate (50 mL×3). The combined organic phases were washed successively with water (50 mL×3) and brine (50 mL), dried over anhydrous sodium sulfate, filtered, and the filtrate was concentrated under reduced pressure. The residue was purified by silica gel column chromatography (petroleum ether:ethyl acetate=10:1) to deliver a pale yellow solid 39-f (2 g, yield: 64%). LC-MS (ESI): m/z=428 [M+H]$^+$.

Preparation of Compound 39-e.

Compound 39-f (2.0 g, 4.68 mmol) was dissolved in anhydrous tetrahydrofuran (50 mL) and the reaction solution was cooled to −78° C. Then n-butyllithium (2.8 mL, 7 mmol, 2.5 M solution in n-hexane), was added dropwise to the above solution, and the stirring was continued for 1 hour after the addition. A solution of formylpiperidine (795 mg, 7.03 mmol) in tetrahydrofuran (1 mL) was added dropwise to the above solution and stirring was continued for 1 hour. The reaction mixture was allowed to warm to room temperature and quenched with saturated aqueous ammonium chloride solution (50 mL), the mixed solution was extracted with ethyl acetate (50 mL×3). The combined organic phases were washed successively with water (50 mL) and brine (50 mL), dried over anhydrous sodium sulfate, filtered, and the filtrate was concentrated under reduced pressure. The residue was purified by silica gel column chromatography (petroleum ether:ethyl acetate=2:1) to deliver a pale yellow solid 39-e (680 mg, yield: 39%). LC-MS (ESI): m/z=378 [M+H]$^+$.

Preparation of Compound 39-d.

Compound 39-e (350 mg, 0.93 mmol), dimethylsulfoxide (88 mg, 1.12 mmol) and concentrated sulfuric acid (51 mg, 0.51 mmol) were dissolved in acetonitrile (3 mL) and water (1 mL). The reaction mixture was cooled to 0° C. and a solution of sodium chlorite (116 mg, 1.39 mmol) in water (2 mL) was added dropwise. The reaction mixture was stirred at this temperature for 30 minutes and then allowed to warm to room temperature. The reaction mixture was concentrated under reduced pressure and the residue was diluted with water (50 mL) and extracted with ethyl acetate (50 mL×3). The combined organic phases were dried over anhydrous sodium sulfate, filtered and the filtrate was concentrated under reduced pressure to deliver a pale yellow solid 39-d (170 mg, yield: 47%). This product was used without further purification. LC-MS (ESI): m/z=394 [M+H]$^+$.

Preparation of Compound 39-c.

Compound 39-d (400 mg, 1.02 mmol), N-Boc-4-aminopiperidine (244 mg, 1.22 mmol), 1-(3-dimethylaminopropyl)-3-ethylcarbodiimide hydrochloride (1.5 g, 6 mmol), 4-dimethylaminopyridine (60 mg, 0.5 mmol), triethylamine (2 mL, 15 mmol) and 1-hydroxybenzotriazole (137 mg, 1.02 mmol) were dissolved in dichloromethane (5 mL). After the reaction mixture was stirred at room temperature for 16 hours, the reaction solution was diluted with water (50 mL) and extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel thin layer chromatography plate (petroleum ether:ethyl acetate=1:1) to deliver a white solid 39-c (375 mg, yield: 65%). LC-MS (ESI): m/z=576 [M+H]$^+$.

Preparation of Compound 39-b.

Compound 39-c (375 mg, 0.65 mmol) and 10% palladium-carbon (100 mg) were dissolved in ethanol (10 mL). The reaction mixture was replaced with hydrogen three times and then hydrogenated at room temperature for 16 hours. The reaction mixture was filtered to remove palladium-carbon and the filtrate was concentrated under reduced pressure to deliver a pale brown solid 39-b (270 mg, yield: 100%). LC-MS (ESI): m/z=306 [M+H-t-Bu]$^+$.

Preparation of Compound 39-a.

Compound 39-b (150 mg, 0.42 mmol), compound 30-b (140 mg, 0.42 mmol), potassium carbonate (172 mg, 1.25 mmol), tris(dibenzylideneacetone)dipalladium (72 mg, 0.13 mmol) and 2-dicyclohexylphosphino-2',6'-di-iso-propoxy-1,1'-biphenyl(58 mg, 0.13 mmol) were dissolved in N,N-dimethylformamide (3 mL). The reaction mixture was replaced with nitrogen three times to remove the oxygen inside the system and then heated at 110° C. for 16 hours. The reaction mixture was cooled to room temperature, diluted with water (20 mL) and extracted with dichloromethane (50 mL×3). The combined organic phases were washed successively with water (20 mL×3) and brine (20 mL), dried over sodium sulfate, filtered, and the filtrate was concentrated under reduced pressure. The residue was purified by silica gel thin layer chromatography preparative plate (ethyl acetate as developing solvent) to deliver a yellow solid 39-a (20 mg, yield: 7%). LC-MS (ESI): m/z=664 [M+H]$^+$.

Preparation of Compound 39.

Compound 39-a (20 mg, 0.03 mmol) was dissolved in dichloromethane (2 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in ethyl acetate (50 mL) and diluted with saturated aqueous sodium bicarbonate solution (50 mL). The organic phase was dried over anhydrous sodium sulfate, filtered, and the filtrate was concentrated under reduced pressure. The residue was purified by high performance liquid chromatography (mobile phase: 0.05% TFA in water:acetonitrile=35%-45%) to deliver a pale yellow solid 39 (5 mg, yield: 30%). LC-MS (ESI): m/z=564 [M+H]$^+$.

$^1$H-NMR (400 MHz, CDCl$_3$) δ: 9.14 (s, 1H), 7.96 (d, J=8 Hz, 1H), 7.78-7.82 (m, 1H), 7.55 (s, 1H), 7.41-7.52 (m, 3H), 7.29 (m, 1H), 6.63 (d, J=9 Hz, 1H), 5.88 (d, J=8 Hz, 1H), 4.66 (t, J=8 Hz, 2H), 4.15 (m, 1H), 3.74 (m, 1H), 3.70 (s, 3H), 3.58 (m, 2H), 3.02 (m, 1H), 2.18 (m, 1H), 2.09 (m, 2H), 1.58-1.76 (m, 2H) ppm.

Example 40

7-{[8-(4-Fluoro-2-methoxyphenyl)quinazolin-2-yl] amino}-N-(piperidin-4-yl)-2,3-dihydro-1-benzofuran-4-carboxamide (Compound 40)

Preparation of Compound 40-a.

Compound 39-b (150 mg, 0.42 mmol), compound 27-b (120 mg, 0.42 mmol), potassium carbonate (172 mg, 1.25 mmol), tris(dibenzylideneacetone)dipalladium (72 mg, 0.13 mmol) and 2-dicyclohexylphosphino-2',6'-di-iso-propoxy-1,1'-biphenyl(58 mg, 0.13 mmol) were dissolved in N,N-dimethylformamide (3 mL). The reaction mixture was replaced with nitrogen three times to remove the oxygen inside the system and then heated at 110° C. for 16 hours. The reaction mixture was cooled to room temperature, diluted with water (20 mL) and extracted with dichloromethane (50 mL×3). The combined organic phases were washed successively with water (20 mL×3) and brine (20 mL), dried over sodium sulfate, filtered and the filtrate was concentrated under reduced pressure. The residue was purified by silica gel thin layer chromatography preparative plate (ethyl acetate as developing solvent) to deliver a yellow solid 40-a (21 mg, yield: 8%). LC-MS (ESI): m/z=614 [M+H]$^+$.

Preparation of Compound 40.

Compound 40-a (21 mg, 0.03 mmol) was dissolved in dichloromethane (2 mL). The reaction solution was cooled to 0° C., trifluoroacetic acid (2 mL) was added, and the reaction mixture was stirred at room temperature for 3 hours. The reaction mixture was concentrated under reduced pressure and the residue was dissolved in ethyl acetate (50 mL) and diluted with saturated aqueous sodium bicarbonate solution (50 mL). The organic phase was dried over anhydrous sodium sulfate, filtered, the filtrate was concentrated under reduced pressure, and the residue was purified by silica gel thin layer chromatography preparative plate (ethyl acetate as developing solvent) to deliver a pale yellow solid 40 (4 mg, yield: 23%). LC-MS (ESI): m/z=514 [M+H]$^+$.

$^1$H-NMR (400 MHz, CDCl$_3$) δ: 9.12 (s, 1H), 8.13 (d, J=8 Hz, 1H), 7.76 (dd, J=8 Hz, 2H), 7.57 (s, 1H), 7.42 (m, 1H),

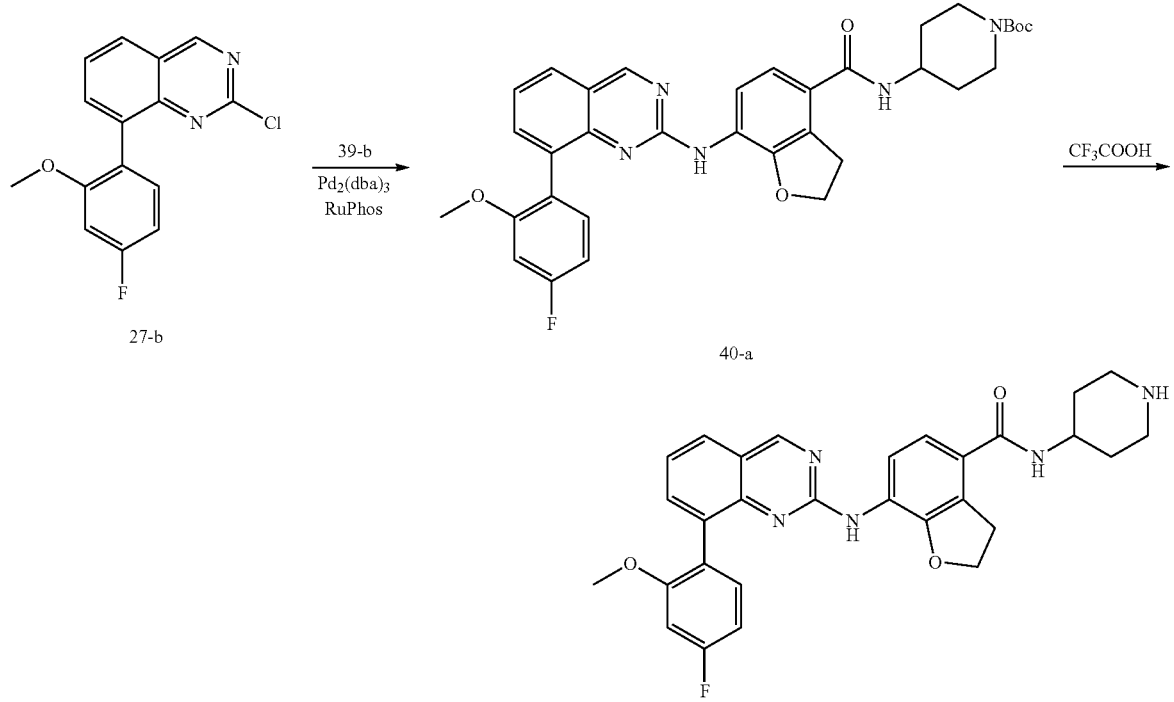

7.34 (m, 1H), 6.77-6.86 (m, 3H), 5.90 (m, 1H), 4.66 (t, J=8 Hz, 2H), 4.05 (s, 3H), 3.67 (s, 3H), 3.57 (t, J=8 Hz, 2H), 3.14 (m, 2H), 2.76 (m, 2H), 2.06 (m, 2H), 1.47 (m, 2H) ppm.

Example 41

4-(7-{[8-(4-Fluoro-2-methoxyphenyl)quinazolin-2-yl]amino}-2,3-dihydro-1-benzofuran-4-yl)piperidin-4-ol (Compound 41)

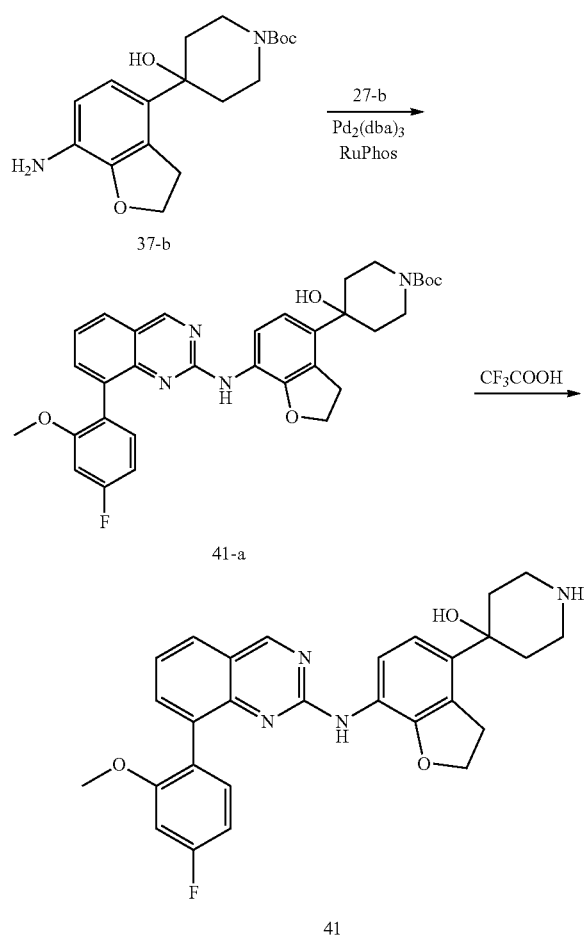

Preparation of Compound 41-a.

Compound 37-b (394 mg, 1.18 mmol), compound 27-b (400 mg, 1.18 mmol), tris(dibenzylideneacetone)dipalladium (204 mg, 0.36 mmol), potassium carbonate (492 mg, 3.56 mmol) and 2-dicyclohexylphosphino-2',6'-di-isopropoxy-1,1'-biphenyl (166 mg, 0.36 mmol) were dissolved in N,N-dimethylformamide (3 mL). The reaction mixture was replaced with nitrogen three times to remove the oxygen inside the system and then heated at 110° C. for 16 hours. The reaction mixture was cooled to room temperature and filtered through diatomite. The filtrate was diluted with ice water (10 mL) and extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was purified by silica gel thin layer chromatography preparative plate (petroleum ether:ethyl acetate=1:1) to deliver a white solid 41-a (236 mg, yield: 34%). LC-MS (ESI): m/z=587 [M+H]$^+$.

Preparation of Compound 41.

Compound 41-a (236 mg, 0.41 mmol) was dissolved in dichloromethane (3 mL). The reaction solution was cooled to 0° C., trifluoroacetic acid (3 mL, 38.85 mmol) was added and the reaction mixture was stirred at room temperature for 3 hours. The reaction mixture was concentrated under reduced pressure and the residue was dissolved in ethyl acetate (50 mL) and washed with saturated aqueous sodium bicarbonate solution (50 mL). The separated organic phase was concentrated under reduced pressure and the residue was purified by high performance liquid chromatography (mobile phase: 0.05% TFA in water:acetonitrile=35%-45%) to deliver a pale yellow solid 41 (54 mg, yield: 28%). LC-MS (ESI): m/z=487 [M+H]$^+$.

$^1$H-NMR (400 MHz, CDCl$_3$) δ: 9.08 (s, 1H), 8.06 (d, J=8 Hz, 1H), 7.74 (dd, J=1 Hz, J=8 Hz, 2H), 7.47 (s, 1H), 7.33-7.41 (m, 2H), 6.83 (s, 1H), 6.81 (d, J=8 Hz, 1H), 6.65 (d, J=8 Hz, 1H), 4.58 (t, J=8 Hz, 2H), 3.67 (s, 3H), 3.48 (t, J=8 Hz, 2H), 3.17 (m, 2H), 3.03 (m, 2H), 2.09 (m, 2H), 1.76 (m, 2H) ppm.

Example 42

N-[7-(2-methoxyphenyl)-6-methylthieno[3,2-d]pyrimidin-2-yl]-3-(piperidin-4-yl)-1-isopropyl-1-H-pyrazol-5-amine (Compound 42)

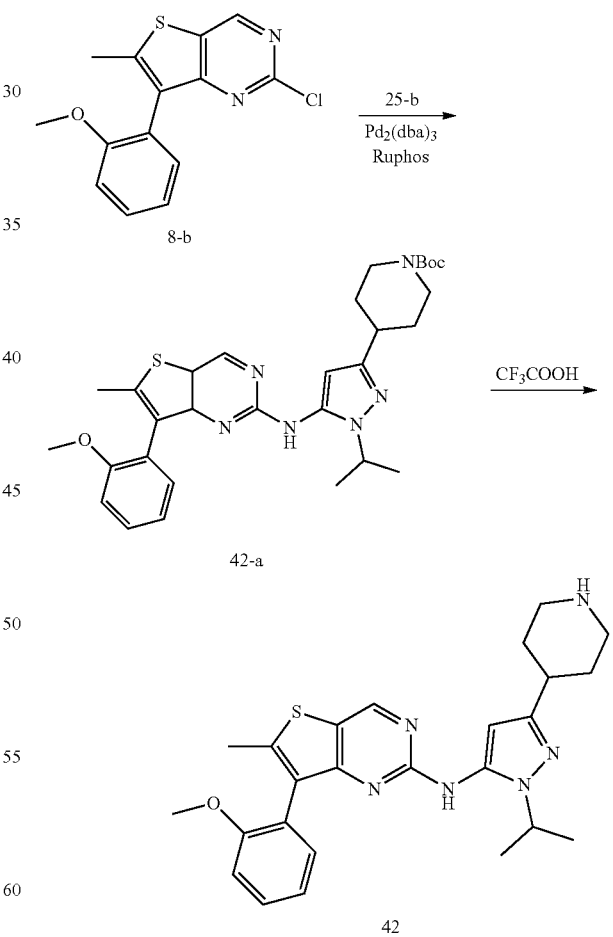

Preparation of Compound 42-a.

Compound 25-b (175 mg, 0.57 mmol), compound 8-b (150 mg, 0.52 mmol), tris(dibenzylideneacetone)dipalladium (89 mg, 0.16 mmol), potassium carbonate (216 mg, 1.56 mmol) and 2-dicyclohexylphosphino-2',6'-di-isopropoxy-1,1'-biphenyl(73 mg, 0.16 mmol) were dissolved in N,N-dimethylformamide (3 mL), and the reaction mixture was replaced with nitrogen three times to remove the oxygen inside the system and then heated at 110° C. for 4 hours. The reaction mixture was cooled to room temperature, diluted with ethyl acetate (50 mL) and ice water (50 mL) and extracted with ethyl acetate (50 mL×2). The combined organic phases were washed with water (50 mL×3) and brine (50 mL), dried over anhydrous sodium sulfate, filtered, and the filtrate was concentrated under reduced pressure. The residue was purified by silica gel thin layer chromatography preparative plate (petroleum ether:ethyl acetate=3:1) to deliver a pale yellow solid 42-a (179 mg, yield: 44%). LC-MS (ESI): m/z=563 [M+H]$^+$.

Preparation of Compound 42.

Compound 42-a (179 mg, 0.32 mmol) was dissolved in dichloromethane (3 mL). The reaction solution was cooled to 0° C., trifluoroacetic acid (3 mL, 25.8 mmol) was added and the reaction mixture was stirred at room temperature for 3 hours. The reaction mixture was concentrated under reduced pressure and the residue was dissolved in ethyl acetate (50 mL) and diluted with 1 M aqueous hydrochloric acid solution (50 mL). The pH of the separated aqueous phase was adjusted to 10 with saturated aqueous potassium carbonate solution, a solid was precipitated and filtered. The filter cake was washed with water (20 mL×3) and the solid was dried in vacuo to deliver a yellow solid 42 (80 mg, yield: 54%). LC-MS (ESI): m/z=463 [M+H]$^+$.

$^1$H-NMR (400 MHz, CD$_3$OD) δ: 8.83 (s, 1H), 7.41-7.45 (m, 1H), 7.25 (dd, J=8 Hz, J=1 Hz, 1H), 7.13 (d, J=8 Hz, 2H), 7.05-7.09 (m, 1H), 6.12 (s, 1H), 4.44-4.51 (m, 1H), 3.73 (s, 3H), 3.17-3.21 (m, 2H), 2.71-2.83 (m, 3H), 2.46 (s, 3H), 1.89-1.93 (m, 2H), 1.58-1.68 (m, 2H), 1.32 (d, J=7 Hz, 6H) ppm.

Example 43

N-[2,2-dimethyl-4-(piperidin-4-yl)-2,3-dihydro-1-benzofuran-7-yl]-7-(2-methoxyphenyl)-6-methylthieno[3,2-d]pyrimidin-2-amine (Compound 43)

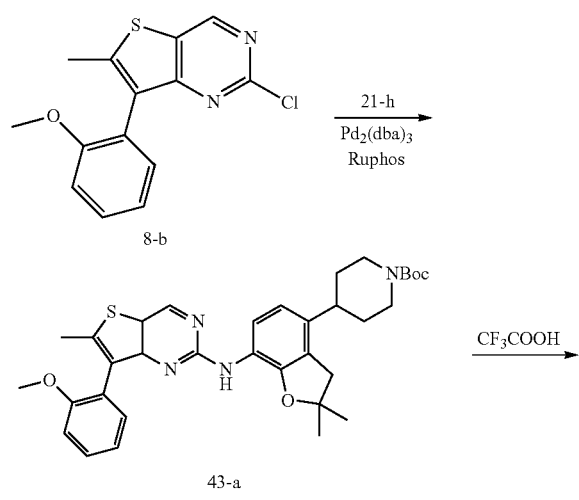

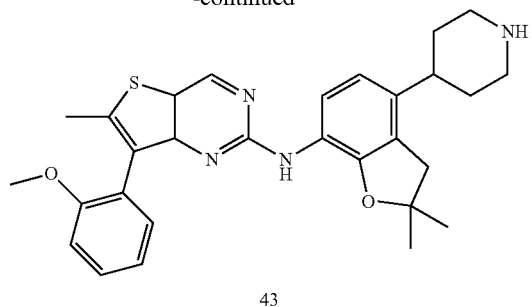

43

Preparation of Compound 43-a.

Compound 21-h (143 mg, 0.41 mmol), compound 8-b (120 mg, 0.41 mmol), cesium carbonate (401 mg, 1.23 mmol), tris(dibenzylideneacetone)dipalladium (71 mg, 0.13 mmol) and 2-dicyclohexylphosphino-2',6'-di-iso-propoxy-1,1'-biphenyl(58 mg, 0.13 mmol) were dissolved in N,N-dimethylformamide (3 mL), and the reaction mixture was replaced with nitrogen three times to remove the oxygen inside the system and then heated at 110° C. for 4 hours. The reaction mixture was cooled to room temperature, diluted with water (20 mL) and extracted with ethyl acetate (50 mL×3). The combined organic phases were washed successively with water (20 mL×3) and brine (20 mL), dried over anhydrous sodium sulfate, filtered, the filtrate was concentrated under reduced pressure. The residue was purified by silica gel thin layer chromatography preparative plate (petroleum ether:ethyl acetate=3:1) to deliver a pale yellow solid 43-a (98 mg, yield: 40%). LC-MS (ESI): m/z=601 [M+H]$^+$.

Preparation of Compound 43.

Compound 43-a (98 mg, 0.16 mmol) was dissolved in dichloromethane (3 mL). The reaction solution was cooled to 0° C., trifluoroacetic acid (3 mL) was added, and the reaction mixture was stirred at room temperature for 3 hours. The reaction mixture was concentrated under reduced pressure and the residue was dissolved in dichloromethane (50 mL) and washed with saturated aqueous potassium carbonate (50 mL). The organic phase was dried over anhydrous sodium sulfate, filtered, and the filtrate was concentrated under reduced pressure. The residue was purified by silica gel thin layer chromatography preparative plate (dichloromethane:methanol=10:1) to deliver a pale yellow solid 43 (35 mg, yield: 43%). LC-MS (ESI): m/z=501 [M+H]$^+$.

$^1$H-NMR (400 MHz, CDCl$_3$) δ: 8.76 (s, 1H), 8.21 (d, J=8 Hz, 1H), 7.45-7.50 (m, 1H), 7.40 (dd, J=8 Hz, J=2 Hz, 1H), 7.23 (s, 1H), 7.12-7.15 (m, 1H), 7.08 (d, J=8 Hz, 1H), 6.56 (d, J=8 Hz, 1H), 3.79 (s, 3H), 3.56 (m, 2H), 3.03 (s, 2H), 2.98 (m, 2H), 2.63 (m, 1H), 2.50 (s, 3H), 2.13 (m, 2H), 1.97 (m, 2H), 1.47 (s, 6H) ppm.

Example 44

1-[4-(7-{[8-(4-Fluoro-2-methoxyphenyl)quinazolin-2-yl]amino-2,3-dihydro-1-benzofuran-4-yl)piperidin-1-yl]prop-2-en-1-one (Compound 44)

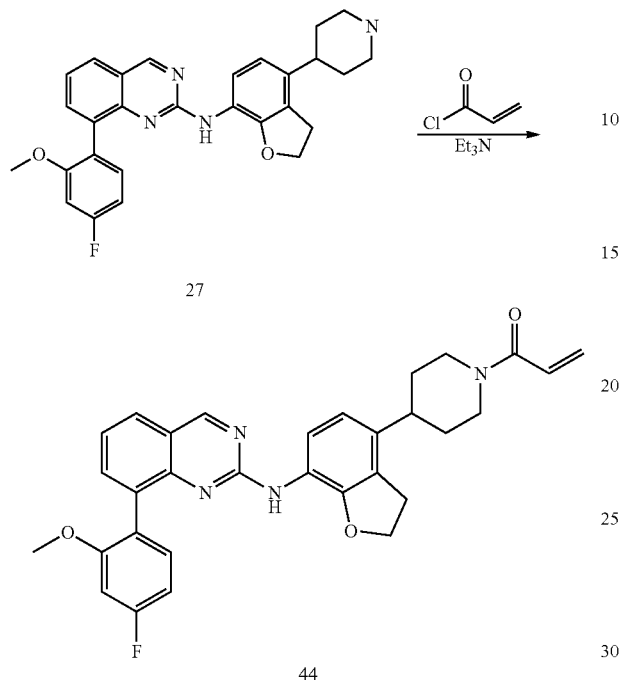

Preparation of Compound 44.

Compound 27 (300 mg, 0.64 mmol) was dissolved in dichloromethane (10 mL). The reaction solution was cooled to 0° C. and acryloyl chloride (86 mg, 0.96 mmol) and triethylamine (130 mg, 1.28 mmol) were added and the reaction mixture was stirred at 0° C. for 1 hour. The reaction mixture was concentrated under reduced pressure and the residue was purified by silica gel thin layer chromatography preparative plate (dichloromethane:methanol=40:1) and further purified by high performance liquid phase (mobile phase: 10 mM NH$_4$CO$_3$ aqueous solution:acetonitrile=25%-75%) to deliver a yellow solid 44 (26 mg, yield: 8%). LC-MS (ESI): m/z=525 [M+H]$^+$.

$^1$H-NMR (400 MHz, DMSO) δ: 9.26 (s, 1H), 8.19 (s, 1H), 7.89 (d, J=7.0 Hz, 1H), 7.69 (d, J=7.0 Hz, 1H), 7.63 (d, J=8.6 Hz, 1H), 7.39 (t, J=7.5 Hz, 1H), 7.27 (t, 1H), 7.07 (dd, J=2.4 Hz, 1H), 6.87 (m, 2H), 6.46 (d, J=8.3 Hz, 1H), 6.14 (dd, J=2.4 Hz, 1H), 5.70 (dd, J=2.4 Hz, 1H), 4.59 (m, 1H), 4.51 (t, 2H), 4.18 (d, 1H), 3.59 (s, 3H), 3.22-3.15 (m, 3H), 2.76-2.66 (m, 2H), 1.77 (m, 2H), 1.50 (m, 2H) ppm.

Example 45

7-[4-Fluoro-2-methoxyphenyl]-6-methyl-N-[4-(piperidin-4-yl)-2,3-dihydro-1-benzofuran-7-yl]thieno[3,2-d]pyrimidin-2-amine (Compound 45)

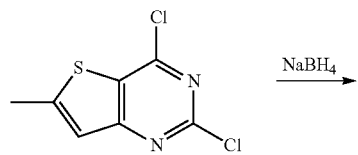

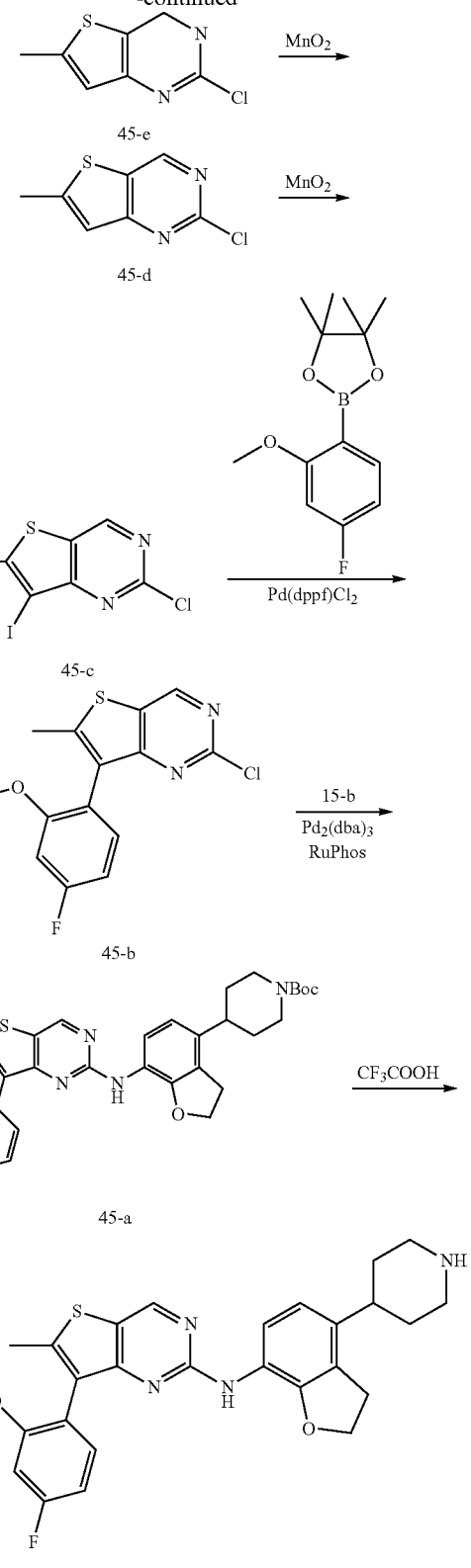

Preparation of Compound 45-e.

2,4-Dichloro-6-methylthieno[3,2-d]pyrimidine (10 g, 45.6 mmol) was dissolved in a mixed solution of tetrahydrofuran (100 mL) and ethanol (100 mL), the reaction solution was cooled to 0° C., sodium borohydride (12.5 g, 198 mmol) was added in batches. The reaction mixture was allowed to warm to room temperature and stirring was continued for 16 hours. The reaction mixture was diluted with water (500 mL) and then the pH was adjusted to 7 with 1 N aqueous hydrochloric acid solution. The aqueous phase was extracted with ethyl acetate (150 mL×3). The organic phase was washed successively with water (100 mL×3) and brine (100 mL), dried over anhydrous sodium sulfate, filtered and the filtrate was concentrated under reduced pressure to deliver a white solid 45-e (7.5 g, yield: 88%). This product was used without further purification. LC-MS (ESI): m/z=187 [M+H]$^+$.

Preparation of Compound 45-d.

Compound 45-e (7.5 g, 40 mmol) was dissolved in chloroform (300 mL) at 0° C. Activated manganese dioxide (35 g, 400 mmol) was added and the reaction mixture was allowed to warm to room temperature and stirring was continued for 16 hours. The reaction mixture was filtered through diatomite and the filter cake was washed with chloroform (100 mL×3). The combined filtrates were concentrated under reduced pressure to deliver a white solid 45-d (6.6 g, yield: 89%). This product was used without further purification. LC-MS (ESI): m/z=185 [M+H]$^+$.

Preparation of Compound 45-c.

Compound 45-d (3.1 g, 16.8 mmol) was dissolved in trifluoroacetic acid (30 mL) at 0° C. and N-iodosuccinimide (5.7 g, 25.3 mmol) was added in batches and the reaction mixture was allowed to warm to room temperature and stirring was continued for 1 hour. The reaction mixture was quenched by adding water (50 mL) and extracted with dichloromethane (50 mL×3). The organic phase was washed successively with water (50 mL×3) and brine (50 mL), dried over anhydrous sodium sulfate, filtered and the filtrate was concentrated under reduced pressure to deliver a white solid 45-c (4.9 g, yield: 94%). This product was used without further purification. LC-MS (ESI): m/z=311 [M+H]$^+$.

Preparation of Compound 45-b.

Compound 45-c (615 mg, 1.98 mmol), 2-methoxy-4-fluorophenylboronic acid (405 mg, 2.38 mmol) and sodium carbonate (630 mg, 5.94 mmol) were suspended in dioxane (5 mL) and water (5 mL), [1,1'-bis(diphenylphosphino)ferrocene]dichloropalladium (II) dichloro methane complex (163 mg, 0.2 mmol) was added. The reaction mixture was replaced with nitrogen three times and then heated to 80° C. and reacted for 16 hours. After the reaction mixture was cooled to room temperature, the reaction mixture was concentrated under reduced pressure. The residue was layered with dichloromethane (50 mL) and water (50 mL). The organic phase was dried over anhydrous sodium sulfate, filtered, and the filtrate was concentrated and purified by silica gel column chromatography (petroleum ether:dichloromethane=1:1) to deliver a white solid 45-b (240 mg, yield: 39%). LC-MS (ESI): m/z=309 [M+H]$^+$.

Preparation of Compound 45-a.

Compound 45-b (300 mg, 0.97 mmol), compound 15-b (309 mg, 0.97 mmol), potassium carbonate (402 mg, 2.91 mmol), tris(dibenzylideneacetone)dipalladium (44 mg, 0.048 mmol) and 2-dicyclohexylphosphino-2',6'-di-isopropoxy-1,1'-biphenyl (23 mg, 0.048 mmol) were dissolved in N,N-dimethylformamide (10 mL). The reaction mixture was replaced with nitrogen three times to remove the oxygen inside the system and then heated at 110° C. for 16 hours. The reaction mixture was cooled to room temperature, diluted with ice water (20 mL) and extracted with dichloromethane (50 mL×3). The combined organic phases were washed successively with water (20 mL×3) and brine (20 mL), dried over anhydrous sodium sulfate, filtered, and the filtrate was concentrated under reduced pressure. The residue was purified by silica gel column chromatography (petroleum ether:ethyl acetate=5:1) to deliver a yellow solid 45-a (274 mg, yield: 48%). LC-MS (ESI): m/z=591 [M+H]$^+$.

Preparation of Compound 45.

Compound 45-a (276 mg, 0.46 mmol) was dissolved in dichloromethane (8 mL). The reaction solution was cooled to 0° C., trifluoroacetic acid (3 mL) was added, and the reaction mixture was stirred at room temperature for 16 hours. The reaction mixture was concentrated under reduced pressure and the residue was diluted with water (30 mL), the pH was adjusted to 10 with saturated aqueous potassium carbonate solution. The aqueous phase was extracted with dichloromethane (50 mL×3). The combined organic phases were washed with water (20 mL×3) and brine (20 mL), dried over anhydrous sodium sulfate, filtered, and the filtrate was concentrated under reduced pressure. The residue was washed with ethyl acetate to deliver compound 45 (126 mg, yield: 56%). LC-MS (ESI): m/z=491 [M+H]$^+$.

$^1$H NMR (400 MHz, DMSO) δ: 8.93 (s, 1H), 8.05 (s, 1H), 7.53 (d, J=8.2 Hz, 1H), 7.35-7.27 (t, 1H), 7.11-7.00 (m, 1H), 6.90 (m, 1H), 6.55 (d, J=8.3 Hz, 1H), 4.51 (t, J=8.4 Hz, 2H), 3.73 (s, 3H), 3.18 (t, J=8.6 Hz, 3H), 3.08 (d, J=11.7 Hz, 2H), 2.67-2.61 (m, 3H), 2.40 (s, 3H), 1.70-1.50 (m, 4H) ppm.

Effect Example: Enzyme Activity Inhibition IC$_{50}$ Evaluation Experiment of Anaplastic Lymphoma Kinase ALK Buffer preparation: 50 mM HEPES, pH 7.5, 0.00015% Brij-35.

The compound was configured as a concentration gradient in 100% DMSO and added to a 384-well plate with a final DMSO concentration of 2%.

1. ALK enzyme (purchased from Carna Biosciences, Inc.) was diluted to the optimum concentration with the following buffer: 50 mM HEPES, pH 7.5, 0.00015% Brij-35, 2 mM DTT, which was transferred to a 384-well plate and incubated with the compound for a certain time.

2. The substrate was diluted to the optimum concentration with the following buffer: 50 mM HEPES, pH 7.5, 0.00015% Brij-35, mM MgCl$_2$, adenosine triphosphate under Km, which was added to the 384-well plate to initiate the reaction and reacted at 28° C. for 1 hour.

3. The conversion rate was read by Caliper Reader, the calculated inhibition rate is the average of the two tests.

The compounds of the present invention were tested for the inhibitory activity of ALK according to the above test. The results were as follows (Table 1):

TABLE 1

IC$_{50}$ values of some compounds of the present invention for the inhibition of ALK activity

| Compound | IC$_{50}$ (nM) | Compound | IC$_{50}$ (nM) |
| --- | --- | --- | --- |
| 1 | 5.5 | 3 | 14 |
| 8 | 6.4 | 11 | 27.7 |
| 15 | 3.3 | 16 | 9.3 |
| 17 | 2.1 | 18 | 9.1 |
| 20 | 12.8 | 22 | 34 |
| 23 | 12 | 24 | 36 |
| 25 | 27 | 27 | 5.1 |
| 28 | 34 | 29 | 14 |
| 30 | 14 | 31 | 2.3 |
| 32 | 35 | 33 | 2.5 |
| 34 | 14 | 35 | 3.4 |

TABLE 1-continued

IC₅₀ values of some compounds of the present invention for the inhibition of ALK activity

| Compound | IC$_{50}$ (nM) | Compound | IC$_{50}$ (nM) |
| --- | --- | --- | --- |
| 37 | 3.3 | 40 | 12 |
| 42 | 2.7 | 43 | 10.9 |

The invention claimed is:

1. A condensed-ring pyrimidylamino derivative having a structure of formula II-1, a tautomer, a mesomer, a racemate, a stereoisomer, a pharmaceutically acceptable salt or a prodrug thereof:

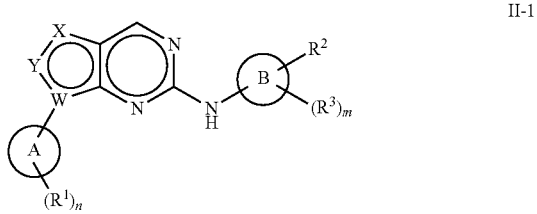

II-1 wherein,
X is S;
Y is CR⁴;
W is C;
ring A is an aromatic ring or a heteroaromatic ring;
R¹ is selected from hydrogen atom, hydroxyl, a halogen, an alkyl, a sulfonyl, an alkoxy, formyl, amino, an amide or a heteroaryl, or the two adjacent R¹(s) and the two atoms on the ring A connected to them form a 5- to 7-membered heterocyclic ring together; in the heterocyclic ring, the heteroatom(s) is(are) oxygen and/or nitrogen, the number of the heteroatom(s) is 1 to 4, and the number of carbon atom(s) is 1 to 6;
where, in R¹, the alkyl, the alkoxy, the formyl, the amino, the sulfonyl or the heteroaryl are optionally independently substituted by a substituent selected from the group consisting of a halogen, a C$_{1-10}$ alkyl, hydroxy, amino, a C$_{1-10}$ alkoxy, a C$_{1-4}$ sulfonyl and a heterocycloalkyl having 3 to 8 carbon atoms in which the heteroatom is oxygen and/or nitrogen and the number of the heteroatom(s) is 1 to 4; the heterocycloalkyl ring is optionally substituted by a substituent selected from the group consisting of a C$_{1-4}$ alkyl;
R² is selected from an amide or a heterocycloalkyl which is piperidinyl;
where, in R², the heterocycloalkyl which is piperidinyl is optionally substituted by a substituent selected from the group consisting of: hydroxy, a C$_{1-4}$ alkyl and a C$_{1-4}$ acyl;
or R² is

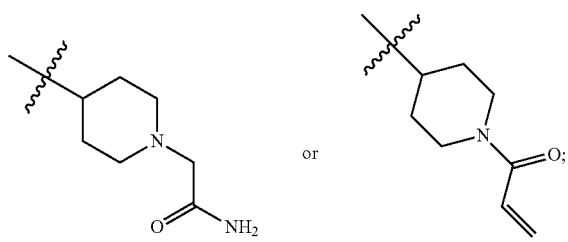 [SMILES: *C1CCN(CC(N)=O)CC1 ; "or" ; *C1CCN(C(=O)C=C)CC1]

ring B is an aromatic ring or a heteroaromatic ring,
m is 1 or 2,
R³ is selected from hydrogen atom, hydroxyl, a halogen, an alkyl, an alkoxy, or the two adjacent R³(s) together with the carbon atoms on the ring B to which they are attached to form a 5- to 7-membered heterocyclyl together; the heterocyclyl is a heterocyclyl wherein the heteroatom is selected from the group consisting of oxygen, nitrogen and sulfur, the number of the heteroatom(s) is 1 to 4, and the number of carbon atoms is 2 to 6;
where, in R³, the alkyl or the alkoxy is optionally independently substituted by a substituent selected from the group consisting of a halogen, a C$_{1-4}$ alkyl, hydroxy, amino, a C$_{1-4}$ alkoxy, a C$_{1-4}$ sulfonyl and an amide; and the heterocyclyl is optionally substituted by a substituent selected from the group consisting of a C$_{1-4}$ alkyl;
R⁴ is selected from hydrogen atom, a halogen or an alkyl;
n is 1 or 2; and
the amide is

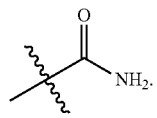

2. The condensed-ring pyrimidylamino derivative, the tautomer, the mesomer, the racemate, the stereoisomer, the pharmaceutically acceptable salt or the prodrug thereof according to claim 1, wherein, the condensed-ring pyrimidylamino derivative having the structure of formula II-1 is represented by formula III-1-1 or III-1-2,

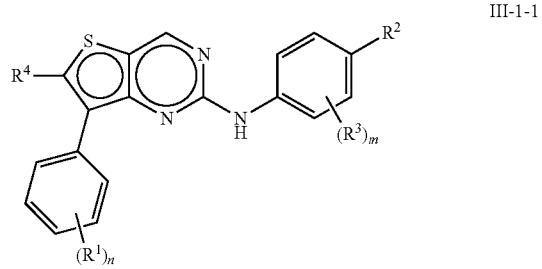

III-1-1

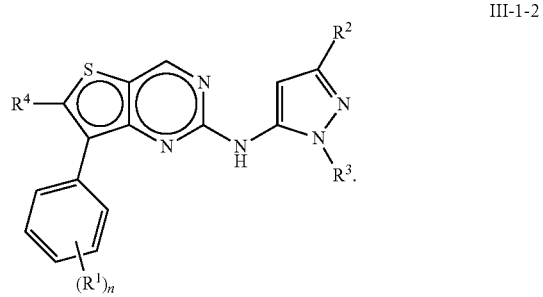

III-1-2

3. The condensed-ring pyrimidylamino derivative, the tautomer, the mesomer, the racemate, the stereoisomer, the pharmaceutically acceptable salt or the prodrug thereof according to claim 1, wherein:
in the ring A, the aromatic ring is a C$_{6-10}$ aromatic ring, and in the ring A, the heteroaromatic ring is a heteroaromatic ring having 2 to 5 carbon atoms in which the heteroatom is nitrogen atom and the number of the heteroatom(s) is 1 to 3;

in the ring B, the aromatic ring is a $C_{6-10}$ aromatic ring, and in the ring B, the heteroaromatic ring is a heteroaromatic ring having 2 to 5 carbon atoms in which the heteroatom is a nitrogen atom and the number of the heteroatom(s) is 1 to 3;

in the $R^1$, the halogen is fluorine or chlorine; the alkyl is a $C_{1-4}$ alkyl; the sulfonyl is a $C_{1-4}$ sulfonyl; the alkoxy is a $C_{1-4}$ alkoxy; the heteroaryl is a heteroaryl having 2 to 5 carbon atoms in which the heteroatom is nitrogen atom and the number of the heteroatom(s) is 1 to 3; the carbon heterocyclic ring is one having 2 to 5 carbon atoms in which the heteroatom is oxygen, the number of the heteroatom(s) is 1 or 2; and in the $R^3$, the alkyl is a $C_{1-4}$ alkyl; the alkoxy is a $C_{1-4}$ alkoxy; the heterocyclyl is a heterocyclyl having 2 to 4 carbon atoms in which the heteroatom is oxygen and the number of the heteroatom(s) is 1 to 2.

4. The condensed-ring pyrimidylamino derivative, the tautomer, the mesomer, the racemate, the stereoisomer, the pharmaceutically acceptable salt or the prodrug thereof according to claim 3, wherein:

in the ring A, the $C_{6-10}$ aromatic ring is benzene ring, the heteroaromatic ring is a heteroaromatic ring having 2 to 3 carbon atoms in which the heteroatom is nitrogen atom and the number of the heteroatom(s) is 1 or 2;

in the ring B, the $C_{6-10}$ aromatic ring is benzene ring, in the ring B, the heteroaromatic ring is a heteroaromatic ring having 2 to 3 carbon atoms in which the heteroatom is nitrogen atom and the number of the heteroatom(s) is 1 or 2; and in the $R^1$, the $C_{1-4}$ sulfonyl is methanesulfonyl, the heteroaryl is pyrazolyl, the carbon heterocyclic ring is one having 3 to 5 carbon atoms in which the heteroatom is oxygen, the number of the heteroatom(s) is 1 or 2.

5. The condensed-ring pyrimidylamino derivative, the tautomer, the mesomer, the racemate, the stereoisomer, the pharmaceutically acceptable salt or the prodrug thereof according to claim 4, wherein:

in the ring A, the heteroaromatic ring is a pyrazole ring or triazole ring; and in the ring B, the heteroaromatic ring is pyrazole ring.

6. The condensed-ring pyrimidylamino derivative, the tautomer, the mesomer, the racemate, the stereoisomer, the pharmaceutically acceptable salt or the prodrug thereof according to claim 1, wherein:

in the substituent(s) of $R^1$, the halogen is fluorine; the $C_{1-10}$ alkyl is a $C_{1-4}$ alkyl; the $C_{1-10}$ alkoxy is a $C_{1-4}$ alkoxy; the $C_{1-4}$ sulfonyl is methanesulfonyl, the heterocycloalkyl is a heterocycloalkyl having 4 to 6 carbon atoms in which the heteroatom is oxygen and/or nitrogen, the number of the heteroatom(s) is 1 to 4; and in the substituent(s) of $R^3$, the halogen is fluorine, and the $C_{1-4}$ sulfonyl is methanesulfonyl.

7. The condensed-ring pyrimidylamino derivative, the tautomer, the mesomer, the racemate, the stereoisomer, the pharmaceutically acceptable salt or the prodrug thereof according to claim 6, wherein, in the substituent(s) of $R^1$, the heterocycloalkyl is morpholinyl.

8. The condensed-ring pyrimidylamino derivative, the tautomer, the mesomer, the racemate, the stereoisomer, the pharmaceutically acceptable salt or the prodrug thereof according to claim 1, wherein, the $R^1$ is

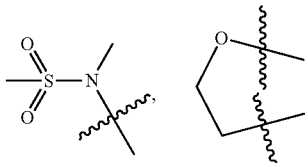

methyl,

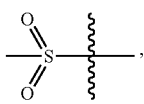

methoxy, ethoxy, trifluoromethyl, fluorine,

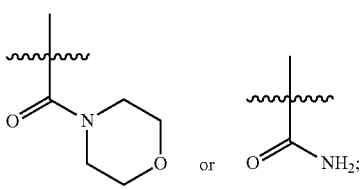

the $R^2$ is

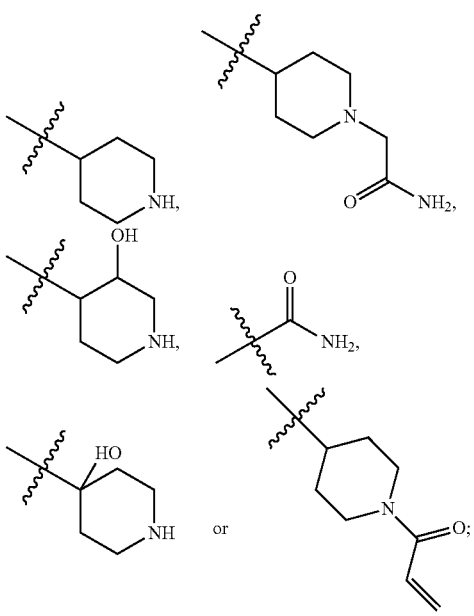

the $R^3$ is methoxy, isopropoxy, methyl,

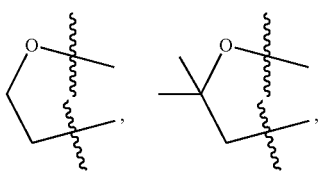

isopropyl,

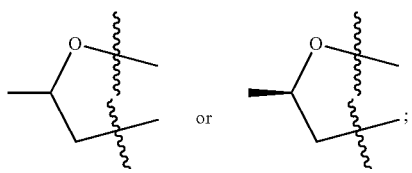
and
the R⁴ is methyl or fluorine.
9. The condensed-ring pyrimidylamino derivative, the tautomer, the mesomer, the racemate, the stereoisomer, the pharmaceutically acceptable salt or the prodrug thereof according to claim 1, wherein,
the
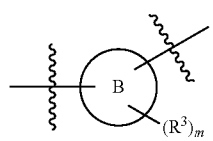
is
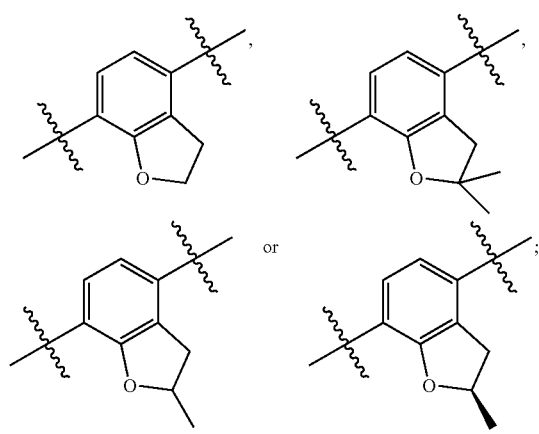
and
the
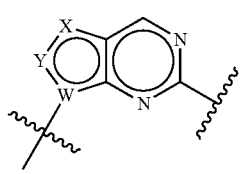
is
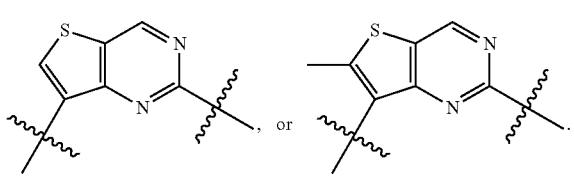 [SMILES: *c1ncc2scc(*)c2n1 ; *c1ncc2sc(C)c(*)c2n1]
10. Any one of the compounds selected from the group consisting of the following compounds:
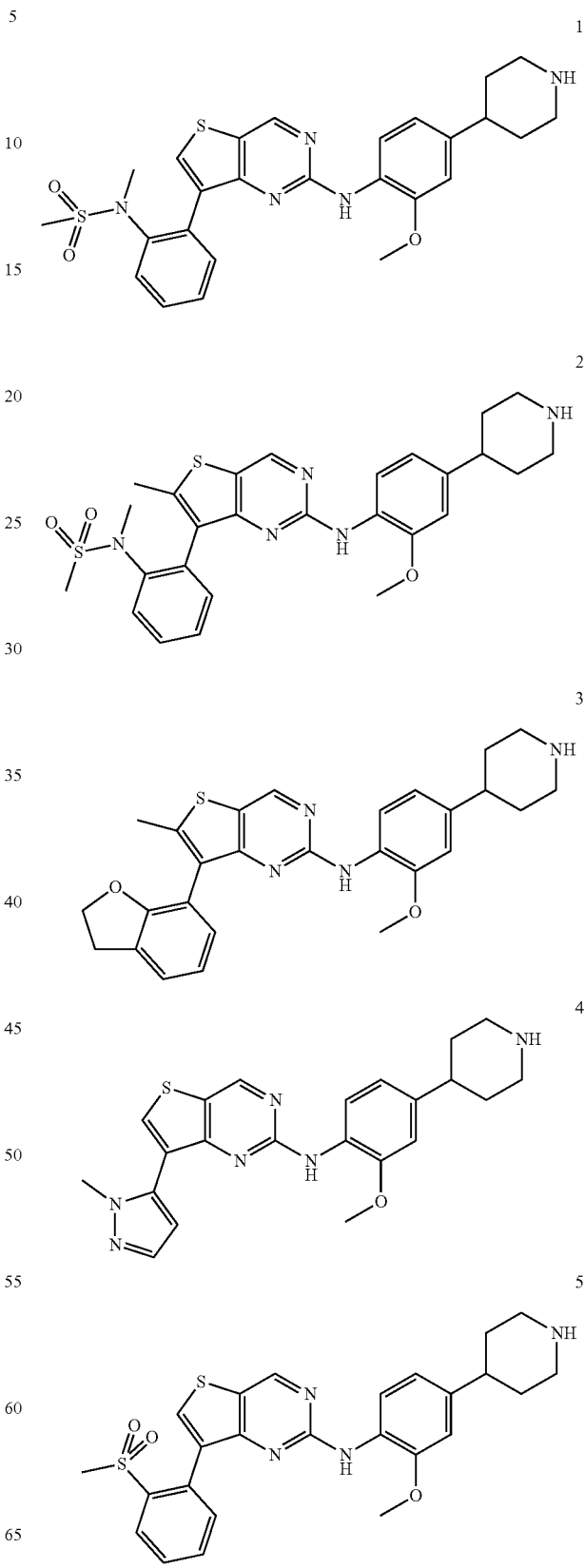

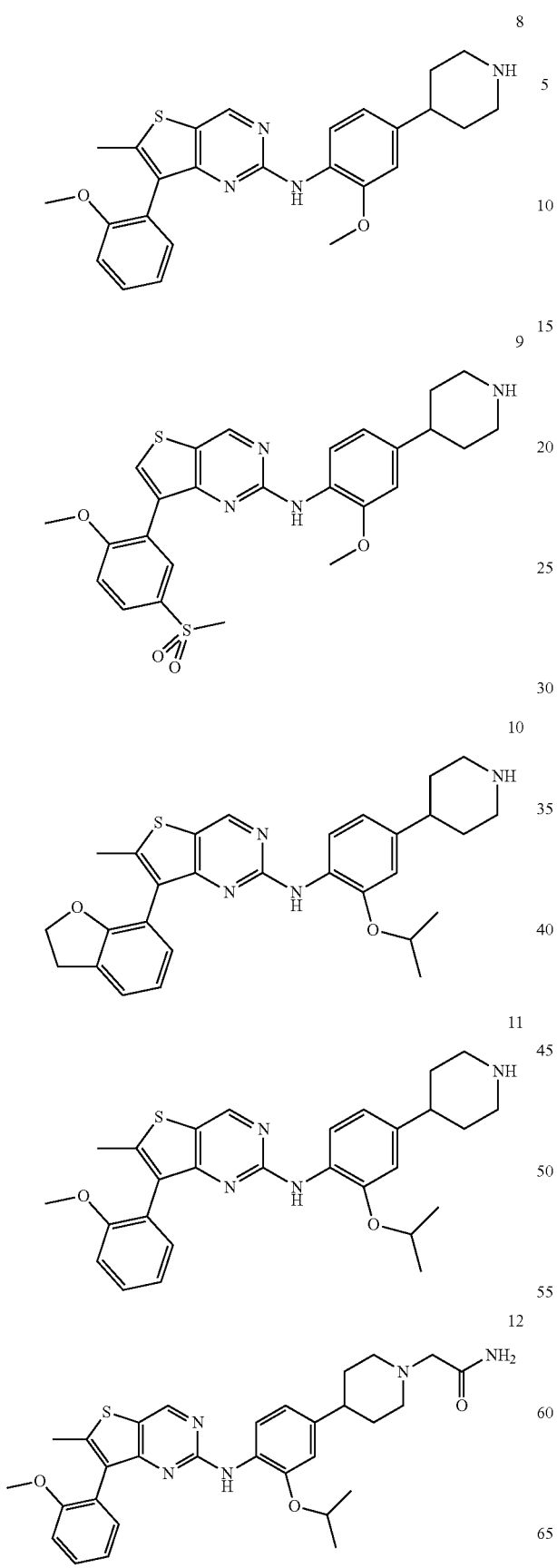
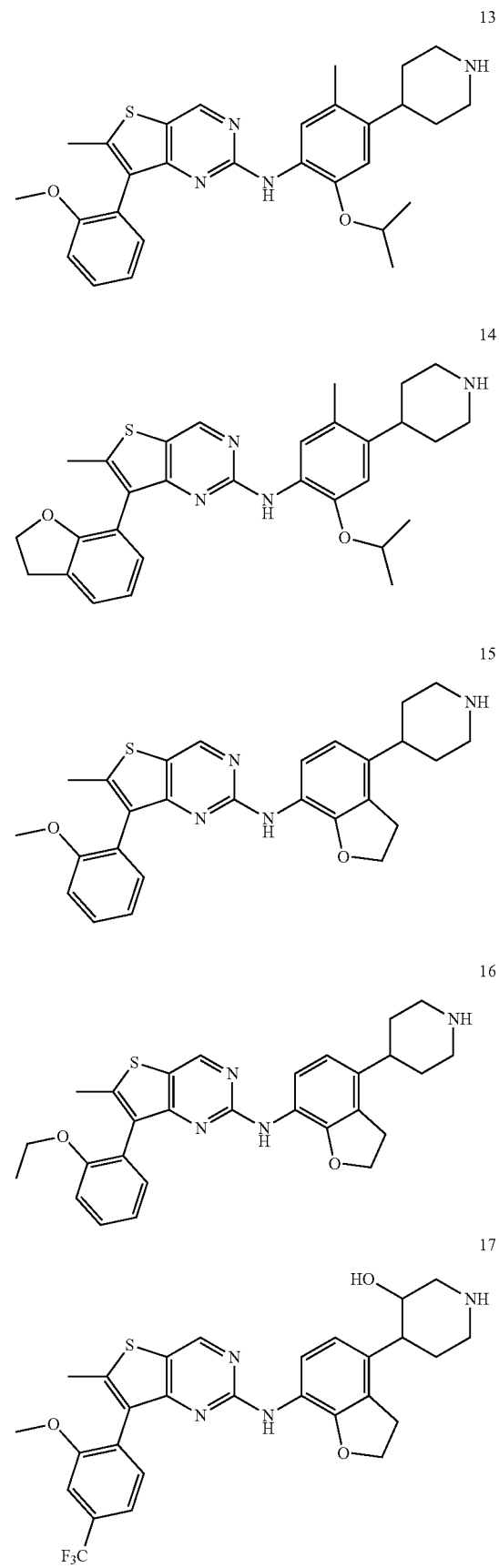

-continued

18
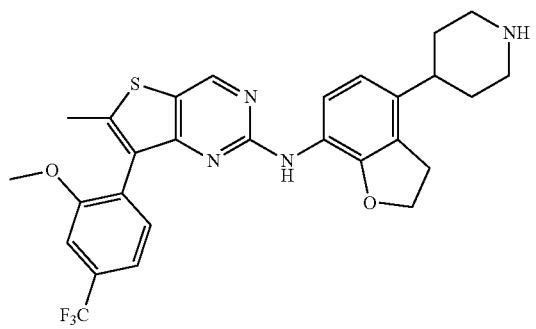

42
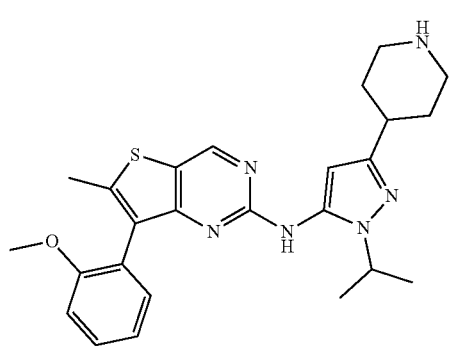

43
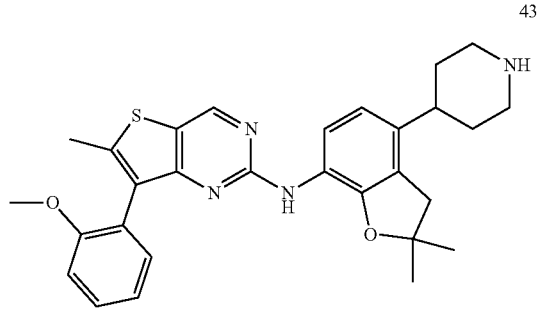

45
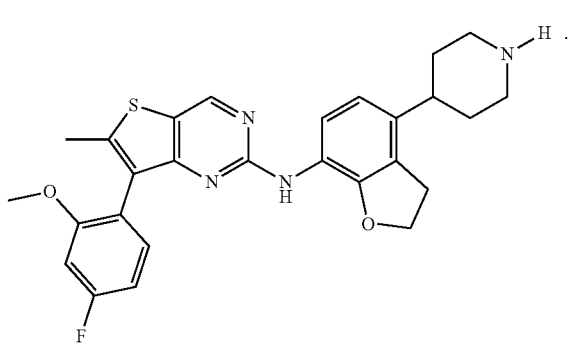

11. A pharmaceutical composition, which comprises a therapeutically effective amount of a compound selected from the group consisting of the condensed-ring pyrimidylamino derivative, the tautomer, the mesomer, the racemate, the stereoisomer thereof, the pharmaceutically acceptable salt and the prodrug thereof according to claim 1, and a pharmaceutically acceptable carrier and/or a diluter.

12. A method for inhibiting anaplastic lymphoma kinase activity in a subject in need thereof, comprising administering to the subject a medicament comprising an effective amount of the condensed-ring pyrimidylamino derivative, the tautomer, the mesomer, the racemate, the stereoisomer, thereof, the pharmaceutically acceptable salt or the prodrug thereof according to claim 1.

13. A method for inhibiting anaplastic lymphoma kinase activity in a subject in need thereof, comprising administering to the subject a medicament comprising an effective amount of the pharmaceutical composition according to claim 11.

14. A process for preparing the condensed-ring pyrimidylamino derivative, the tautomer, the mesomer, the racemate, the stereoisomer, the pharmaceutically acceptable salt or the prodrug thereof according to claim 1, comprising: in a solvent, in the presence of a palladium-containing catalyst, allowing a compound represented by formula I-a and a compound represented by formula I-b' to have a coupling reaction, and then preparing a compound represented by formula I by means of a deprotection reaction

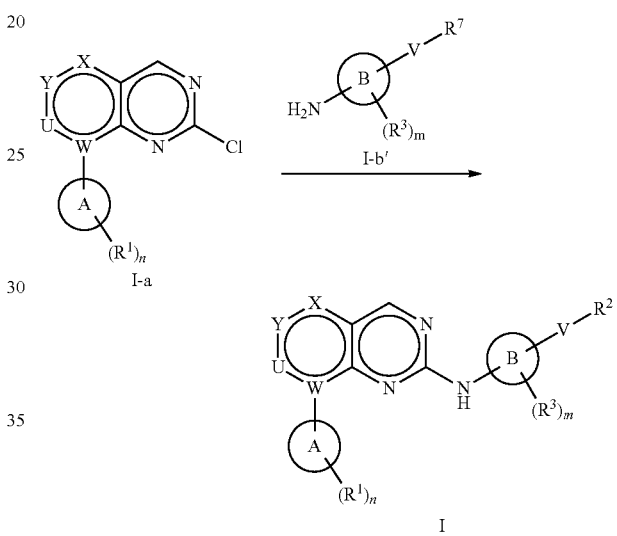

in formula I-a, formula I-b' and formula I, both U and V are a chemical bond, other substituents are as defined in claim 1, $R^7$ is $R^2$ that is protected by Boc;

or, optionally, a base is also included in the coupling reaction, where the base is sodium carbonate, potassium carbonate or cesium carbonate, and the molar ratio of the base to the compound I-a is from 1:1 to 5:1.

15. The process according to claim 14, further comprising: in a solvent, in the presence of a palladium-containing catalyst, reacting a compound having a structure of I-c and a compound having a structure of I-d by a coupling reaction to deliver the compound of formula I-a,

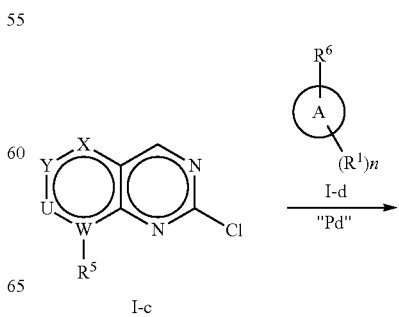

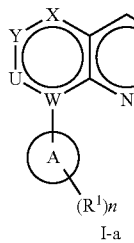

wherein, $R^5$ is a halogen, $R^6$ is a boric acid or a borate.

16. The process according to claim 14, wherein the solvent is an organic solvent and/or water, where the organic solvent is selected from the group consisting of 1,4-dioxane, toluene, ethylene glycol dimethyl ether and N,N-dimethylformamide, the volume-to-mass ratio of the organic solvent to the compound having the structure of formula I-a is from 10 mL/g to 110 mL/g, and, when the solvent is organic solvent and water, the amount of the water is 1 to 100% of the volume of the organic solvent.

17. The process according to claim 14, wherein the palladium-containing catalyst is selected from the group consisting of:
tris(dibenzylideneacetone)dipalladium, palladium acetate, tetrakis(triphenylphosphine)palladium and [1,1'-bis(diphenylphosphino)ferrocene]dichloropalladium(II);
where the molar ratio of the palladium-containing catalyst to the compound having the structure of formula I-a is from 0.005:1 to 0.5:1.

18. The process according to claim 14, wherein the molar ratio of the compound having the structure of formula I-a to the compound having the structure of formula I-b' is from 0.5:1 to 2:1.

19. The process according to claim 14, wherein the temperature of the coupling reaction is from 50° C. to 150° C.

* * * * *